US 9,040,663 B2

(12) United States Patent
Dodd et al.

(10) Patent No.: US 9,040,663 B2
(45) Date of Patent: *May 26, 2015

(54) MELANOCORTIN RECEPTOR-SPECIFIC PEPTIDES

(71) Applicant: AstraZeneca AB, Sodertalje (SE)

(72) Inventors: John H. Dodd, Cranbury, NJ (US); Yi-Qun Shi, Cranbury, NJ (US); Wei Yang, Cranbury, NJ (US)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/886,864

(22) Filed: May 3, 2013

(65) Prior Publication Data

US 2013/0237473 A1    Sep. 12, 2013

Related U.S. Application Data

(63) Continuation of application No. 12/795,469, filed on Jun. 7, 2010, now Pat. No. 8,455,617.

(60) Provisional application No. 61/184,932, filed on Jun. 8, 2009.

(51) Int. Cl.
*C07K 7/56* (2006.01)
*C07K 7/06* (2006.01)
*A61K 38/00* (2006.01)

(52) U.S. Cl.
CPC . *C07K 7/56* (2013.01); *A61K 38/00* (2013.01); *C07K 7/06* (2013.01)

(58) Field of Classification Search
None
See application file for complete search history.

(56) References Cited

U.S. PATENT DOCUMENTS

| | | | |
|---|---|---|---|
| 5,576,290 A | 11/1996 | Hadley | |
| 5,674,839 A | 10/1997 | Hruby et al. | |
| 5,731,408 A | 3/1998 | Hadley et al. | |
| 6,054,556 A | 4/2000 | Huby et al. | |
| 6,350,430 B1 | 2/2002 | Dooley et al. | |
| 6,476,187 B1 | 11/2002 | Cone et al. | |
| 6,579,968 B1 | 6/2003 | Blood et al. | |
| 6,600,015 B2 | 7/2003 | Chen et al. | |
| 6,613,874 B1 | 9/2003 | Mazur et al. | |
| 6,693,165 B2 | 2/2004 | Bednarek | |

(Continued)

FOREIGN PATENT DOCUMENTS

| | | |
|---|---|---|
| CA | 1340107 | 10/1998 |
| CA | 2158425 | 1/2003 |

(Continued)

OTHER PUBLICATIONS

Adan et al., "Characterization of melanocortin receptor ligands on cloned brain melanocortin receptors and on grooming behavior in the rat," European Journal of Pharmacology, 1999, 378: 249-258.
Adan et al., "The MC4 receptor and control of appetite," Br. J. Pharmacol., 2006, 149(7): 815-827.
Balbani, "Recent developments for smoking cessation and treatment of nicotine dependence," Expert Opin. Ther. Patents, 2007, 17(3): 287-297.
Ballet et al., "Novel selective human melanocortin-3 receptor ligands: use of the 4-amino-1,2,4,5-tetrahydro-2-benzazepin-3-one (Aba) scaffold," Bioorg. Med. Chem. Lett., 2007, 17(9): 2492-2498.
Balse-Srinivasa et al., "Structure-activity relationships of gamma-MSH analogues at the human melanocortin MC3, MC4, and MC5 receptors. Discovery of highly selective hMC3R, hMC4R, and hMC5R analogues," J. Med. Chem., 2003, 46(23): 4965-4973.

(Continued)

*Primary Examiner* — Maury Audet
(74) *Attorney, Agent, or Firm* — Morgan, Lewis & Bockius LLP

(57) ABSTRACT

The invention relates to melanocortin receptor-specific cyclic peptides of Formula (I)

(I)

or a pharmaceutically acceptable salt thereof, where $R_1$, $R_2$, $R_3$, $R_{4a}$, $R_{4b}$, $R_{4c}$, $R_5$, x and y are as defined in the specification. These compounds are particularly useful in the treatments of energy homeostasis and metabolism related (e.g. diabetes), food intake related and/or energy balance and body weight related diseases, disorders and/or conditions, including obesity, overweight and diseases, disorders and/or conditions associated with obesity and/or overweight, such as type 2 diabetes and metabolic syndrome.

11 Claims, No Drawings

(56) References Cited

U.S. PATENT DOCUMENTS

| | | | |
|---|---|---|---|
| 6,699,873 B1 | 3/2004 | Maguire et al. | |
| 6,794,489 B2 | 9/2004 | Blood et al. | |
| 6,887,846 B2 | 5/2005 | Catania et al. | |
| 6,951,916 B2 | 10/2005 | Mazur et al. | |
| 7,008,925 B1 | 3/2006 | Szardenings et al. | |
| 7,176,279 B2 | 2/2007 | Sharma et al. | |
| 7,326,707 B2 | 2/2008 | Sharma et al. | |
| 7,354,923 B2 | 4/2008 | Sharma et al. | |
| 7,456,184 B2 | 11/2008 | Sharma et al. | |
| 7,541,430 B2 | 6/2009 | Sensfuss et al. | |
| 7,655,658 B2 | 2/2010 | Sharma et al. | |
| 7,709,484 B1 | 5/2010 | Sharma et al. | |
| 7,718,802 B2 | 5/2010 | Sharma et al. | |
| 7,727,990 B2 | 6/2010 | Sharma et al. | |
| 7,727,991 B2 | 6/2010 | Sharma et al. | |
| 7,732,451 B2 | 6/2010 | Sharma et al. | |
| 7,807,678 B2 | 10/2010 | Sharma et al. | |
| 7,834,017 B2 | 11/2010 | Burris et al. | |
| 7,964,601 B2 | 6/2011 | Sharma et al. | |
| 7,968,548 B2 | 6/2011 | Sharma et al. | |
| 8,455,617 B2 * | 6/2013 | Dodd et al. | 530/328 |
| 8,455,618 B2 * | 6/2013 | Dodd et al. | 530/328 |
| 2001/0056179 A1 | 12/2001 | Chen et al. | |
| 2002/0143141 A1 | 10/2002 | Chen et al. | |
| 2003/0064921 A1 | 4/2003 | Millhauser et al. | |
| 2003/0105024 A1 | 6/2003 | Cone et al. | |
| 2003/0113263 A1 | 6/2003 | Marks et al. | |
| 2003/0212002 A1 | 11/2003 | Haskell-Luevano et al. | |
| 2004/0023859 A1 | 2/2004 | Mazur et al. | |
| 2004/0138136 A1 | 7/2004 | Sharma et al. | |
| 2005/0038230 A1 | 2/2005 | Sharma et al. | |
| 2005/0101535 A1 | 5/2005 | Rosenstein et al. | |
| 2005/0130901 A1 | 6/2005 | Lipton et al. | |
| 2005/0164914 A1 | 7/2005 | Sharma et al. | |
| 2005/0187164 A1 | 8/2005 | Pinel | |
| 2005/0222014 A1 | 10/2005 | Diamond et al. | |
| 2005/0239711 A1 | 10/2005 | Chen et al. | |
| 2006/0014194 A1 | 1/2006 | Sharma et al. | |
| 2006/0041021 A1 | 2/2006 | Wilson et al. | |
| 2006/0105951 A1 | 5/2006 | Cunningham et al. | |
| 2006/0111281 A1 | 5/2006 | Sharma et al. | |
| 2006/0135436 A1 | 6/2006 | Haskell-Luevano et al. | |
| 2006/0258590 A1 | 11/2006 | Haskell-Luevano | |
| 2006/0293223 A1 | 12/2006 | Gadski et al. | |
| 2007/0027091 A1 | 2/2007 | Conde-Frieboes et al. | |
| 2007/0105759 A1 | 5/2007 | Flora et al. | |
| 2007/0123453 A1 | 5/2007 | Heiman et al. | |
| 2007/0244054 A1 | 10/2007 | Sensfuss et al. | |
| 2007/0293423 A1 | 12/2007 | Jungheim et al. | |
| 2008/0039387 A1 | 2/2008 | Sensfuss et al. | |
| 2009/0076029 A1 | 3/2009 | Sharma et al. | |
| 2009/0081197 A1 | 3/2009 | Burris et al. | |
| 2009/0305960 A1 | 12/2009 | Chen et al. | |
| 2010/0311648 A1 | 12/2010 | Dodd et al. | |
| 2012/0046219 A1 | 2/2012 | Dodd et al. | |

FOREIGN PATENT DOCUMENTS

| | | |
|---|---|---|
| CN | 1563076 | 1/2005 |
| CN | 1709906 | 12/2005 |
| CN | 1010302246 | 11/2008 |
| WO | WO 92/00995 | 1/1992 |
| WO | WO 94/22460 | 10/1994 |
| WO | WO 97/40070 | 10/1997 |
| WO | WO 98/10068 | 3/1998 |
| WO | WO 98/27113 | 6/1998 |
| WO | WO 99/21571 | 5/1999 |
| WO | WO 99/54358 | 10/1999 |
| WO | WO 00/01730 | 1/2000 |
| WO | WO 00/05263 | 2/2000 |
| WO | WO 00/35952 | 6/2000 |
| WO | WO 00/58361 | 10/2000 |
| WO | WO 01/00224 | 1/2001 |
| WO | WO 01/30808 | 5/2001 |
| WO | WO 01/52880 | 7/2001 |
| WO | WO 01/74844 | 10/2001 |
| WO | WO 01/85930 | 11/2001 |
| WO | WO 01/90140 | 11/2001 |
| WO | WO 02/18437 | 3/2002 |
| WO | WO 02/26774 | 4/2002 |
| WO | WO 02/094873 | 11/2002 |
| WO | WO 03/006604 | 1/2003 |
| WO | WO 03/006620 | 1/2003 |
| WO | WO 03/095474 | 11/2003 |
| WO | WO 2004/005324 | 1/2004 |
| WO | WO 2004/046166 | 6/2004 |
| WO | WO 2004/099246 | 11/2004 |
| WO | WO 2005/000338 | 1/2005 |
| WO | WO 2005/000339 | 1/2005 |
| WO | WO 2005/000877 | 1/2005 |
| WO | WO 2005/014617 | 2/2005 |
| WO | WO 2005/030797 | 4/2005 |
| WO | WO 2005/048967 | 6/2005 |
| WO | WO 2005/060985 | 7/2005 |
| WO | WO 2005/102377 | 11/2005 |
| WO | WO 2006/012667 | 2/2006 |
| WO | WO 2006/014552 | 2/2006 |
| WO | WO 2006/032457 | 3/2006 |
| WO | WO 2006/037188 | 4/2006 |
| WO | WO 2006/048449 | 5/2006 |
| WO | WO 2006/048450 | 5/2006 |
| WO | WO 2006/048451 | 5/2006 |
| WO | WO 2006/048452 | 5/2006 |
| WO | WO 2006/060873 | 6/2006 |
| WO | WO 2006/073771 | 7/2006 |
| WO | WO 2006/076442 | 7/2006 |
| WO | WO 2006/097526 | 9/2006 |
| WO | WO 2006/129317 | 12/2006 |
| WO | WO 2007/008684 | 1/2007 |
| WO | WO 2007/008704 | 1/2007 |
| WO | WO 2007/009894 | 1/2007 |
| WO | WO 2007/027574 | 3/2007 |
| WO | WO 2007/035474 | 3/2007 |
| WO | WO 2008/056207 | 5/2008 |
| WO | WO 2008/087186 | 7/2008 |
| WO | WO 2008/087187 | 7/2008 |
| WO | WO 2008/087188 | 7/2008 |
| WO | WO 2008/087189 | 7/2008 |
| WO | WO 2008/087190 | 7/2008 |
| WO | WO 2008/142319 | 11/2008 |
| WO | WO 2008/156677 | 12/2008 |
| WO | WO 2009/151383 | 12/2009 |
| WO | WO 2009/152079 | 12/2009 |
| WO | WO 2010/144341 | 12/2010 |
| WO | WO 2010/144344 | 12/2010 |

OTHER PUBLICATIONS

Bednarek et al., "Analogs of lactam derivatives of alpha-melanotropin with basic and acidic residues," Biochem. Biophys. Res. Commun., 2000, 272(1): 23-28.

Bednarek et al., "Analogs of MTII, Lactam Derivatives of a-Melanotropin, Modified at the N-Terminus, and Their Selectivity at Human Melanocortin Receptors 3, 4, and 5," Biochemical and Biophysical Research Communications, 1999, 261: 209-213.

Bednarek et al., "Cyclic analogs of alpha-melanocyte-stimulating hormone (alphaMSH) with high agonist potency and selectivity at human melanocortin receptor 1b," Peptides, 2008, 29(6):1010-1017.

Bednarek et al., "Ligands of the melanocortin receptors, 2002-2003 update," Expert Opin. Ther. Patents, 2004, 14(3): 327-336.

Chan et al., "Molecular modelling of beta turns in a cyclic melanotropin," J. Pharm. Pharmacol., 1996, 48(2): 218-222.

Gautron et al., "Melanocortin-4 receptor expression in a vago-vagal circuitry involved in postprandial functions," J. Comp. Neurol., 2010, 518(1): 6-24.

Giuliani et al., "Selective melanocortin MC4 receptor agonists reverse haemorrhagic shock and prevent multiple organ damage," Br. J. Pharmacol., 2007, 150(5): 595-603.

Grieco et al., "Structure-activity studies of new melanocortin peptides containing an aromatic amino acid at the N-terminal position," Peptides, 2006, 27(2): 472-481.

(56) References Cited

OTHER PUBLICATIONS

Hadley, "The Proopiomelanocortin System," Annals New York Academy of Science, 1999, 885: 1-21.

Hruby et al., "A highly potent cyclic a-MSH antagonist containing naphthylalanine," Peptides: Chemistry, Structure and Biology, Proceedings of the American Peptide Symposium, 14th, Columbus, Ohio, Jun. 18-23, 1996, 364-365.

Hruby et al., "Cyclic lactam alpha-melanotropin analogues of Ac-Nle4-cyclo[Asp5,D-Phe7,Lys10] alpha-melanocyte-stimulating hormone-(4-10)-NH2 with bulky aromatic amino acids at position 7 show high antagonist potency and selectivity at specific melanocortin receptors," J. Med. Chem., 1995, 38(18):3454-3461.

Hruby et al., "Design of potent and specific melanotropin agonists and antagonists: investigating ligands for new receptors," Peptides, 1996, Proceedings of the European Peptide Symposium, 24th, Edinburgh, Sep. 8-13, 1996(1998), 485-486.

Maaser et al., "Role of the melanocortin system in inflammation," Ann. New York Acad. Sci., 2006, 1072: 123-134.

Navarro et al., "Effects of melanocortin receptor activation and blockade on ethanol intake: a possible role for the melanocortin-4 receptor," Alcohol Clin. Exp. Res., 2005, 29(6):949-957.

Nigenhuis et al., "Accelerating sensory recovery after sciatic nerve crush: non-selective versus melanocortin MC4 receptor-selective peptides," European Journal of Pharmacology, 2004, 495, 145-152.

Nigenhuis et al., "Discovery and in vivo evaluation of new melanocortin-4 receptor-selective peptides," Peptides, 2003, 24: 271-280.

Nogueiras et al., "The central melanocortin system directly controls peripheral lipid metabolism," J. Clin. Invest., 2007, 117(11): 3475-3488.

Nozawa et al., "Recent advances in the development of melanocortin-4 receptor ligands," Expert Opin. Ther. Patents, 2008, 18(4): 403-427.

Oosterom et al., "Common Requirements for Melanocortin-4 Receptor Selectivity of Structurally Unrelated Melanocortin Agonist and Endogenous Antagonist, Agouti Protein," J. Bio. Chem., 2001, 276(2): 931-936.

Schaaper et al., "Synthesis of cyclic alpha-MSH peptides," Letters in Peptide Science, 1998, 5(2-3): 205-208.

Todorovic et al., "A review of melanocortin receptor small molecule ligands," Peptides, 2005, 26(10): 2026-2036.

Ujjainwalla et al., "Small molecule ligands of the human melanocortin-4 receptor," Curr Top Med Chem., 2007, 7(11), 1068-1084.

Vrinten et al., "Antagonism of the Melanocortin System Reduces Cold and Mechanical Allodynia in Mononeuropathic Rats," J. Neurosci., 2000, 20(21): 8131-8137.

Wikberg et al., "Targeting melanocortin receptors: an approach to treat weight disorders and sexual dysfunction," Nat. Rev. Drug Discov., 2008, 7(4): 307-323.

Yan et al., "Structure-activity relationships of beta-MSH derived melanocortin-4 receptor peptide agonists," Curr. Top. Med. Chem., 2007, 7(11): 1052-1067.

International Search Report issued in International Patent Application No. PCT/US2009/046571 dated Nov. 3, 2009.

Written Opinion issued in International Patent Application No. PCT/US2009/046571 dated Nov. 3, 2009.

International Search Report issued in International Patent Application No. PCT/US2010/037589 dated Oct. 14, 2010.

International Search Report and Written Opinion issued in PCT application No. PCT/SE2010/050626 (Sep. 2010).

Written Opinion issued in International Patent Application No. PCT/US2010/037589 dated Oct. 14, 2010.

Supplementary European Search Report issued in European Patent Application No. EP09763370.5 dated Dec. 19, 2011.

Search report issued by the Swedish Patent and Registration Office dated Dec. 9, 2009.

* cited by examiner

```
                              SEQUENCE LISTING

<160> NUMBER OF SEQ ID NOS: 122

<210> SEQ ID NO 1
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (2)..(7)
<223> OTHER INFORMATION: cyclic peptide lactam bond
<220> FEATURE:
<221> NAME/KEY: MISC_FEATURE
<222> LOCATION: (4)..(4)
<223> OTHER INFORMATION: D-Phe
<220> FEATURE:
<221> NAME/KEY: MOD_RES
<222> LOCATION: (7)..(7)
<223> OTHER INFORMATION: AMIDATION

<400> SEQUENCE: 1

Xaa Asp His Xaa Arg Trp Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (2)..(7)
<223> OTHER INFORMATION: cyclic peptide lactam bond
<220> FEATURE:
<221> NAME/KEY: MISC_FEATURE
<222> LOCATION: (4)..(4)
<223> OTHER INFORMATION: D-Phe

<400> SEQUENCE: 2

Xaa Asp His Xaa Arg Trp Lys
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic melanocortin receptor binding core
      sequence derived from alpha-MSH
```

<400> SEQUENCE: 3

His Phe Arg Trp
1

<210> SEQ ID NO 4
<211> LENGTH: 13
<212> TYPE: PRT
<213> ORGANISM: Artificial Sequence
<220> FEATURE:
<223> OTHER INFORMATION: Human alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (13)..(13)
<223> OTHER INFORMATION: AMIDATION

<400> SEQUENCE: 4

Ser Tyr Ser Met Glu His Phe Arg Trp Gly Lys Pro Val
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic melanocortin binding sequence derived
      from human alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MISC_FEATURE
<222> LOCATION: (7)..(7)
<223> OTHER INFORMATION: D-Phe
<220> FEATURE:
<221> NAME/KEY: MOD_RES
<222> LOCATION: (13)..(13)
<223> OTHER INFORMATION: AMIDATION

<400> SEQUENCE: 5

Ser Tyr Ser Xaa Glu His Xaa Arg Trp Gly Lys Pro Val
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE -continued

```
<222> LOCATION: (4)..(4)
<223> OTHER INFORMATION: D-Phe(2-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 6

Arg Glu Xaa Xaa Arg Trp Xaa
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(3-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 7

Arg Glu Xaa Xaa Arg Trp Xaa
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(4-Cl)
<220> FEATURE:
```

```
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 8

Arg Glu Xaa Xaa Arg Trp Xaa
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(2,4-diCl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 9

Arg Glu Xaa Xaa Arg Trp Xaa
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(3,4-diCl)
<220> FEATURE:
<221> NAME/KEY: MOD_RES
<222> LOCATION: (7)..(7)
<223> OTHER INFORMATION: Orn
```

```
<220> FEATURE:
<221> NAME/KEY: MOD_RES
<222> LOCATION: (7)..(7)
<223> OTHER INFORMATION: AMIDATION

<400> SEQUENCE: 10

Arg Glu Xaa Xaa Arg Trp Xaa
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(3-CN)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 11

Arg Glu Xaa Xaa Arg Trp Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
```

<223> OTHER INFORMATION: AMIDATION

<400> SEQUENCE: 12

Arg Glu Xaa Xaa Arg Trp Xaa
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Tyr
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 13

Arg Glu Xaa Xaa Arg Trp Xaa
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(2-F)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 14

```
Arg Glu Xaa Xaa Arg Trp Xaa
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(3-F)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 15

Arg Glu Xaa Xaa Arg Trp Xaa
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(4-F)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 16

Arg Glu Xaa Xaa Arg Trp Xaa
1               5
```

-continued

```
<210> SEQ ID NO 17
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(2-CN)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 17

Arg Glu Xaa Xaa Arg Trp Xaa
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(2-CF3)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 18

Arg Glu Xaa Xaa Arg Trp Xaa
1               5

<210> SEQ ID NO 19
```

```
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(3-CF3)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 19

Arg Glu Xaa Xaa Arg Trp Xaa
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(4-Me)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 20

Arg Glu Xaa Xaa Arg Trp Xaa
1               5

<210> SEQ ID NO 21
<211> LENGTH: 7
<212> TYPE: PRT
<213> ORGANISM: Artificial Sequence
```

```
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(4-OMe)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 21

Arg Glu Xaa Xaa Arg Trp Xaa
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(3,5-diF)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 22

Arg Glu Xaa Xaa Arg Trp Xaa
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(2-Me)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 23

Arg Glu Xaa Xaa Arg Trp Xaa
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(3-Me)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 24

Arg Glu Xaa Xaa Arg Trp Xaa
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(4-CF3)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 25

Arg Glu Xaa Xaa Arg Trp Xaa
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(2,4-diMe)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 26

Arg Glu Xaa Xaa Arg Trp Xaa
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
```

-continued

```
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(2-NO2)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 27

Arg Glu Xaa Xaa Arg Trp Xaa
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(3-NO2)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 28

Arg Glu Xaa Xaa Arg Trp Xaa
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
```

```
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(4-NO2)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 29

Arg Glu Xaa Xaa Arg Trp Xaa
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(3,4-diOMe)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 30

Arg Glu Xaa Xaa Arg Trp Xaa
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
```

```
<220> FEATURE:
<221> NAME/KEY: MISC_FEATURE
<222> LOCATION: (4)..(4)
<223> OTHER INFORMATION: D-Phe(3,4-diF)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 31

Arg Glu Xaa Xaa Arg Trp Xaa
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(3,4,5-triF)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 32

Arg Glu Xaa Xaa Arg Trp Xaa
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
```

```
<223> OTHER INFORMATION: D-Phe(4-NH2)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 33

Arg Glu Xaa Xaa Arg Trp Xaa
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(4-Ph)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 34

Arg Glu Xaa Xaa Arg Trp Xaa
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(4-tBu)
<220> FEATURE:
<221> NAME/KEY: MOD_RES
```

```
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 35

Arg Glu Xaa Xaa Arg Trp Xaa
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 36

Arg Glu Ser Xaa Arg Trp Xaa
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 37

Arg Glu Thr Xaa Arg Trp Xaa
1               5
```

```
<210> SEQ ID NO 38
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Hyp
<220> FEATURE:
<221> NAME/KEY: MISC_FEATURE
<222> LOCATION: (4)..(4)
<223> OTHER INFORMATION: D-Phe(2-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 38

Arg Glu Xaa Xaa Arg Trp Xaa
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 39

Arg Glu Gln Xaa Arg Trp Xaa
1               5

<210> SEQ ID NO 40
<211> LENGTH: 7
<212> TYPE: PRT
<213> ORGANISM: Artificial Sequence
<220> FEATURE:
```

```
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(3-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 40

Arg Glu Ser Xaa Arg Trp Xaa
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(3-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 41

Arg Glu Thr Xaa Arg Trp Xaa
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
```

<220> FEATURE:
<221> NAME/KEY: MISC_FEATURE
<222> LOCATION: (3)..(3)
<223> OTHER INFORMATION: Hyp
<220> FEATURE:
<221> NAME/KEY: MISC_FEATURE
<222> LOCATION: (4)..(4)
<223> OTHER INFORMATION: D-Phe(3-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 42

Arg Glu Xaa Xaa Arg Trp Xaa
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(3-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 43

Arg Glu Gln Xaa Arg Trp Xaa
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: Orn

```
<220> FEATURE:
<221> NAME/KEY: MOD_RES
<222> LOCATION: (7)..(7)
<223> OTHER INFORMATION: AMIDATION

<400> SEQUENCE: 44

Arg Glu Pro Xaa Arg Trp Xaa
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Hyp
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 45

Arg Glu Xaa Xaa Arg Trp Xaa
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 46
```

Arg Glu Ala Xaa Arg Trp Xaa
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 47

Arg Glu Val Xaa Arg Trp Xaa
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 48

Arg Glu Asn Xaa Arg Trp Xaa
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 49

Arg Glu Thr Xaa Arg Trp Xaa
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 50

Arg Glu Ser Xaa Arg Trp Xaa
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
```

```
<223> OTHER INFORMATION: D-Phe(4-CN)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 51

Arg Glu Gln Xaa Arg Trp Xaa
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Ser(Bzl)
<220> FEATURE:
<221> NAME/KEY: MISC_FEATURE
<222> LOCATION: (4)..(4)
<223> OTHER INFORMATION: D-Phe(2-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 52

Arg Glu Xaa Xaa Arg Trp Xaa
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(8)
<223> OTHER INFORMATION: cyclized
<220> FEATURE:
<221> NAME/KEY: MISC_FEATURE
<222> LOCATION: (3)..(3)
<223> OTHER INFORMATION: Phe(3-C(=O)-NH2)
<220> FEATURE:
<221> NAME/KEY: MISC_FEATURE
<222> LOCATION: (4)..(4)
<223> OTHER INFORMATION: D-Phe(2-Cl)
<220> FEATURE:
<221> NAME/KEY: MISC_FEATURE
```

```
<222> LOCATION: (5)..(5)
<223> OTHER INFORMATION: D-Phe
<220> FEATURE:
<221> NAME/KEY: MOD_RES
<222> LOCATION: (8)..(8)
<223> OTHER INFORMATION: Orn
<220> FEATURE:
<221> NAME/KEY: MOD_RES
<222> LOCATION: (8)..(8)
<223> OTHER INFORMATION: AMIDATION

<400> SEQUENCE: 53

Arg Glu Xaa Xaa Xaa Arg Trp Xaa
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MOD_RES
<222> LOCATION: (3)..(3)
<223> OTHER INFORMATION: Orn
<220> FEATURE:
<221> NAME/KEY: MISC_FEATURE
<222> LOCATION: (4)..(4)
<223> OTHER INFORMATION: D-Phe(2-Cl)
<220> FEATURE:
<221> NAME/KEY: MOD_RES
<222> LOCATION: (7)..(7)
<223> OTHER INFORMATION: Orn

<400> SEQUENCE: 54

Arg Glu Xaa Xaa Arg Trp Xaa
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-Cl)
<220> FEATURE:
```

```
<221> NAME/KEY: MOD_RES
<222> LOCATION: (7)..(7)
<223> OTHER INFORMATION: AMIDATION

<400> SEQUENCE: 55

Xaa Xaa His Xaa Arg Trp Glu
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(3-Cl)
<220> FEATURE:
<221> NAME/KEY: MOD_RES
<222> LOCATION: (7)..(7)
<223> OTHER INFORMATION: AMIDATION

<400> SEQUENCE: 56

Xaa Xaa His Xaa Arg Trp Glu
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: AMIDATION
```

<400> SEQUENCE: 57

Xaa Xaa His Xaa Arg Trp Glu
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-F)
<220> FEATURE:
<221> NAME/KEY: MOD_RES
<222> LOCATION: (7)..(7)
<223> OTHER INFORMATION: AMIDATION

<400> SEQUENCE: 58

Xaa Xaa His Xaa Arg Trp Glu
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(3,4-diF)
<220> FEATURE:
<221> NAME/KEY: MOD_RES
<222> LOCATION: (7)..(7)
<223> OTHER INFORMATION: AMIDATION

<400> SEQUENCE: 59

Xaa Xaa His Xaa Arg Trp Glu
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MOD_RES
<222> LOCATION: (3)..(3)
<223> OTHER INFORMATION: Orn
<220> FEATURE:
<221> NAME/KEY: MISC_FEATURE
<222> LOCATION: (4)..(4)
<223> OTHER INFORMATION: D-Phe(3-Cl)
<220> FEATURE:
<221> NAME/KEY: MOD_RES
<222> LOCATION: (7)..(7)
<223> OTHER INFORMATION: Orn

<400> SEQUENCE: 60

Arg Glu Xaa Xaa Arg Trp Xaa
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab(Acetyl)
<220> FEATURE:
<221> NAME/KEY: MISC_FEATURE
<222> LOCATION: (4)..(4)
<223> OTHER INFORMATION: D-Phe(2-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 61

Arg Glu Xaa Xaa Arg Trp Xaa
1               5

<210> SEQ ID NO 62
<211> LENGTH: 7
<212> TYPE: PRT

```
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-F)
<220> FEATURE:
<221> NAME/KEY: MOD_RES
<222> LOCATION: (7)..(7)
<223> OTHER INFORMATION: AMIDATION

<400> SEQUENCE: 62

Xaa Xaa His Xaa Arg Trp Glu
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-F)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 63

Arg Glu Ser Xaa Arg Trp Xaa
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-F)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 64

Arg Glu Gln Xaa Arg Trp Xaa
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Hyp
<220> FEATURE:
<221> NAME/KEY: MISC_FEATURE
<222> LOCATION: (4)..(4)
<223> OTHER INFORMATION: D-Phe(4-F)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 65

Arg Glu Xaa Xaa Arg Trp Xaa
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
```

-continued

```
<222> LOCATION: (3)..(3)
<223> OTHER INFORMATION: Dap
<220> FEATURE:
<221> NAME/KEY: MISC_FEATURE
<222> LOCATION: (4)..(4)
<223> OTHER INFORMATION: D-Phe(3-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 66

Arg Glu Xaa Xaa Arg Trp Xaa
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dap
<220> FEATURE:
<221> NAME/KEY: MISC_FEATURE
<222> LOCATION: (4)..(4)
<223> OTHER INFORMATION: D-Phe(2-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 67

Arg Glu Xaa Xaa Arg Trp Xaa
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Thr(Bzl)
<220> FEATURE:
```

```
<221> NAME/KEY: MISC_FEATURE
<222> LOCATION: (4)..(4)
<223> OTHER INFORMATION: D-Phe(2-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 68

Arg Glu Xaa Xaa Arg Trp Xaa
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Hyp
<220> FEATURE:
<221> NAME/KEY: MISC_FEATURE
<222> LOCATION: (4)..(4)
<223> OTHER INFORMATION: D-Phe(2-F)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 69

Arg Glu Xaa Xaa Arg Trp Xaa
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-F)
<220> FEATURE:
<221> NAME/KEY: MOD_RES
<222> LOCATION: (7)..(7)
<223> OTHER INFORMATION: Orn
```

```
-continued

<220> FEATURE:
<221> NAME/KEY: MOD_RES
<222> LOCATION: (7)..(7)
<223> OTHER INFORMATION: AMIDATION

<400> SEQUENCE: 70

Arg Glu Ser Xaa Arg Trp Xaa
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-F)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 71

Arg Glu Pro Xaa Arg Trp Xaa
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-F)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 72

Arg Glu Pro Xaa Arg Trp Xaa
1               5
```

```
<210> SEQ ID NO 73
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Met(O2)
<220> FEATURE:
<221> NAME/KEY: MISC_FEATURE
<222> LOCATION: (4)..(4)
<223> OTHER INFORMATION: D-Phe(4-F)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 73

Arg Glu Xaa Xaa Arg Trp Xaa
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-F)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 74

Arg Glu Asn Xaa Arg Trp Xaa
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
```

<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-F)
<220> FEATURE:
<221> NAME/KEY: MOD_RES
<222> LOCATION: (7)..(7)
<223> OTHER INFORMATION: AMIDATION

<400> SEQUENCE: 75

Arg Xaa Asn Xaa Arg Trp Glu
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic melanocortin binding peptide derived from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-F)
<220> FEATURE:
<221> NAME/KEY: MOD_RES
<222> LOCATION: (7)..(7)
<223> OTHER INFORMATION: AMIDATION

<400> SEQUENCE: 76

Arg Xaa Asn Xaa Arg Trp Glu
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic melanocortin binding peptide derived from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)

```
<223> OTHER INFORMATION: cyclized
<220> FEATURE:
<221> NAME/KEY: MISC_FEATURE
<222> LOCATION: (4)..(4)
<223> OTHER INFORMATION: D-Phe(3-Me)
<220> FEATURE:
<221> NAME/KEY: MOD_RES
<222> LOCATION: (7)..(7)
<223> OTHER INFORMATION: AMIDATION

<400> SEQUENCE: 77

Arg Xaa Asn Xaa Arg Trp Glu
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-Me)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 78

Arg Glu Asn Xaa Arg Trp Xaa
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-Me)
<220> FEATURE:
<221> NAME/KEY: MOD_RES
<222> LOCATION: (7)..(7)
<223> OTHER INFORMATION: AMIDATION

<400> SEQUENCE: 79
```

-continued

```
Arg Xaa Asn Xaa Arg Trp Glu
1               5

<210> SEQ ID NO 80
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(3,4-diF)
<220> FEATURE:
<221> NAME/KEY: MOD_RES
<222> LOCATION: (7)..(7)
<223> OTHER INFORMATION: AMIDATION

<400> SEQUENCE: 80

Arg Xaa Asn Xaa Arg Trp Glu
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(3,5-diF)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 81

Arg Glu Asn Xaa Arg Trp Xaa
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic melanocortin binding peptide derived
```

```
                    from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(3,5-diF)
<220> FEATURE:
<221> NAME/KEY: MOD_RES
<222> LOCATION: (7)..(7)
<223> OTHER INFORMATION: AMIDATION

<400> SEQUENCE: 82

Arg Xaa Asn Xaa Arg Trp Glu
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic melanocortin binding peptide derived
                    from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(3,4-diF)
<220> FEATURE:
<221> NAME/KEY: MOD_RES
<222> LOCATION: (7)..(7)
<223> OTHER INFORMATION: AMIDATION

<400> SEQUENCE: 83

Xaa Asp Gln Xaa Arg Trp Lys
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic melanocortin binding peptide derived
                    from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
```

```
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-Cl)
<220> FEATURE:
<221> NAME/KEY: MOD_RES
<222> LOCATION: (7)..(7)
<223> OTHER INFORMATION: AMIDATION

<400> SEQUENCE: 84

Xaa Asp Gln Xaa Arg Trp Lys
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(3-Cl)
<220> FEATURE:
<221> NAME/KEY: MOD_RES
<222> LOCATION: (7)..(7)
<223> OTHER INFORMATION: AMIDATION

<400> SEQUENCE: 85

Xaa Asp Gln Xaa Arg Trp Lys
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: AMIDATION
```

```
<400> SEQUENCE: 86

Xaa Asp Gln Xaa Arg Trp Lys
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-F)
<220> FEATURE:
<221> NAME/KEY: MOD_RES
<222> LOCATION: (7)..(7)
<223> OTHER INFORMATION: AMIDATION

<400> SEQUENCE: 87

Xaa Asp Gln Xaa Arg Trp Lys
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: D-Arg
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-F)
<220> FEATURE:
<221> NAME/KEY: MOD_RES
<222> LOCATION: (7)..(7)
<223> OTHER INFORMATION: AMIDATION

<400> SEQUENCE: 88

Xaa Asp Gln Xaa Arg Trp Lys
1               5

<210> SEQ ID NO 89
<211> LENGTH: 7
<212> TYPE: PRT
<213> ORGANISM: Artificial Sequence
<220> FEATURE:
```

```
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 89

Arg Glu Asn Xaa Arg Trp Xaa
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: Orn

<400> SEQUENCE: 90

Arg Glu Asn Xaa Arg Trp Xaa
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
```

```
<221> NAME/KEY: MOD_RES
<222> LOCATION: (7)..(7)
<223> OTHER INFORMATION: Orn

<400> SEQUENCE: 91

Arg Glu Gln Xaa Arg Trp Xaa
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (4)..(4)
<223> OTHER INFORMATION: D-Phe(3-OMe)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 92

Arg Glu Xaa Xaa Arg Trp Xaa
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 93

Arg Glu Pro Xaa Arg Trp Xaa
```

```
<210> SEQ ID NO 94
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: AMIDATION

<400> SEQUENCE: 94

Arg Asp Asn Xaa Arg Trp Lys
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: AMIDATION

<400> SEQUENCE: 95

Arg Asp Gln Xaa Arg Trp Lys
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Orn
<220> FEATURE:
```

```
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: AMIDATION

<400> SEQUENCE: 96

Arg Xaa Asn Xaa Arg Trp Glu
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-F)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 97

Arg Glu Gln Xaa Arg Trp Xaa
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: AMIDATION

<400> SEQUENCE: 98

Arg Lys Gln Xaa Arg Trp Asp
```

```
<210> SEQ ID NO 99
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: AMIDATION

<400> SEQUENCE: 99

Arg Xaa Gln Xaa Arg Trp Glu
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(3,4,5-triF)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 100

Arg Glu Asn Xaa Arg Trp Xaa
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(3,4,5-triF)
<220> FEATURE:
<221> NAME/KEY: MOD_RES
<222> LOCATION: (7)..(7)
<223> OTHER INFORMATION: AMIDATION

<400> SEQUENCE: 101

Arg Xaa Asn Xaa Arg Trp Glu
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(3,4,5-triF)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 102

Arg Glu Gln Xaa Arg Trp Xaa
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
```

```
<220> FEATURE:
<221> NAME/KEY: MISC_FEATURE
<222> LOCATION: (4)..(4)
<223> OTHER INFORMATION: D-Phe(3,4,5-triF)
<220> FEATURE:
<221> NAME/KEY: MOD_RES
<222> LOCATION: (7)..(7)
<223> OTHER INFORMATION: AMIDATION

<400> SEQUENCE: 103

Arg Xaa Gln Xaa Arg Trp Glu
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(3-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 104

Arg Glu Arg Xaa Arg Trp Xaa
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(3-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 105
```

```
Arg Glu Lys Xaa Arg Trp Xaa
1               5
```

<210> SEQ ID NO 106
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MOD_RES
<222> LOCATION: (3)..(3)
<223> OTHER INFORMATION: Orn
<220> FEATURE:
<221> NAME/KEY: MISC_FEATURE
<222> LOCATION: (4)..(4)
<223> OTHER INFORMATION: D-Phe(3-Cl)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 106

```
Arg Glu Xaa Xaa Arg Trp Xaa
1               5
```

<210> SEQ ID NO 107
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-F)
<220> FEATURE:
<221> NAME/KEY: MOD_RES
<222> LOCATION: (7)..(7)
<223> OTHER INFORMATION: Orn

<400> SEQUENCE: 107

```
Arg Glu Pro Xaa Arg Trp Xaa
1               5
```

<210> SEQ ID NO 108
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-F)
<220> FEATURE:
<221> NAME/KEY: MOD_RES
<222> LOCATION: (7)..(7)
<223> OTHER INFORMATION: AMIDATION

<400> SEQUENCE: 108

Arg Asp Pro Xaa Arg Trp Lys
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-F)
<220> FEATURE:
<221> NAME/KEY: MOD_RES
<222> LOCATION: (7)..(7)
<223> OTHER INFORMATION: AMIDATION

<400> SEQUENCE: 109

Arg Asp Pro Xaa Arg Trp Lys
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-F)
<220> FEATURE:
<221> NAME/KEY: MOD_RES
<222> LOCATION: (7)..(7)
```

```
<223> OTHER INFORMATION: AMIDATION

<400> SEQUENCE: 110

Arg Xaa Pro Xaa Arg Trp Glu
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 111

Arg Glu Asp Xaa Arg Trp Xaa
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: Orn

<400> SEQUENCE: 112

Arg Glu Asp Xaa Arg Trp Xaa
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 113

Arg Glu Glu Xaa Arg Trp Xaa
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(4-CN)
<220> FEATURE:
<221> NAME/KEY: MOD_RES
<222> LOCATION: (7)..(7)
<223> OTHER INFORMATION: Orn

<400> SEQUENCE: 114

Arg Glu Glu Xaa Arg Trp Xaa
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-Me)
<220> FEATURE:
<221> NAME/KEY: MOD_RES
<222> LOCATION: (7)..(7)
```

```
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 115

Arg Glu Gln Xaa Arg Trp Xaa
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-Me)
<220> FEATURE:
<221> NAME/KEY: MOD_RES
<222> LOCATION: (7)..(7)
<223> OTHER INFORMATION: AMIDATION

<400> SEQUENCE: 116

Arg Xaa Gln Xaa Arg Trp Glu
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-Cl)
<220> FEATURE:
<221> NAME/KEY: MOD_RES
<222> LOCATION: (7)..(7)
<223> OTHER INFORMATION: AMIDATION

<400> SEQUENCE: 117

Arg Xaa Gln Xaa Arg Trp Glu
1               5
```

```
<210> SEQ ID NO 118
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-Cl)
<220> FEATURE:
<221> NAME/KEY: MOD_RES
<222> LOCATION: (7)..(7)
<223> OTHER INFORMATION: AMIDATION

<400> SEQUENCE: 118

Arg Xaa Asn Xaa Arg Trp Glu
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: cyclized
<220> FEATURE:
<221> NAME/KEY: MISC_FEATURE
<222> LOCATION: (4)..(4)
<223> OTHER INFORMATION: D-Phe(2-CF3)
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (7)..(7)
<223> OTHER INFORMATION: AMIDATION

<400> SEQUENCE: 119

Arg Glu Gln Xaa Arg Trp Xaa
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic melanocortin binding peptide derived
      from human NDP-alpha-MSH
<220> FEATURE:
<221> NAME/KEY: MOD_RES
<222> LOCATION: (1)..(1)
```

<223> OTHER INFORMATION: ACETYLATION
<220> FEATURE:
<221> NAME/KEY: MOD_RES
<222> LOCATION: (2)..(2)
<223> OTHER INFORMATION: Orn

```
<222> LOCATION: (4)..(4)
<223> OTHER INFORMATION: D-Phe(2-CF3)
<220> FEATURE:
<221> NAME/KEY: MOD_RES
<222> LOCATION: (7)..(7)
<223> OTHER INFORMATION: AMIDATION

<400> SEQUENCE: 122

Arg Xaa Asn Xaa Arg Trp Glu
1               5
```

MELANOCORTIN RECEPTOR-SPECIFIC PEPTIDES

SEQUENCE LISTING SUBMISSION VIA EFS-WEB

A computer readable text file, entitled "SequenceListing.txt," created on or about Jun. 7, 2010 with a file size of about 68 kb contains the sequence listing for this application and is hereby incorporated by reference in its entirety.

TECHNICAL FIELD

The present invention relates to melanocortin receptor-specific cyclic peptides which may be used in the treatment of melanocortin receptor-mediated diseases, indications, conditions and syndromes, in particular energy homeostasis and metabolism related (e.g. diabetes), food intake related and/or energy balance and body weight related diseases, disorders and/or conditions, including obesity, overweight and diseases, disorders and/or conditions associated with obesity and/or overweight, such as type 2 diabetes and metabolic syndrome.

BACKGROUND

The following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, midbrain and brainstem, and melanocortin-5 receptors (MC5-R), expressed in a wide distribution of peripheral tissues. MC1-R has been suggested to be associated with hair and skin pigmentation and inflammation, MC2-R is believed to mediate steroidogenesis, MC3-R has been suggested to be associated with energy homeostasis, food intake, and inflammation, MC4-R is believed to control feeding behavior, energy homeostasis, and sexual function (e.g. erectile function), and MC5-R has been suggested to be involved in the exocrine gland system.

Significant work has been done in determining the structure of melanocortin receptors, including both the nucleic acid sequences encoding for the receptors and the amino acid sequences constituting the receptors. MC4-R is a G protein-coupled, 7-transmembrane receptor that is believed to be expressed primarily in the brain.

MC4-R inactivation has been shown to result in obesity (Hadley, 1999, Ann NY Acad. Sci., 885:1-21). Agouti-related protein (AgRP) is an endogenous compound that has been suggested to be a MC antagonist or an inverse agonist on MC4-R. The α-melanocyte stimulating hormone (α-MSH) is believed to be the principle endogenous MC4-R agonist.

Also peripherally located MC4-R receptors have been suggested to be involved in the control of energy homeostasis, and the role of MC4-R signalling in the vagus nerve and its relevance for treatment of obesity and diabetes is discussed by Gautron et al, The Journal of Comparative Neurology, 518:6-24 (2010).

Peptides specific for MC4-R, and secondarily peptides specific for MC3-R, are believed to be useful in regulation of mammalian energy homeostasis, including use as agents for attenuating food intake and body weight gain. MC4-R agonist peptides are believed to be useful for treating sexual dysfunction, including male erectile dysfunction, and for decreasing food intake and body weight gain, such as for treatment of obesity. Such peptides may also be employed for decreasing voluntary ethanol consumption, treatment of drug addictions, and the like. MC4-R agonist peptides, as well as MC3-R agonist peptides, may further be employed for treatment of circulatory shock, ischemia, hemorrhagic shock, inflammatory diseases and related diseases, indications, conditions and syndromes. MC4-R antagonist peptides, by contrast, are believed to be useful for weight gain aid, such as for use in treatment of cachexia, sarcopenia, wasting syndrome or disease, and anorexia. Such peptides may also be employed for treatment of depression and related disorders. (Wikberg et al, Nature Reviews, Drug Discovery, 7, 307, (2008); Adan et al, British J. Pharm., 149, 815-827 (2006); Nogueiras et al, J. Clin., Invest., 117(11): 3475-3488 (2007); Maaser et al, Ann. N.Y. Acad. Sci., 1072, 123-134 (2006); Giuliani et al, British J. Pharm., 150, 595-603 (2007); Balbani, Expert Opin. Ther. Patents, 17(3), 287-297 (2007); and Navarro et al, Alcohol. Clin. Exp. Res., 29(6), 949-957 (2005)). Melanocortin receptor-specific peptides include cyclic α-MSH analog peptides such as Ac-Nle-cyclo(-Asp-His-D-Phe-Arg-Trp-Lys)-NH$_2$ (SEQ ID NO:1) (See U.S. Pat. Nos. 5,674,839 and 5,576,290) and Ac-Nle-cyclo(-Asp-His-D-Phe-Arg-Trp-Lys)-OH (SEQ ID NO:2) (See U.S. Pat. Nos. 6,579,968 and 6,794,489). These and other melanocortin receptor-specific peptides generally contain the central tetrapeptide sequence of native α-MSH, His$^6$-Phe$^7$-Arg$^8$-Trp$^9$ (SEQ ID NO:3), or a mimetic or variation thereof, including the substitution of D-Phe for Phe$^7$. Other peptides or peptide-like compounds asserted to be specific for one or more melanocortin receptors are disclosed in U.S. Pat. Nos. 5,731,408, 6,054,556, 6,350,430, 6,476,187, 6,600,015, 6,613,874, 6,693,165, 6,699,873, 6,887,846, 6,951,916, 7,008,925, and 7,176,279; in U.S. published patent application Publication Nos. 2001/0056179, 2002/0143141, 2003/0064921, 2003/0105024, 2003/0212002, 2004/0023859, 2005/0130901, 2005/0187164, 2005/0239711, 2006/0105951, 2006/0111281, 2006/0293223, 2007/0027091, 2007/0105759, 2007/0123453, 2007/0244054, and 2008/0039387; and in international patent applications nos. WO 98/27113, WO 99/21571, WO 00/05263, WO 99/54358, WO 00/35952, WO 00/58361, WO 01/30808, WO 01/52880, WO 01/74844, WO 01/85930, WO 01/90140, WO 02/18437, WO 02/26774, WO 03/006604, WO 2004/099246, WO 2004/046166, WO 2005/000338, WO 2005/000339, WO 2005/000877, WO 2005/030797, WO 2005/060985, WO2006/048449, WO 2006/048450, WO 2006/048451, WO 2006/048452, WO 2006/097526, WO 2007/008684, WO 2007/008704, and WO 2007/009894. Notwithstanding the intense scientific and pharmaceutical interest in melanocortin receptor-specific peptides, evidenced by numerous articles in the scientific literature and numerous patent applications and issued patents (Nozawa et al, Expert Opin. Ther. Patents 18(4):403-427 (2008); Bednarek et al, Expert Opin. Ther. Patents 14(3):327-336 (2004); Todorovic et al, Peptides, 26, 2026-2036 (2005); and Ujjainwalla et al, Current Topics in Med. Chem., 7, 1068-1084 (2007)), no melanocortin receptor-specific peptide has been approved as a drug for any therapeutic indication. Indeed, there are no reports of any melanocortin receptor-specific peptide for any therapeutic indication having advanced past Phase II clinical trials. There remains a significant and substantial need for melanocortin receptor-specific peptides for use in pharmaceutical applications. It is against this background that the present invention was made.

SUMMARY OF THE INVENTION

It is therefore an object of the present invention to provide novel compounds that are useful for the treatment of diseases, disorders and/or conditions responsive to modulation, including activation, of MC4-R and/or MC3-R, in particular treatment of energy homeostasis and metabolism related (e.g. diabetes), food intake related and/or energy balance and body weight related diseases, disorders and/or conditions, including obesity, overweight and diseases, disorders and/or conditions associated with obesity and/or overweight, such as type 2 diabetes and metabolic syndrome.

In one aspect, the present invention relates to a cyclic peptide of the structural Formula (I):

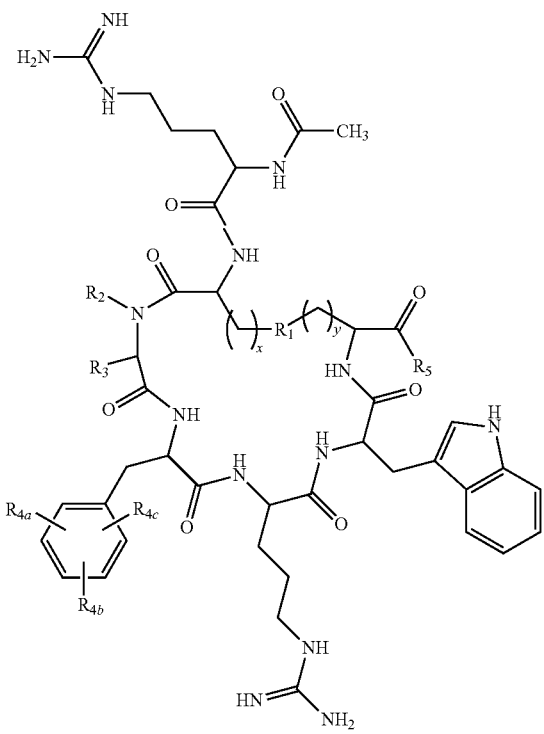

including all enantiomers, stereoisomers or diastereoisomers thereof, or a pharmaceutically acceptable salt of any of the foregoing,
wherein:
$R_1$ is —NH—C(=O)— or —C(=O)—NH—;
$R_2$ is —H or —CH$_2$—, and if $R_2$ is —CH$_2$— forms with $R_3$ a pyrrolidine ring, the pyrrolidine ring optionally substituted with —OH;
$R_3$ is —(CH$_2$)$_2$— if $R_2$ is —CH$_2$—, and otherwise $R_3$ is selected from

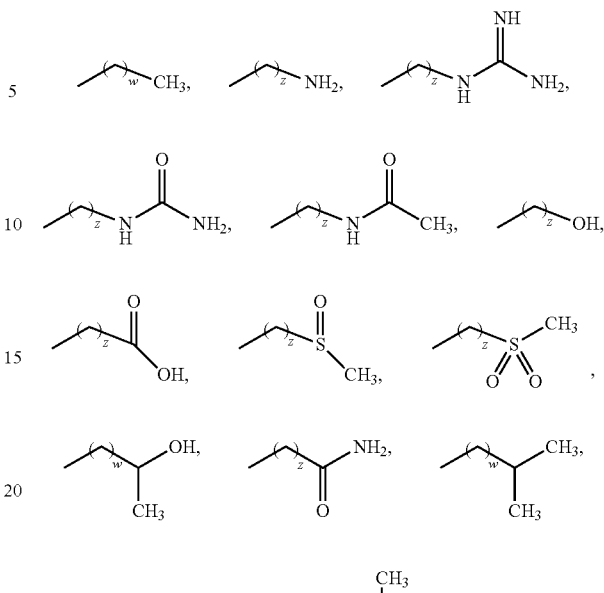

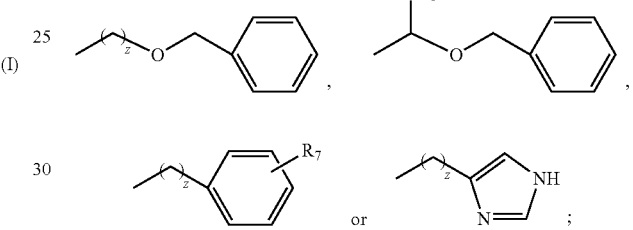

$R_{4a}$, $R_{4b}$ and $R_{4c}$ are are each independently selected from hydrogen, halo, (C$_1$-C$_{10}$)alkyl-halo, (C$_1$-C$_{10}$)alkyl-dihalo, (C$_1$-C$_{10}$)alkyl-trihalo, (C$_1$-C$_{10}$)alkyl, (C$_1$-C$_{10}$)alkoxyl, (C$_1$-C$_{10}$)alkylthio, aryl, aryloxy, nitro, nitrile, sulfonamide, amino, monosubstituted amino, disubstituted amino, hydroxy, carboxy, or alkoxy-carbonyl, on the proviso that at least one of $R_{4a}$, $R_{4b}$ and $R_{4c}$ is not hydrogen;
$R_5$ is —OH or —N(R$_{6a}$)(R$_{6b}$);
$R_{6a}$ and $R_{6b}$ are each independently H or a C$_1$ to C$_4$ linear, branched or cyclic alkyl chain;
$R_7$ is —H or —C(=O)—NH$_2$;
w is in each instance independently 0 to 5;
x is 1 to 5;
y is 1 to 5; and
z is in each instance independently 1 to 5.

In another aspect, the present invention relates to a cyclic peptide of Formula (I) which is of formula (II):

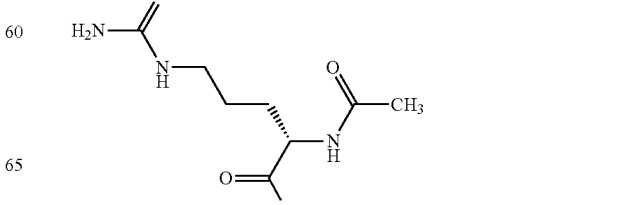

-continued

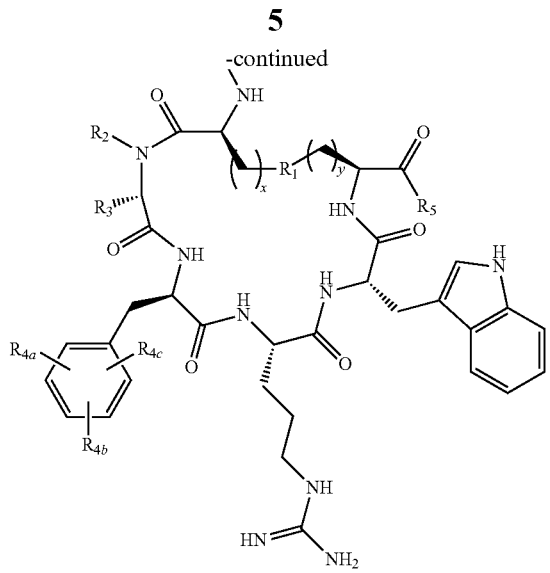

or a pharmaceutically acceptable salt thereof.

In another aspect, the present invention relates to a cyclic peptide of Formula I, in particular of Formula (II), wherein $R_1$ is —C(=O)—NH—, x is 2 and y is 3.

In another aspect, the present invention relates to a cyclic peptide of Formula (I), in particular of Formula (II), wherein $R_1$ is —NH—C(=O)—, x is 3 and y is 2.

In another aspect, the present invention relates to a cyclic peptide of Formula (I), in particular of Formula (II), wherein $R_2$ is —H or —CH$_2$—, and if $R_2$ is —CH$_2$— forms with $R_3$ a pyrrolidine ring, the pyrrolidine ring optionally substituted with —OH; and $R_3$ is —(CH$_2$)$_2$— if $R_2$ is —CH$_2$—, and otherwise $R_3$ is

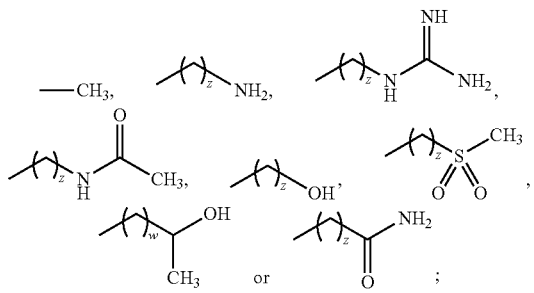

wherein w is in each instance independently selected from 0 to 5, and
z is in each instance independently selected from 1 to 5.

In another aspect, the present invention relates to a cyclic peptide of Formula I, in particular of Formula (II) or (III), wherein $R_2$ is H, $R_3$ is selected from

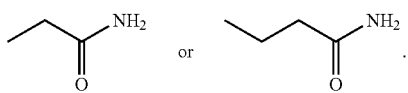

In another aspect, the present invention relates to a cyclic peptide of Formula I, in particular of Formula (II), wherein $R_2$ is —CH$_2$— and $R_3$ is —(CH$_2$)$_2$—, $R_2$ and $R_3$ together forming an unsubstituted pyrrolidine ring.

In another aspect, the present invention relates to a cyclic peptide of Formula I, in particular Formula (II), wherein at least one of $R_{4a}$, $R_{4b}$ and $R_{4c}$ is selected from

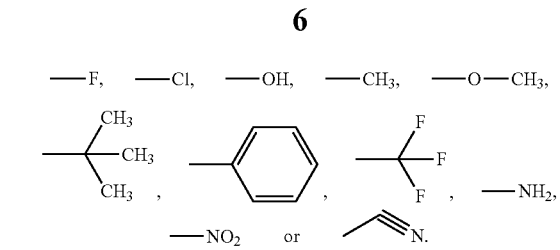

In another aspect, the present invention relates to a cyclic peptide of Formula I, in particular Formula (II) or (III), wherein $R_{4a}$ is in the 4 position and is —C≡N and $R_{4b}$ and $R_{4c}$ are each H.

In another aspect, the present invention relates to a cyclic peptide of Formula (I), in particular Formula (II) or (III), wherein $R_{4a}$ is in the 4 position and is —F and $R_{4b}$ and $R_{4c}$ are each H.

The peptides according to the invention are ligands of one or more of the melanocortin receptors, in particular ligands of the MC4-R, more particularly agonists (including full and partial agonists) of the MC4-R. The term "ligands" as used herein include peptides binding to the active site as well as peptides binding to one or more allosteric sites of any one of said receptors.

Thus, the peptides of the invention can be used as a medicament, in particular for the treatment of disorders, diseases, or conditions responsive to modulation of the MC3-R and/or MC4-R, and in particular disorders, diseases, or conditions responsive to the activation of the MC4-R. More particularly, the peptides of the invention are believed to attenuate food intake, body weight and/or body weight gain and are therefore believed to be useful for treatments of energy homeostasis and metabolism related (e.g. diabetes), food intake related and/or energy balance and body weight related diseases, disorders and/or conditions, including obesity and overweight, and diseases, disorders and/or conditions associated with obesity and/or overweight, such as type 2 diabetes and metabolic syndrome, in a patient in need thereof. The patient may be a human or non-human animal, in particular a human.

Peptides of the invention may have advantageous properties compared to peptides of the prior art, in particular enhanced potency and/or enhanced selectivity. These advantages may provide for corresponding useful properties in practice. For example, when used as pharmaceutical agents, peptides of the present invention may be used at a lower daily clinical dose, may have longer duration of action, and/or an improved side effect profile.

In another aspect of the invention, there is provided a method of treating disorders, diseases, or conditions responsive to modulation of the MC4-R and/or MC3-R, such as disorders, diseases, or conditions responsive to activation of the MC4-R, in particular energy homeostasis and metabolism related (e.g. diabetes), food intake related and/or energy balance and body weight related diseases, disorders and/or conditions, including obesity and overweight, and diseases, disorders and/or conditions associated with obesity and/or overweight, such as type 2 diabetes and metabolic syndrome, by administering a therapeutically effective amount of a peptide of the invention to a patient in need thereof.

According to a further aspect of the invention, there is provided a method of reducing food intake, body weight and/or body weight gain by administering a pharmacologically effective amount of a peptide of the invention to an individual, such as a human, in need thereof.

According to a further aspect of the invention, there is provided a method of preventing body weight regain after weight loss by administering a pharmacologically effective amount of a peptide of the invention to an individual, such as a human, in need thereof.

In a further aspect, the invention provides the use of a peptide of Formula I in the preparation of a medicament for treatment of a disease, disorder and/or condition responsive to activation of the MC4-R, in particular energy homeostasis and metabolism related (e.g. diabetes), food intake related and/or energy balance and body weight related diseases, disorders and/or conditions, including obesity and overweight, and diseases, disorders and/or conditions associated with obesity and/or overweight, such as type 2 diabetes and metabolic syndrome.

In another aspect, the present invention provides a melanocortin receptor-specific peptide-based pharmaceutical composition for use in treatment of melanocortin receptor-mediated diseases, indications, conditions and syndromes, in particular diseases, disorders, conditions and/or syndromes responsive to modulation of MC4-R, such as activation of MC4-R, comprising a peptide of Formula I and a pharmaceutically acceptable carrier.

In another aspect, the present invention provides a peptide-based melanocortin receptor-specific pharmaceutical composition comprising a peptide of Formula I and a pharmaceutically acceptable carrier, wherein the peptide is a selective MC4-R ligand, for use in treatment of energy homeostasis and metabolism related (e.g. diabetes), food intake related and/or energy balance and body weight related diseases, disorders and/or conditions, including obesity, overweight and diseases, disorders and/or conditions associated with obesity and/or overweight, such as type 2 diabetes and metabolic syndrome.

In another aspect, the present invention provides peptides which are specific for MC4-R and which are partial or full agonists at MC4-R. In particular, the present invention provides peptides which are specific for MC4-R and which are partial agonists at MC4-R.

In another aspect, the present invention provides a specific MC4-R cyclic peptide that is effective over a significant dose range.

Other aspects and novel features, and the further scope of applicability of the present invention will be set forth in part in the detailed description to follow, and in part will become apparent to those skilled in the art upon examination of the following, or may be learned by practice of the invention. The aspects of the invention may be realized and attained by means of the instrumentalities and combinations particularly pointed out in the appended claims.

DETAILED DESCRIPTION OF THE INVENTION 1.0 Definitions

Before proceeding with the description of the invention, certain terms are defined as set forth herein.

In the sequences given for the peptides according to the present invention, the amino acid residues have their conventional meaning as given in Chapter 2400 of the *Manual of Patent Examining Procedure*, 8$^{th}$ Ed. Thus, "Ala" is alanine, "Asn" is asparagine, "Asp" is aspartic acid, "Arg" is arginine, "Cys" is cysteine, "Gly" is glycine, "Gln" is glutamine, "Glu" is glutamic acid, "His" is histidine, "Ile" is isoleucine, "Leu" is leucine, "Lys" is lysine, "Met" is methionine, "Phe" is phenylalanine, "Pro" is proline, "Ser" is serine, "Thr" is Threonine, "Trp" is tryptophan, "Tyr" is tyrosine, and "Val" is valine, and so on. It is to be understood that "D" isomers are designated by a "D-" before the three letter code or amino acid name, such that for example D-Phe is D-phenylalanine Amino acid residues not encompassed by the foregoing have the following definitions:

| Abbreviation | Common Name | Side Chain or Amino Acid Structure |
|---|---|---|
| Cit | citrulline | |
| Dab | diaminobutyric acid | |
| Dab(Acetyl) | 2-amino, 4-acetylaminobutyric acid | |
| Dap | diaminoproprionic acid | |
| Hyp | hydroxyproline | |
| Met(O) | methionine sulfoxide | |
| Met(O$_2$) | methionine sulfone | |
| Nle | norleucine | |
| Nva | norvaline | |
| Orn | ornithine | |
| Phe(2-CF$_3$) | 2-trifluoromethyl phenylalanine | |
| Phe(2-C(=O)—NH$_2$) | 2-carbamoyl-phenylalanine | |
| Phe(2-Me) | 2-methyl phenylalanine | |

| Abbreviation | Common Name | Side Chain or Amino Acid Structure |
|---|---|---|
| Phe(2-CN) | 2-cyano phenylalanine | 2-cyanophenyl |
| Phe(2-Cl) | 2-chloro phenylalanine | 2-chlorophenyl |
| Phe(2,4-diCl) | 2,4-dichloro phenylalanine | 2,4-dichlorophenyl |
| Phe(2,4-diMe) | 2,4-dimethyl phenylalanine | 2,4-dimethylphenyl |
| Phe(2-F) | 2-flouro phenylalanine | 2-fluorophenyl |
| Phe(2-NO$_2$) | 2-nitro phenylalanine | 2-nitrophenyl |
| Phe(3-CF$_3$) | 3-triflouromethyl phenylalanine | 3-trifluoromethylphenyl |
| Phe(3-C(=O)—NH$_2$) | 3-carbamoyl-phenylalanine | 3-carbamoylphenyl |
| Phe(3-CN) | 3-cyano phenylalanine | 3-cyanophenyl |
| Phe(3-Cl) | 3-chloro phenylalanine | 3-chlorophenyl |
| Phe(3,4-diCl) | 3,4-dichloro phenylalanine | 3,4-dichlorophenyl |
| Phe(3-F) | 3-fluoro phenylalanine | 3-fluorophenyl |
| Phe(3,4,5-triF) | 3,4,5-trifluoro phenylalanine | 3,4,5-trifluorophenyl |
| Phe(3,4-diF) | 3,4-difluoro phenylalanine | 3,4-difluorophenyl |
| Phe(3,5-diF) | 3,5-difluoro phenylalanine | 3,5-difluorophenyl |
| Phe(3-Me) | 3-methyl phenylalanine | 3-methylphenyl |
| Phe(3-NO$_2$) | 3-nitro phenylalanine | 3-nitrophenyl |
| Phe(3,4-diOMe) | 3,4-dimethoxy phenylalanine | 3,4-dimethoxyphenyl |
| Phe(4-C(=O)—NH$_2$) | 4-carbamoyl-phenylalanine | 4-carbamoylphenyl |
| Phe(4-Me) | 4-methyl phenylalanine | 4-methylphenyl |
| Phe(4-CF$_3$) | 4-trifluoromethyl phenylalanine | 4-trifluoromethylphenyl |

| Abbreviation | Common Name | Side Chain or Amino Acid Structure |
|---|---|---|
| Phe(4-CN) | 4-cyano phenylalanine | |
| Phe(4-Cl) | 4-chloro phenylalanine | |
| Phe(4-F) | 4-fluoro phenylalanine | |
| Phe(4-NH$_2$) | 4-amino phenylalanine | |
| Phe(4-NO$_2$) | 4-nitro phenylalanine | |
| Phe(4-Ph) | 4-phenyl phenylalanine | |
| Phe(4-OMe) | 4-methoxy phenylalanine | |
| Phe(4-tBu) | 4-tert butyl phenylalanine | |
| Ser(Bzl) | O-benzyl-serine | |
| Thr(OBzl) | O-benzyl-threonine | |

The term "acyl" includes a group R(C=O)—, where R is an organic group, such as an alkyl, aryl, heteroaryl, carbocyclyl or heterocyclyl. Thus, when reference is made herein to a substituted acyl group, it means that said organic group (R) is substituted. An example is the acetyl group CH$_3$—C(=O)—, referred to herein as "Ac". A peptide or aliphatic moiety is "acylated" when an alkyl or substituted alkyl group as defined above is bonded through one or more carbonyl {—(C=O)—} groups. A peptide is most usually acylated at the N-terminus.

The term "alkane" includes linear or branched saturated hydrocarbons. Examples of linear alkane groups include methane, ethane, propane, and the like. Examples of branched or substituted alkane groups include methylbutane or dimethylbutane, methylpentane, dimethylpentane or trimethylpentane, and the like. In general, any alkyl group may be a substituent of an alkane.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The term "alkyl" includes a straight or branched chain saturated aliphatic hydrocarbon group. $C_{1-10}$ alkyl means an alkyl having from 1 to 10 carbon atoms. Non-limiting examples of such alkyl radicals include methyl, ethyl, propyl, isopropyl, butyl, sec-butyl, tertiary butyl, pentyl, isopentyl, hexyl, isohexyl, and the like.

The term "alkyne" includes a linear monovalent hydrocarbon radical of two to six carbon atoms or a branched monovalent hydrocarbon radical of three to six carbon atoms containing at least one triple bond; examples thereof include ethyne, propyne, butyne, and the like.

The term "aryl" includes a monocyclic or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. The term "aryl" also includes bicyclic aromatic ring systems wherein one ring is aromatic and one ring is non-aromatic (including saturated or partially saturated rings). In bicyclic aromatic ring systems, two or more ring carbons are common to two adjoining rings (the rings are "fused rings"). Examples of an aryl group include phenyl, biphenyl, indanyl, naphthyl, 1-naphthyl, and 2-naphthyl, derivatives thereof, and the like.

The term "aralkyl" includes a radical —R$^a$R$^b$ where R$^a$ is an alkylene (a bivalent alkyl) group and R$^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

As used herein, the term "amide" includes compounds that have a trivalent nitrogen attached to a carbonyl group, i.e. —C(=O)—NH$_2$ (i.e. primary amide), —C(=O)—NHR$_c$ and —C(=O)—NR$_c$R$_d$, wherein each of R$_c$ and R$_d$ independently represents an organic group. When reference is made herein to a substituted amide group, it means that at least one of said organic groups (R$_c$ and R$_d$) is substituted. Examples of amides include methylamide, ethylamide, propylamide, and the like.

The term "amine" includes —NH$_2$ (i.e. an amino group), —NHR$_a$ and —NR$_a$R$_b$, wherein each of R$_a$ and R$_b$ independently represents an organic group. When reference is made herein to a substituted amine group, it means that at least one of said organic groups (R$_a$ and R$_b$) is substituted.

The term "nitrile" includes the functional group —C≡N.

The term "halogen" (or "halo") is intended to include the halogen atoms fluorine, chlorine, bromine and iodine.

The term "alkyl-halo" includes an alkyl substituted with one halogen atom, such as —CH$_2$F. The term "alkyl-dihalo" includes an alkyl substituted with two halogen atoms, such as —CHF$_2$. The term "alkyl-trihalo" includes an alkyl substituted with three halogen atoms, such as —CF$_3$.

The term "alkylthio" includes —S-alkyl wherein alkyl is as defined above. Non-limiting examples of C$_1$-C$_{10}$ alkylthio include methylthio, ethylthio, n-propylthio, iso-propylthio, and n-butylthio.

The term "nitro" is intended to include —NO$_2$.

The term "hydroxy" is intended to include —OH.

The term "alkoxy" includes —O-alkyl wherein alkyl is as defined above. C$_1$-C$_{10}$ alkoxy includes an alkyl having from 1 to 10 carbon atoms. Non-limiting examples of C$_1$-C$_{10}$ alkoxy include methoxy, ethoxy, n-propyloxy, iso-propyloxy, and 2-methyl-1-propyloxy.

The term "aryloxy" includes —O-aryl wherein aryl is as defined above.

The term "alkoxycarbonyl" includes —C(=O)—O—R, wherein R is an alkyl as defined above. Non-limiting examples of C$_1$-C$_{10}$ alkoxycarbonyl include methoxycarbonyl, ethoxycarbonyl, isopropoxy-carbonyl and isopentoxycarbonyl.

The term "carboxy" includes —C(=O)OH.

The term "oxo" includes =O.

The term "sulfonamide" includes a sulfonyl group connected to an amine group, i.e. —S(=O)$_2$NH$_2$, —S(=O)$_2$NHR$_a$, and —S(=O)$_2$NR$_a$R$_b$, wherein each of R$_a$ and R$_b$ independently represents an organic group. When reference is made herein to a substituted sulfonamide group, it means that at least one of said organic groups (R$_a$ and R$_b$) is substituted.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions utilized in the present invention encompass any composition made by admixing an active ingredient and one or more pharmaceutically acceptable carriers.

By a melanocortin receptor "agonist" is meant an endogenous substance, drug substance or compound, including a compound such as the peptides of the present invention, which can interact with a melanocortin receptor and initiate a pharmacological response, including but not limited to adenyl cyclase activation, characteristic of the melanocortin receptor.

By "α-MSH" is meant the peptide Ac-Ser-Tyr-Ser-Met-Glu-His-Phe-Arg-Trp-Gly-Lys-Pro-Val-NH$_2$ (SEQ ID NO:4) and analogs and homologs thereof, including without limitation NDP-α-MSH.

By "NDP-α-MSH" is meant the peptide Ac-Ser-Tyr-Ser-Nle-Glu-His-D-Phe-Arg-Trp-Gly-Lys-Pro-Val-NH$_2$ (SEQ ID NO:5) and analogs and homologs thereof.

By "EC$_{50}$" is meant the molar concentration of an agonist, including a partial agonist, which produced 50% of the maximum possible response for that agonist. By way of example, a test compound which, at a concentration of 72 nM, produces 50% of the maximum possible response for that compound as determined in a cAMP assay in an MC4-R cell expression system has an EC$_{50}$ of 72 nM. Unless otherwise specified, the molar concentration associated with an EC$_{50}$ determination is in nanomoles per liter (nM).

By "Ki (nM)" is meant the equilibrium inhibitor dissociation constant representing the molar concentration of a competing compound that binds to half the binding sites of a receptor at equilibrium in the absence of radioligand or other competitors. In general, the numeric value of the Ki is inversely correlated to the affinity of the compound for the receptor, such that if the Ki is low, the affinity is high. Ki may be determined using the equation of Cheng and Prusoff (Cheng Y., Prusoff W. H., Biochem. Pharmacol. 22: 3099-3108, 1973):

Ki may be expressed in terms of specific receptors (e.g., MC1-R, MC3-R, MC4-R or MC5-R) and specific ligands (e.g. α-MSH or NDP-α-MSH).

By "inhibition" is meant the percent attenuation, or decrease in receptor binding, in a competitive inhibition assay compared to a known standard. Thus, by "inhibition at 1 μM (NDP-α-MSH)" is meant the percent decrease in binding of NDP-α-MSH by addition of a determined amount of the compound to be tested, such as 1 μM of a test compound, such as under the assay conditions hereafter described. By way of example, a test compound that does not inhibit binding of NDP-α-MSH has a 0% inhibition, and a test compound that completely inhibits binding of NDP-α-MSH has a 100% inhibition. Typically, as described hereafter, a radio assay is used for competitive inhibition testing, such as with I$^{125}$-labeled NDP-α-MSH, or a lanthanide chelate fluorescent assay, such as with Eu-NDP-α-MSH. However, other methods of testing competitive inhibition are known, including use of label or tag systems other than radioisotopes, and in general any method known in the art for testing competitive inhibition may be employed in this invention. It may thus be seen that "inhibition" is one measure to determine whether a test compound attenuates binding of α-MSH to melanocortin receptors.

By "binding affinity" is meant the ability of a compound or drug to bind to its biological target, expressed herein as Ki (nM).

By "intrinsic activity" is meant the maximal stimulation (functional activity) achievable by a compound in a specified melanocortin receptor expressing cell system, such as the maximal stimulation of adenylyl cyclase. The maximal stimulation achieved by α-MSH or NDP-α-MSH is designated as an intrinsic activity of 1.0 (or 100%) and a compound capable of stimulating half the maximal activity that of α-MSH or NDP-α-MSH is designated as having an intrinsic activity of 0.5 (or 50%). A compound of this invention that under assay conditions described herein has an intrinsic activity of 0.7 (70%) or higher is classified as an agonist, a compound with intrinsic activity between 0.1 (10%) and 0.7 (70%) is classified as a partial agonist, and a compound with intrinsic activity below 0.1 (10%) is classified as inactive or having no intrinsic activity. In one aspect, the cyclic peptides of the present invention may generally be characterized as a partial agonist at MC4-R with respect to α-MSH or NDP-α-MSH.

In general, "functional activity" is a measure of the signaling of a receptor, or measure of a change in receptor-associated signaling, such as a melanocortin receptor, and in particular MC4-R or hMC4-R, upon activation by a compound. Melanocortin receptors initiate signal transduction through activation of heterotrimeric G proteins. In one aspect, melanocortin receptors signal through Gα$_s$, which catalyzes production of cAMP by adenylyl cyclase. Thus determination of stimulation of adenylyl cyclase, such as determination of maximal stimulation of adenylyl cyclase, is one measure of functional activity, and is the primary measure exemplified herein. However, it is to be understood that alternative measures of functional activity may be employed in the practice of this invention, and are specifically contemplated and included within the scope of this invention. Thus, in one example intracellular free calcium may be measured, such as reported by and using the methods disclosed in Mountjoy K. G. et al., Melanocortin receptor-medicated mobilization of intracellular free calcium in HEK293 cells. *Physiol Genomics* 5:11-19, 2001, or Kassack M. U. et al., Functional screening of G protein-coupled receptors by measuring intracellular calcium with a fluorescence microplate reader. *Biomol Screening* 7:233-246, 2002. It is also possible to measure activation by measurement of the production of inositol triphosphate or diacylglycerol from phosphatidylinositol 4,5-biphosphate, such as by use of radioassays. Yet another measure of functional activity is receptor internalization, resulting from activation of regulatory pathways, such as using the methods disclosed in Nickolls S. A. et al., Functional selectivity of melanocortin 4 receptor peptide and nonpeptide agonists: evidence for ligand specific conformational states. *J Pharm Exper Therapeutics* 313:1281-1288, 2005. Yet another measure of functional activity is the exchange, and exchange rate, of nucleotides associated with activation of a G protein receptor, such as the exchange of GDP (guanosine diphosphate) for GTP (guanosine triphosphase) on the G protein α subunit, which may be measured by any number of means, including a radioassay using guanosine 5'-(γ-[$^{35}$S]thio)-triphosphate, as disclosed in Manning D. R., Measures of efficacy using G proteins as endpoints: differential engagement of G proteins through single receptors. *Mol Pharmacol* 62:451-452, 2002. Various gene-based assays have been developed for measuring activation of G-coupled proteins, such as those disclosed in Chen W. et al., A colorimetric assay from measuring activation of Gs- and Gq-coupled signaling pathways. *Anal Biochem* 226:349-354, 1995; Kent T. C. et al., Development of a generic dual-reporter gene assay for screening G-protein-coupled receptors. *Biomol Screening,* 5:437-446, 2005; or Kotarsky K. et al., Improved receptor gene assays used to identify ligands acting on orphan seven-transmembrane receptors. *Pharmacology & Toxicology* 93:249-258, 2003. The colorimetric assay of Chen et al. has been adapted for use in measuring melanocortin receptor activation, as disclosed in Hruby V. J. et al., Cyclic lactam α-melanocortin analogues of Ac-Nle$^4$-cyclo[Asp$^5$,D-Phe$^7$,Lys$^{10}$] α-melanocyte-stimulating hormone-(4-10)-NH$_2$ with bulky aromatic amino acids at position 7 shows high antagonist potency and selectivity at specific melanocortin receptors. *J Med Chem* 38:3454-3461, 1995. In general, functional activity may be measured by any method, including methods of determining activation and/or signaling of a G-coupled receptor, and further including methods which may be hereafter developed or reported. The terms "treat," "treating" and "treatment," as used herein, contemplate an action that occurs while a patient is suffering from the specified disease, disorder and/or condition, which reduces the severity of the disease, disorder and/or condition. Moreover, the terms "treat," "treating" and "treatment," as used herein are intended to embrace therapeutic (curative), prophylactic (preventing), controlling and palliative treatment of the indicated diseases, disorders and/or conditions.

As used herein, the term "pharmacologically effective amount" (including "therapeutically effective amount") means an amount of a peptide according to the invention that is sufficient to induce a desired therapeutic or biological effect.

As used herein, the term "therapeutically effective amount" means the amount of a peptide of the invention that will elicit a biological or medical response in the mammal that is being treated by a medical doctor or other clinician.

As used herein, the term "prophylactically effective" or "preventive" means the amount of a peptide of the invention that will prevent or inhibit affliction or mitigate affliction of a mammal with a medical condition that a medical doctor or other clinician is trying to prevent, inhibit, or mitigate before a patient begins to suffer from the specified disease or disorder.

The term "diabetes" includes Type 1 Diabetes, which is insulin-dependent diabetes mellitus as diagnosed according to criteria published in the Report of the Expert Committee on the Diagnosis and Classification of Diabetes Mellitus (*Diabetes Care*, Vol. 24, Supp. 1, Jan. 2001) whereby fasting plasma glucose level is greater than or equal to 126 milligrams per deciliter and for which the primary cause is pancreatic beta cell destruction, Type 2 Diabetes, which is non-insulin-dependent diabetes mellitus as diagnosed according to criteria published in the Report of the Expert Committee on the Diagnosis and Classification of Diabetes Mellitus whereby fasting plasma glucose level is greater than or equal to 126 milligrams per deciliter, and latent autoimmune diabetes mellitus of adults (LADA).

The term "metabolic syndrome" refers to metabolic disorders, particularly glucose and lipid regulatory disorders, including insulin resistance and defective secretion of insulin by pancreatic beta cells, and may further include conditions and states such as abdominal obesity, dyslipidemia, hypertension, glucose intolerance or a prothrombitic state, and which may further result in disorders such as hyperlipidemia, obesity, diabetes, insulin resistance, glucose intolerance, hyperglycemia, and hypertension.

2.0 Clinical Indications and Utility

The compositions and methods disclosed herein can be used for both medical applications and animal husbandry or veterinary applications. Typically, the methods are used in humans, but may also be used in other mammals. The term "patient" is intended to denote a mammalian individual, and is so used throughout the specification and in the claims. The primary applications of the present invention involve human patients, but the present invention may be applied to laboratory, farm, zoo, wildlife, pet, sport or other animals. Clinical indications and specific utilities include the following:

2.1 Obesity and Related Metabolic Syndrome.

Peptides of Formula (I), and in particular Formula (II) or (III), have been found to be ligands of the MC4 receptor. In particular, peptides of Formula (I) are believed to be useful in treating diseases, disorders and/or conditions responsive to modulation of the MC4-R function, more particularly activation of the MC4-R, i.e. diseases, disorders and/or conditions which would benefit from agonism (including full or partial agonism) at the MC4-R, including energy homeostasis and metabolism related (such as diabetes, in particular type 2 diabetes; dyslipidemia; fatty liver; hypercholesterolemia; hypertriglyceridemia; hyperuricacidemia; impaired glucose tolerance; impaired fasting glucos; insulin resistance syndrome; and metabolic syndrome), food intake related (such as hyperphagia; binge eating; bulimia; and compulsive eating) and/or energy balance and body weight related diseases, disorders and/or conditions, more particularly such diseases, disorders and conditions characterized by excess body weight and/or excess food intake.

Peptides of Formula (I), and in particular Formula (II) or (III), are particularly believed to be useful for treatment of body weight related diseases, disorders and/or conditions characterized by excess body weight, including obesity and overweight (by promotion of weight loss, maintenance of weight loss, and/or prevention of weight gain, including medication-induced weight gain or weight gain subsequent to cessation of smoking), and diseases, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; non-alcoholic fatty liver disease (including non-alcoholic steatohepatitis); joint disorders (including secondary osteoarthritis); gastroesophageal reflux; sleep apnea; atherosclerosis; stroke; macro and micro vascular diseases; steatosis (e.g. in the liver); gall stones; and gallbladder disorders.

Peptides of Formula (I), and in particular Formula (II) or (III), are particularly believed to be useful for treatment of obesity and type 2 diabetes, more specifically obesity.

It will be understood that there are medically accepted definitions of obesity and overweight. A patient may be identified by, for example, measuring body mass index (BMI), which is calculated by dividing weight in kilograms by height in meters squared, and comparing the result with the definitions. The recommended classifications for BMI in humans, adopted by the Expert Panel on the Identification, Evaluation and Treatment of Overweight and Obesity in Adults, and endorsed by leading organizations of health professionals, are as follows: underweight <18.5 kg/m$^2$, normal weight 18.5-24.9 kg/m$^2$, overweight 25-29.9 kg/m$_2$, obesity (class 1) 30-34.9 kg/m$^2$, obesity (class 2) 35-39.9 kg/m$^2$, extreme obesity (class 3)≥40 kg/m$^2$ (Practical Guide to the Identification, Evaluation, and Treatment of Overweight and Obesity in Adults, The North American Association for the Study of Obesity (NAASO) and the National Heart, Lung and Blood Institute (NHLBI) 2000). Modifications of this classification may be used for specific ethnic groups and for children. Another alternative for assessing overweight and obesity is by measuring waist circumference. There are several proposed classifications and differences in the cutoffs based on ethnic group. For instance, according to the classification from the International Diabetes Federation, men having waist circumferences above 94 cm (cut off for europids) and women having waist circumferences above 80 cm (cut off for europids) are at higher risk of diabetes, dyslipidemia, hypertension and cardiovascular diseases because of excess abdominal fat. Another classification is based on the recommendation from the Adult Treatment Panel III where the recommended cutoffs are 102 cm for men and 88 cm for women. However, the peptides of Formula (I) may also be used for reduction of self-diagnosed overweight and for decreasing the risk of becoming obese due to life style, genetic considerations, heredity and/or other factors.

It is believed that peptides of Formula (I), and in particular Formula (II) or (III), upon administration to an animal, including man, will reduce food intake, body weight and/or body weight gain in that animal.

Without being bound by any theory, it is believed that peptides of Formula (I), and in particular Formula (II) or (III), act by modulating appetite and/or satiety, increasing metabolic rate, reducing intake of and/or craving for fat and/or carbohydrates.

Without being bound by any theory, it is also believed that peptides of Formula (I), and in particular Formula (II) or (III), act by enhancing glucose tolerance and/or decreasing insulin resistance. It is therefore believed that peptides of Formula (I) can be useful also for treatment of type 2 diabetes in underweight and normal weight individuals as well as in overweight and obese individuals.

Peptides of the invention might also be useful for (i) prevention of organ or tissue damage caused by hypoperfusion due to vessel occlusion (e.g. caused by thrombosis), haemorrhage, trauma, surgery, haemorrhagic shock, cardiogenic shock, toxic shock or septic shock or (iii) treatment of male and female sexual dysfunctions, such as male erectile dysfunction or female sexual arousal dysfunction.

According to a further aspect of the invention, there is provided a peptide of Formula (I), and in particular Formula (II) or (III), as previously defined for use as a medicament.

In another aspect, the invention provides the use of a peptide of Formula (I), and in particular Formula (II) or (III), for treatment of diseases, disorders and/or conditions responsive to modulation of the MC4-R, such as diseases, disorders and/or conditions responsive to activation of the MC4-R, in particular energy homeostasis and metabolism related (e.g. diabetes), food intake related and/or energy balance and body weight related diseases, disorders and/or conditions, including obesity, overweight and diseases, disorders and/or conditions associated with obesity and/or overweight, such as type 2 diabetes and metabolic syndrome.

In a further aspect, the invention provides the use of a peptide of Formula (I), and in particular Formula (II) or (III), in the preparation of a medicament for treatment of diseases, disorders and/or conditions responsive to modulation of the MC4-R, such as activation of the MC4-R, in particular energy homeostasis and metabolism related (e.g. diabetes), food intake related and/or energy balance and body weight related diseases, disorders and/or conditions, including obesity, overweight and diseases, disorders and/or conditions associated with obesity and/or overweight, such as type 2 diabetes and metabolic syndrome.

Peptides of the invention are advantageously more selective (i.e. higher affinity and/or higher specificity) for MC4-R and/or MC3-R than for MC1-R, MC2-R and MC5-R, in particular MC1-R. In particular, peptides of the invention are advantageously more selective for MC4-R than for any of MC3-R and MC1-R. Peptides of the invention are suitably at least 3-fold, in particular 10-fold, more particularly 30-fold, more selective for MC4-R than for any of MC1-R, MC2-R, MC3-R and MC5-R. Some peptides of the invention are even more than 100-fold, such as even about 150-fold, more selective for MC4-R than MC1-R as determined in the receptor binding assay described in 7.1. It is noted that the selectivity profile may affect in vivo safety and side effects obtained upon administration of the peptides.

Upon treatment of energy homeostasis and metabolism related, food intake related and/or energy balance and body weight related diseases, disorders and/or conditions, it is desirable to reduce or eliminate unwanted side-effects that may result from MC4-R activation, such as sexual side-effects, including penile erection, and blood pressure effects.

Peptides of the invention are believed to be useful for treatment of energy homeostasis and metabolism related (e.g. diabetes), food intake related and/or energy balance and body weight related diseases, disorders and/or conditions, including obesity, overweight and diseases, disorders and/or conditions associated with obesity and/or overweight, such as type 2 diabetes and metabolic syndrome, without causing substantial adverse cardiovascular effects, including a substantial increase in blood pressure.

Peptides of the invention are believed to be useful for treatment of energy homeostasis and metabolism related (e.g. diabetes), food intake related and/or energy balance and body weight related diseases, disorders and/or conditions, including obesity, overweight and diseases, disorders and/or conditions associated with obesity and/or overweight, such as type 2 diabetes and metabolic syndrome, without causing substantial unwanted sexual effects resulting from MC4-R activation, such as penile erection.

It is believed that peptides of Formula I, and in particular Formula (II) or (III), possess a satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art.

3.0 Combination Therapy for Certain Indications

The peptides, compositions and methods of the present invention may be used for treatment of any of the foregoing diseases, indications, conditions or syndromes, or any disease, indication, condition or syndrome which is melanocortin receptor mediated, by administration in combination with one or more other pharmaceutically active compounds. Such combination administration may be by means of a single dosage form which includes both a peptide of the present invention and one more other pharmaceutically active compound, such single dosage form including a tablet, capsule, spray, inhalation powder, injectable liquid or the like. Alternatively, combination administration may be by means of administration of two different dosage forms, with one dosage form containing a peptide of the present invention, and the other dosage form including another pharmaceutically active compound. In this instance, the dosage forms may be the same or different. Without meaning to limit combination therapies, the following exemplifies certain combination therapies which may be employed.

3.1 Combination Therapy for Obesity and Related Metabolic Syndrome.

One or more peptides of the invention may be combined with one or more other pharmacologically active agent(s) that is (are) useful in the treatment of various weight and feeding-related disorders, such as obesity and/or overweight, in particular other anti-obesity drugs that affect energy expenditure, glycolysis, gluconeogenesis, glucogenolysis, lipolysis, lipogenesis, fat absorption, fat storage, fat excretion, hunger and/or satiety and/or craving mechanisms, appetite/motivation, food intake, or gastrointestinal motility. Drugs that reduce energy intake include, in part, various pharmacological agents, referred to as anorectic drugs, which are used as adjuncts to behavioral therapy in weight reduction programs.

Generally, a total dosage of the below-described obesity control agents or medications, when used in combination with one or more peptides of the present invention can range from 0.1 to 3,000 mg/day, preferably from about 1 to 1,000 mg/day and more preferably from about 1 to 200 mg/day in single or 2-4 divided doses. The exact dose, however, is determined by the attending clinician and is dependent on such factors as the potency of the compound administered, the age, weight, condition and response of the patient.

One or more peptides of the invention may be combined with one or more other pharmacologically active agent(s) that is (are) useful in the treatment of diabetes, such as other anti-diabetic drugs.

One or more peptides of the invention may in addition or alternatively further be combined with one or more other pharmacologically active agent(s) that is (are) useful in the treatment of diseases, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; non-alcoholic fatty liver disease (including non-alcoholic steatohepatitis); joint disorders (including secondary osteoarthritis); gastroesophageal reflux; sleep apnea; atherosclerosis; stroke; macro and micro vascular diseases; steatosis (e.g. in the liver); gall stones; and gallbladder disorders.

According to a further aspect of the invention there is provided a combination treatment comprising the administration of a pharmacologically effective amount of a peptide according to the invention, or a pharmaceutically acceptable salt thereof, optionally together with a pharmaceutically acceptable diluent or carrier, with the simultaneous, sequential or separate administration one or more of the following agents selected from:

insulin and insulin analogues;

insulin secretagogues, including sulphonylureas (e.g. glipizide) and prandial glucose regulators (sometimes called "short-acting secretagogues"), such as meglitinides (e.g. repaglinide and nateglinide);

agents that improve incretin action, for example dipeptidyl peptidase IV (DPP-4) inhibitors (e.g. vildagliptin, saxagliptin, and sitagliptin), and glucagon-like peptide-1 (GLP-1) agonists (e.g. exenatide);

insulin sensitising agents including peroxisome proliferator activated receptor gamma (PPARγ) agonists, such as thiazolidinediones (e.g. pioglitazone and rosiglitazone), and agents with any combination of PPAR alpha, gamma and delta activity;

agents that modulate hepatic glucose balance, for example biguanides (e.g. metformin), fructose 1,6-bisphosphatase inhibitors, glycogen phopsphorylase inhibitors, glycogen synthase kinase inhibitors, and glucokinase activators;

agents designed to reduce/slow the absorption of glucose from the intestine, such as alpha-glucosidase inhibitors (e.g. miglitol and acarbose);

agents which antagonise the actions of or reduce secretion of glucagon, such as amylin analogues (e.g. pramlintide);

agents that prevent the reabsorption of glucose by the kidney, such as sodium-dependent glucose transporter 2 (SGLT-2) inhibitors (e.g. dapagliflozin);

agents designed to treat the complications of prolonged hyperglycaemia, such as aldose reductase inhibitors (e.g. epalrestat and ranirestat); and agents used to treat complications related to micro-angiopathies;

anti-dyslipidemia agents, such as HMG-CoA reductase inhibitors (statins, e.g. rosuvastatin) and other cholesterol-lowering agents; PPARα agonists (fibrates, e.g. gemfibrozil and fenofibrate); bile acid sequestrants (e.g. cholestyramine); cholesterol absorption inhibitors (e.g. plant sterols (i.e. phytosterols), synthetic inhibitors); cholesteryl ester transfer protein (CETP) inhibitors; inhibitors of the ileal bile acid transport system (IBAT inhibitors); bile acid binding resins; nicotinic acid (niacin) and analogues thereof; anti-oxidants, such as probucol; and omega-3 fatty acids;

antihypertensive agents, including adrenergic receptor antagonists, such as beta blockers (e.g. atenolol), alpha blockers (e.g. doxazosin), and mixed alpha/beta blockers (e.g. labetalol); adrenergic receptor agonists, including alpha-2 agonists (e.g. clonidine); angiotensin converting enzyme (ACE) inhibitors (e.g. lisinopril), calcium channel blockers, such as dihydropyridines (e.g. nifedipine), phenylalkylamines (e.g. verapamil), and benzothiazepines (e.g. diltiazem); angiotensin II receptor antagonists (e.g. candesartan); aldosterone receptor antagonists (e.g. eplerenone); centrally acting adrenergic drugs, such as central alpha agonists (e.g. clonidine); and diuretic agents (e.g. furosemide);

haemostasis modulators, including antithrombotics, such as activators of fibrinolysis; thrombin antagonists; factor VIIa inhibitors; anticoagulants, such as vitamin K antagonists (e.g. warfarin), heparin and low molecular weight analogues thereof, factor Xa inhibitors, and direct thrombin inhibitors (e.g. argatroban); antiplatelet agents, such as cyclooxygenase inhibitors (e.g. aspirin), adenosine diphosphate (ADP) receptor inhibitors (e.g. clopidogrel), phosphodiesterase inhibitors (e.g. cilostazol), glycoprotein IIB/IIA inhibitors (e.g. tirofiban), and adenosine reuptake inhibitors (e.g. dipyridamole);

anti-obesity agents, such as appetite suppressant (e.g. ephedrine), including noradrenergic agents (e.g. phentermine) and serotonergic agents (e.g. sibutramine), pancreatic lipase inhibitors (e.g. orlistat), microsomal transfer protein (MTP) modulators, diacyl glycerolacyltransferase (DGAT) inhibitors, and cannabinoid (CB1) receptor antagonists (e.g. rimonabant);

feeding behavior modifying agents, such as orexin receptor modulators and melanin-concentrating hormone (MCH) modulators;

glucagon like peptide-1 (GLP-1) receptor modulators;
neuropeptideY (NPY)/NPY receptor modulators;
pyruvate dehydrogenase kinase (PDK) modulators;
serotonin receptor modulators;
leptin/leptin receptor modulators;
ghrelin/ghrelin receptor modulators; or
monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), triple monoamine reuptake blockers (e.g. tesofensine), and monoamine oxidase inhibitors (MAOI) (e.g. toloxatone and amiflamine), or a pharmaceutically acceptable salt, solvate, solvate of such a salt or a prodrug thereof, optionally together with a pharmaceutically acceptable carrier to a mammal, such as man, in need of such therapeutic treatment.

According to an additional further aspect of the present invention there is provided a combination treatment comprising the administration of a pharmacologically effective amount of a compound according to the invention, or a pharmaceutically acceptable salt thereof, optionally together with a pharmaceutically acceptable carrier, with the simultaneous, sequential or separate administration of very low calorie diets (VLCD) or low-calorie diets (LCD).

4.0 Methods of Making

In general, the peptides of the present invention may be synthesized by solid-phase synthesis and purified according to methods known in the art. Any of a number of well-known procedures utilizing a variety of resins and reagents may be used to prepare the peptides of the present invention.

The cyclic peptides of the present invention may be readily synthesized by known conventional procedures for the formation of a peptide linkage between amino acids. Such conventional procedures include, for example, any solution phase procedure permitting a condensation between the free alpha amino group of an amino acid or residue thereof having its carboxyl group and other reactive groups protected and the free primary carboxyl group of another amino acid or residue thereof having its amino group or other reactive groups protected. In a preferred conventional procedure, the cyclic peptides of the present invention may be synthesized by solid-phase synthesis and purified according to methods known in the art. Any of a number of well-known procedures utilizing a variety of resins and reagents may be used to prepare the peptides of the present invention.

The process for synthesizing the cyclic peptides may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide. The resulting peptide is then cyclized to yield a cyclic peptide of the invention.

Solid phase peptide synthesis methods are well known and practiced in the art. In such methods the synthesis of peptides of the invention can be carried out by sequentially incorporating the desired amino acid residues one at a time into the growing peptide chain according to the general principles of solid phase methods. These methods are disclosed in numerous references, including Merrifield, R. B., Solid phase synthesis (Nobel lecture). *Angew Chem* 24:799-810 (1985) and Barany et al., The Peptides, Analysis, Synthesis and Biology, Vol. 2, Gross, E. and Meienhofer, J., Eds. Academic Press 1-284 (1980).

In chemical syntheses of peptides, reactive side chain groups of the various amino acid residues are protected with suitable protecting groups, which prevent a chemical reaction from occurring at that site until the protecting group is removed. Also common is the protection of the alpha amino group of an amino acid residue or fragment while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods.

Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz) and aliphatic urethane-type protecting groups, such as t-butyloxycarbonyl (Boc), diisopropylmethoxycarbonyl, isopropoxycarbonyl, and allyloxycarbonyl (Alloc). Fmoc are preferred for alpha amino protection.

Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf) and Boc. Pbf and Pmc are preferred protecting groups for Arg.

The peptides of the invention described herein were prepared using solid phase synthesis, such as by means of a Symphony Multiplex Peptide Synthesizer (Rainin Instrument Company/Protein Technologies Inc) automated peptide synthesizer, using programming modules as provided by the manufacturer and following the protocols set forth in the manufacturer's manual.

Solid phase synthesis is commenced from the C-terminal end of the peptide by coupling a protected alpha amino acid to a suitable resin. Such starting material is prepared by attaching an alpha amino-protected amino acid by an amide linkage to a 4-(2', 4'-dimethoxylphenyl-aminomethyl-phenoxy (Rink Amide) resin, a 4-(2',4'-dimethoxylphenyl-aminomethyl)-phenoxyacetamido-norleucyl-MBHA resin, an amino-xanthen-3-yloxy-merifiel resin (Sieber Amide) resin, or by an ester linkage to a p-benzyloxybenzyl alcohol (Wang) resin, a 2-chlorotrityl chloride resin or by other means well known in the art. Fmoc-Linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20-40% v/v) in N,N-dimethylformamide (DMF) may be used for this purpose.

Following removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. After the peptide is synthesized, if desired, the orthogonally protected side chain protecting groups may be removed using methods well known in the art for further derivatization of the peptide.

Typically, orthogonal protecting groups are used as appropriate. For example, the peptides of the invention contain multiple amino acids with an amino group-containing side chain. In one aspect, an Allyl-Alloc protection scheme is employed with the amino acids forming a lactam bridge through their side chains, and orthogonal protecting groups, cleavable under different reactive conditions, use for other amino acids with amino group-containing side chains. Thus, for example, Fmoc-Orn(Alloc)-OH and Fmoc-Glu(OAll)-OH amino acids (Glu(OAll) refers to glutamic acid 5-allyl ester) can be employed for the positions forming a lactam bridge upon cyclization, while other amino acids with amino group-containing side chains have a different and orthogonal protecting group, such as with Fmoc-Arg(Pbf)-OH, Fmoc-Lys(Pbf)-OH, Fmoc-Dab(Pbf)-OH or the like. Other protecting groups may be similarly employed; by way of example and not limitation, Mtt/OPp (4-methyltrityl/2-phenylisopropyl) can be employed with the side chains forming a lactam bridge upon cyclization, with orthogonal protecting groups being utilized for other positions that are not cleavable using conditions suitable for cleavage of Mtt/OPp.

Reactive groups in a peptide can be selectively modified, either during solid phase synthesis or after removal from the resin. For example, peptides can be modified to obtain N-terminus modifications, such as acetylation, while on resin, or may be removed from the resin by use of a cleaving reagent and then modified. Similarly, methods for modifying side chains of amino acids are well known to those skilled in the art of peptide synthesis. The choice of modifications made to reactive groups present on the peptide will be determined, in part, by the characteristics that are desired in the peptide.

In the peptides of the present invention, in one embodiment the N-terminus group is modified by introduction of an N-acetyl group. In one aspect, a method is employed wherein after removal of the protecting group at the N-terminal, the resin-bound peptide is reacted with acetic anhydride in DMF in the presence of an organic base, such aspyridine. Other methods of N-terminus acetylation are known in the art, including solution phase acetylation, and may be employed.

The peptide can, in one embodiment, be cyclized prior to cleavage from the peptide resin. For cyclization through reactive side chain moieties, the desired side chains are deprotected, and the peptide suspended in a suitable solvent and a cyclic coupling agent added. Suitable solvents include, for example DMF, dichloromethane (DCM) or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), benzotriazole-1-yl-oxy-tris(dimethylamino)phosphonium-hexafluorophosphate (BOP), benzotriazole-1-yl-oxy-tris(pyrrolidino)phosphoniumhexafluorophosphate (PyBOP), 2-(7-aza-1H-benzotriazol-1-yl)-1,1,3,3-tetramethyluronium tetrafluoroborate (TATU), 2-(2-oxo-1(2H)-pyridyl)-1,1,3,3-tetramethyluronium tetrafluoroborate (TPTU) or N,N'-dicyclohexylcarbodiimide/1-hydroxybenzotriazole (DCCI/HOBt). Coupling is conventionally initiated by use of a suitable base, such as N,N-diisopropylethylamine (DIPEA), sym-collidine or N-methylmorpholine (NMM).

The cyclized peptides can then be cleaved from solid phase, using any suitable reagent, such as ethylamine in DCM or various combinations of agents, such as trifluoroacetic acid (TFA), tri-isopropylsilane (TIS), dimethoxybenezene (DMB), water and the like. The resulting crude peptide is dried and remaining amino acid side chain protecting groups, if any, are cleaved using any suitable reagent, such as TFA in the presence of water, TIS, 2-mercaptopethane (ME), and/or 1,2-ethanedithiol (EDT). The final product is precipitated by adding cold ether and collected by filtration. Final purification is by reverse phase high performance liquid chromatography (RP-HPLC), using a suitable column, such as a $C_{18}$ column, or other methods of separation or purification, such as methods based on the size or charge of the peptide, can also be employed. Once purified, the peptide can be characterized by any number of methods, such as high performance liquid chromatography (HPLC), amino acid analysis, mass spectrometry, and the like.

For peptides of the present invention which have a C-terminus substituted amide derivative or N-alkyl group, synthesis may proceed by solid phase synthesis commenced from the C-terminal end of the peptide by coupling a protected alpha amino acid to a suitable resin. Such methods for preparing substituted amide derivatives on solid-phase have been described in the art. See, for example, Barn D. R. et al., Synthesis of an array of amides by aluminum chloride assisted cleavage on resin bound esters. *Tetrahedron Letters*, 37:3213-3216 (1996); DeGrado W. F. and Kaiser E. T., Solid-phase synthesis of protected peptides on a polymer bound oxime: Preparation of segments comprising the sequences of a cytotoxic 26-peptide analogue. *J. Org. Chem.*, 47:3258-3261 (1982). Such a starting material can be prepared by attaching an alpha amino-protected amino acid by an ester linkage to a p-benzyloxybenzyl alcohol (Wang) resin or an by amide linkage to a 4-(2',4'-dimethoxylphenyl-aminomethyl-phenoxy (Rink Amide) resin by well known means. The peptide chain is grown with the desired sequence of amino acids. Before cleavage, the peptide is cyclized on the solid phase. Peptides employing a p-benzyloxybenzyl alcohol (Wang) resin may be cleaved from resin by aluminum chloride in DCM, and peptides employing a Rink Amide resin may be cleaved by mixture of TFA, TIS and water.

While synthesis has been described primarily with reference to solid phase Fmoc chemistry, it is to be understood that other chemistries and synthetic methods may be employed to make the cyclic peptides of the invention, such as by way of example and not limitation, methods employing Boc chemistry, solution chemistry, and other chemistries and synthetic methods.

5.1 Salt Form of Cyclic Peptides of the Present Invention.

It shall be understood that as used herein all references to peptides according to the invention, including a specific chemical formula or name, are intended to include all pharmaceutically acceptable salts, solvates, hydrates, polymorphs, prodrugs, metabolites, stereoisomers, and tautomeric isomers thereof.

Cyclic peptides of the present invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids (see "Handbook of Pharmaceutical Salts: Properties, Selection and Use", P. H. Stahl, P. G. Wermuth, IUPAC, Wiley-VCH, 2002). Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When cyclic peptide of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of peptides of the present invention are prepared in a suitable solvent for the peptide and an excess of an acid, such as hydrochloric, hydrobromic, sulfuric, phosphoric, acetic, trifluoroacetic (TFA), citric, tartaric, maleic, succinic or methanesulfonic acid. The acetate, ammonium acetate and TFA acid salt forms are especially useful.

Where peptides of the present invention include an acidic moiety, suitable pharmaceutically acceptable salts may include alkali metal salts, such as sodium or potassium salts, or alkaline earth metal salts, such as calcium or magnesium salts. It is also to be understood that certain peptides of the Formula (I) can exist in solvated forms, including solvates of the free peptide or solvates of a salt of the compound, as well as unsolvated forms. The term "solvate" is used herein to describe a molecular complex comprising the compound of the invention and one or more pharmaceutically acceptable solvent molecules, for example, ethanol. The term "hydrate" is employed when said solvent is water. It is to be understood that all polymorphs, including mixtures of different polymorphs, are included within the scope of the claimed peptides.

5.2 Pharmaceutical Compositions.

The invention provides a pharmaceutical composition that includes one or more cyclic peptides of the present invention and a pharmaceutically acceptable carrier. When formulated with a pharmaceutically acceptable carrier, the compound of the invention may be present in the pharmaceutical composition in a concentration from 0.1 to 99.5%, such as from 0.5 to 95%, by weight of the total composition. The choice of carrier is within the knowledge of a person skilled in the art and depends on, for instance, the mode of administration, the dosage form, and the physical properties of the active compound, such as solubility and stability. The term "carrier" as used herein relates to a therapeutically inactive ingredient. The dosage form may be a solid, semi-solid or liquid system. The formulation may be an immediate and/or modified release, including delayed-, sustained-, pulsed-, controlled-, targeted and programmed release formulation.

The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The cyclic peptide compositions of the present invention may be formulated or compounded into pharmaceutical compositions that include at least one cyclic peptide of the present invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy propyl cellulose (HPC), acacia, polyethylene glycol, mannitol, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, cellulose derivatives, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or sustained-release formulations and additives may be employed, so that the dosage may be formulated so as to provide delivery of a peptide of the present invention over a period of time.

In general, the actual quantity of cyclic peptides of the present invention administered to a patient will vary between fairly wide ranges depending on the mode of administration, the formulation used, and the response desired.

In practical use, the cyclic peptides of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or non-aqueous techniques. The amount of active peptide in such therapeutically useful compositions is such that an effective dosage will be obtained. In another dosage unit form, sublingual constructs may be employed, such as sheets, wafers, tablets or the like.

The tablets, pills, capsules, and the like may also contain a binder such as povidone, gum tragacanth, acacia, corn starch or gelatin; diluents; fillers such as microcrystalline cellulose; excipients such as dicalcium phosphate; a disintegrating agent such as corn starch, potato starch or alginic acid; preservatives; colorants; a lubricant such as magnesium stearate; and a sweetening agent such as sucrose, lactose or saccharin. When a dosage unit form is a capsule, it may contain, in addition to materials of the above type, a liquid carrier such as fatty oil. Various other materials may be utilized as coatings or to is modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

If formulated for oral delivery, the peptide is preferably formulated and made such that it is encased in an enteric protectant, more preferably such that it is not released until the tablet or capsule has transited the stomach, and optionally has further transited a portion of the small intestine. In the context of this application it will be understood that the term enteric coating or material refers to a coating or material that will pass through the stomach essentially intact but will disintegrate after passing through the stomach to release the active drug substance. Materials that may be used includes cellulose acetate phthalate, hydroxypropylmethyl-ethylcellulose succinate, hydroxypropylmethylcellulose phthalate, polyvinyl acetate phthalate, and methacrylic acid-methyl methacrylate copolymer. The enteric coating employed promotes dissolution of the dosage form primarily at a site outside the stomach, and may be selected such that the enteric coating dissolves at a pH of approximately at least 5.5, more preferable at a pH of from about 6.0 to about 8.0.

Any of a variety of permeation enhancers may be employed, to increase uptake in the intestines upon dissolution of the enteric coating. In one aspect, permeation enhancers increase either paracellular or transcellular transport systems. Representative, non-limiting examples of such permeation enhancers include calcium chelators, bile salts (such as sodium cholate), and fatty acids. In some embodiments, peptides or polypeptides that act as substrates for intestinal proteases are further added. Cyclic peptides may also be administered parenterally. Solutions or suspensions of these active peptides may for instance be prepared in water mixed with for instance hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

The cyclic peptides of the present invention may be therapeutically applied by means of nasal administration. By "nasal administration" is meant any form of intranasal administration of any of the cyclic peptides of the present invention. The peptides may be in an aqueous solution, such as a solution including saline, citrate or other common excipients or preservatives. The peptides may also be in a dry or powder formulation.

If in an aqueous solution, the cyclic peptides may be appropriately buffered by means of saline, acetate, phosphate, citrate, acetate or other buffering agents, which may be at any physiologically acceptable pH, such as from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, and the like, a 50 mM solution may be employed. In addition to buffering agents, a suitable preservative may be employed, to prevent or limit bacteria and other microbial growth. One such preservative that may be employed is 0.05% benzalkonium chloride.

In an alternative embodiment, cyclic peptides of the present invention may be administered directly into the lung. Intrapulmonary administration may be performed by means of a metered dose inhaler, a device allowing self-administration of a metered bolus of a peptide of the present invention when actuated by a patient during inspiration. Any of a variety of different techniques may be used to make dry powder microparticles, including but not limited to micro-milling, spray drying and a quick freeze aerosol followed by lyophilization.

The cyclic peptides of the present invention may be therapeutically administered by means of an injection of a sustained release formulation. In general, any of a number of injectable and bioerodible polymers may be employed in a sustained release injectable formulation. Alternatively other sustained release formulations may be employed, including formulations permitting subcutaneous injection, which other formulations may include one or more of nano/microspheres, liposomes, emulsions (such as water-in-oil emulsions), gels, insoluble salts or suspensions in oil The formulation may be such that an injection is required on a daily, weekly, monthly or other periodic basis, depending on the concentration and amount of cyclic peptide, the sustained release rate of the materials employed, and other factors known to those of skill in the art.

5.3 Routes of Administration.

If a composition including one or more peptides of the present invention is administered by injection, the injection may be intravenous, subcutaneous, intramuscular, intraperitoneal or other means known in the art.

The peptides of the present invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptides of invention are introduced across an epidermal layer of cells may be employed. Administration means may thus include administration through mucous membranes, buccal administration, oral administration, dermal administration, inhalation administration, nasal administration, urethral administration, vaginal administration, and the like.

5.4 Therapeutically Effective Amount.

In general, the actual quantity of cyclic peptide of the present invention administered to a patient will vary between fairly wide ranges depending upon the mode of administration, the patient (including weight, sex, health condition and diet), the formulation used, and the response desired. The dosage for treatment is administration, by any of the foregoing means or any other means known in the art, of an amount sufficient to bring about the desired therapeutic effect. The cyclic peptides of the present invention are highly active. For example, the cyclic peptide can be administered (as a single dose or in divided daily doses) at about 0.1, 0.5, 1, 5, 50, 100, 500, 1000 or 5000 ng/kg body weight, depending on the specific peptide selected, the desired therapeutic response, the route of administration, the formulation and other factors known to those of skill in the art.

6.0 Peptides of the Present Invention

In one aspect, the present invention relates to a cyclic peptide of the structural Formula (I):

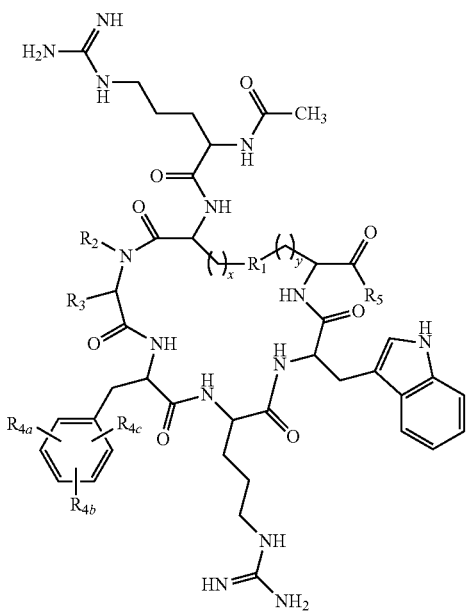

(I)

including all enantiomers, stereoisomers or diastereoisomers thereof, or a pharmaceutically acceptable salt of any of the foregoing, wherein:

$R_1$ is —NH—C(=O)— or —C(=O)—NH—;

$R_2$ is —H or —CH$_2$—, and if $R_2$ is —CH$_2$— forms with $R_3$ a pyrrolidine ring, the pyrrolidine ring optionally substituted with —OH;

$R_3$ is —(CH$_2$)$_2$— if $R_2$ is —CH$_2$—, and otherwise $R_3$ is selected from

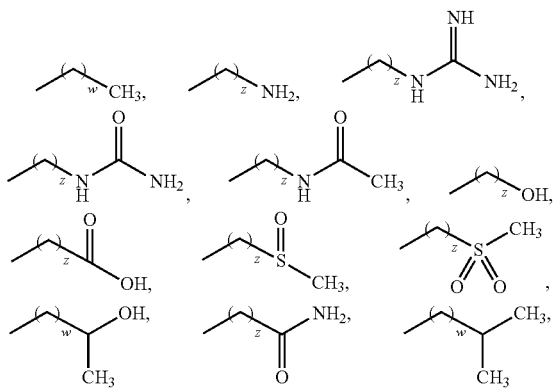

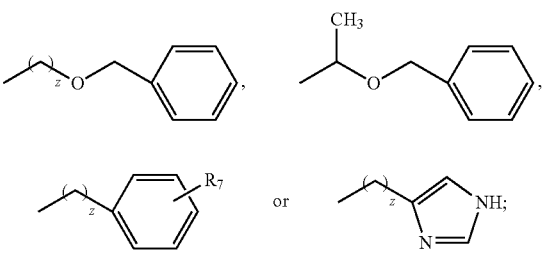

$R_{4a}$, $R_{4b}$ and $R_{4c}$ are each independently selected from hydrogen, halo, (C$_1$-C$_{10}$)alkyl-halo, (C$_1$-C$_{10}$)alkyl-dihalo, (C$_1$-C$_{10}$)alkyl-trihalo, (C$_1$-C$_{10}$)alkyl, (C$_1$-C$_{10}$)alkoxyl, (C$_1$-C$_{10}$)alkylthio, aryl, aryloxy, nitro, nitrile, sulfonamide, amino, monosubstituted amino, disubstituted amino, hydroxy, carboxy, or alkoxy-carbonyl, on the proviso that at least one of $R_{4a}$, $R_{4b}$ and $R_{4c}$ is not hydrogen;

$R_5$ is —OH or —N(R$_{6a}$)(R$_{6b}$);

$R_{6a}$ and $R_{6b}$ are each independently H or a C$_1$ to C$_4$ linear, branched or cyclic alkyl chain;

$R_7$ is —H or —C(=O)—NH$_2$;

w is in each instance independently 0 to 5;

x is 1 to 5;

y is 1 to 5; and z is in each instance independently 1 to 5.

In another aspect, the present invention relates to a cyclic peptide of Formula (I) which is of formula (II):

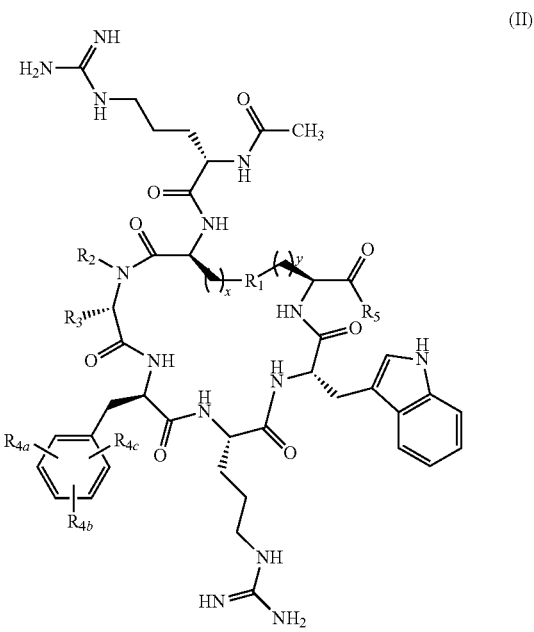

(II)

or a pharmaceutically acceptable salt thereof.

In another aspect, the present invention relates to a cyclic peptide of Formula (I) which is of Formula (III):

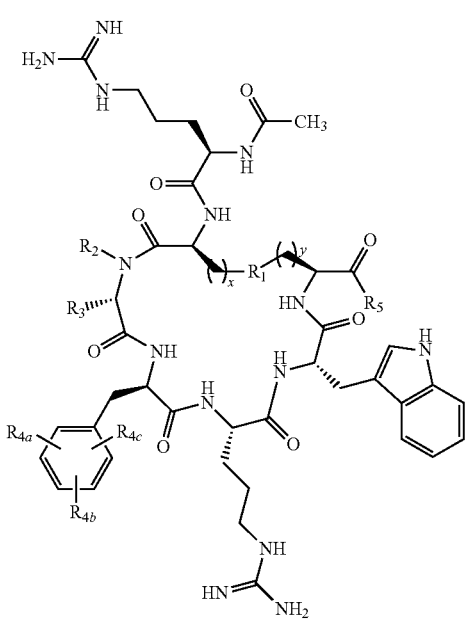

(III)

or a pharmaceutically acceptable salt thereof.

In one aspect, the invention provides a cyclic heptapeptide which contains a core sequence derived from His-Phe-Arg-Trp within the cyclic portion, and where the amino acid in the first position is Arg and is outside the cyclic portion. Without being bound by any theory, the Arg residue is believed to largely contribute to the low activity at MC1-R.

Further, the core sequence in the peptides of Formula I includes a substituted D-Phe. Without being bound by any theory, it is believed that the intrinsic activity may be lowered while substantially maintaining potency by using substituted D-Phe in peptides in accordance with the invention. The peptide called Ref Ex 1 (including unsubstituted D-Phe) in Table 1 can be compared with one or more of Examples 1-5, 9-11, 17, 26 and 27. It may be noted that Table 1 includes mean values.

TABLE 1

| | | | 0.1 ng/mL Doxycycline | |
|---|---|---|---|---|
| | | $K_i$ (nM) | $EC_{50}$ (nM) | Intrinsic activity (%) |
| Ref Ex 1 | Ac-Arg-cyclo(Glu-Dab-D-Phe-Arg-Trp-Orn)-NH$_2$ | 0.65 | 0.33 | 94 |
| Ref Ex 2 | Ac-Arg-cyclo(Glu-Dab-D-Phe-Arg-Trp-Orn)-OH | 8 | 3.0 | 92 |

In a further embodiment of the invention, there are provided peptides according to Formula (I), and in particular Formula (II) or (III), wherein one or more of $R_{4a}$, $R_{4b}$ and $R_{4c}$ are each independently selected from hydrogen, halo, ($C_1$-$C_{10}$)alkyl-halo, ($C_1$-$C_{10}$)alkyl-dihalo, ($C_1$-$C_{10}$)alkyl-trihalo, ($C_1$-$C_{10}$)alkyl, ($C_1$-$C_{10}$)alkoxy, phenyl, nitro, nitrile, amino or hydroxy, on the proviso that at least one of $R_{4a}$, $R_{4b}$ and $R_{4c}$ is not hydrogen.

In a further embodiment of the invention, there are provided peptides according to Formula (I), and in particular Formula (II) or (III), wherein one or more of $R_{4a}$, $R_{4b}$ and $R_{4c}$ are each independently selected from hydrogen, halo, ($C_1$-$C_4$)alkyl-halo, ($C_1$-$C_4$)alkyl-dihalo, ($C_1$-$C_4$)alkyl-trihalo, ($C_1$-$C_4$)alkyl, ($C_1$-$C_4$)alkoxy, phenyl, nitro, nitrile, amino or hydroxy, on the proviso that at least one of $R_{4a}$, $R_{4b}$ and $R_{4c}$ is not hydrogen.

In a further embodiment of the invention, there are provided peptides according to Formula (I), and in particular Formula (II) or (III), wherein one or more of $R_{4a}$, $R_{4b}$ and $R_{4c}$ are each independently selected from

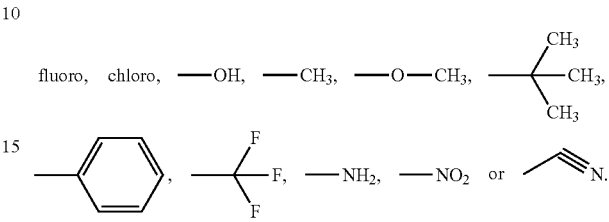

In a further embodiment of the invention, there are provided peptides according to Formula (I), and in particular Formula (II) or (III), wherein one or more of $R_{4a}$, $R_{4b}$ and $R_{4c}$ are each independently selected from hydrogen, halo, ($C_1$-$C_4$)alkyl-halo, ($C_1$-$C_4$)alkyl-dihalo, ($C_1$-$C_4$)alkyl-trihalo, ($C_1$-$C_4$)alkyl, ($C_1$-$C_4$)alkoxy, nitro, nitrile, amino or hydroxy, on the proviso that at least one of $R_{4a}$, $R_{4b}$ and $R_{4c}$ is not hydrogen.

In a further embodiment of the invention, there are provided peptides according to Formula (I), and in particular Formula (II) or (III), wherein one or more of $R_{4a}$, $R_{4b}$ and $R_{4c}$ are each independently selected from

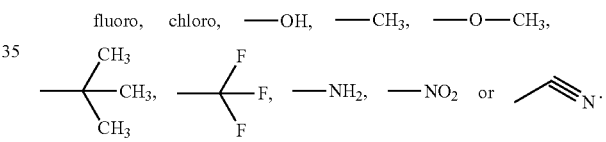

In a further embodiment of the invention, there are provided peptides according to Formula (I), and in particular Formula (II) or (III), wherein $R_{4a}$ is selected from

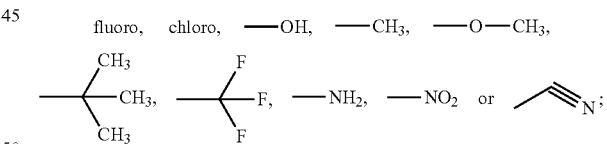

and $R_{4b}$ and $R_{4c}$ are each H.

In a further embodiment of the invention, there are provided peptides according to Formula (I), and in particular Formula (II) or (III), wherein $R_{4a}$ is selected from —C≡N or —F, and $R_{4b}$ and $R_{4c}$ are each H.

In a particular embodiment of the invention, there are provided peptides according to Formula (I), and in particular Formula (II) or (III), wherein $R_{4a}$ is in the 4 position and is —C≡N and $R_{4b}$ and $R_{4c}$ are each H.

In another particular embodiment of the invention, there are provided peptides according to Formula (I), and in particular Formula (II) or (III), wherein $R_{4a}$ is in the 4 position and is —F and $R_{4b}$ and $R_{4c}$ are each H.

The peptides encompassed within Formula (I) contain one or more asymmetric elements such as stereogenic centers, stereogenic axes and the like, so that the peptides encompassed within Formula (I) can exist in different stereoisomeric forms. For both specific and generically described peptides, including the peptides encompassed within Formula (I), all forms of isomers at all chiral or other isomeric centers, including enantiomers and diastereomers, are intended to be covered herein. The peptides of the invention each include multiple chiral centers, and may be used as a racemic mixture or an enantiomerically enriched mixture, in addition to use of the peptides of the invention in enantiopure preparations. Typically, the peptides of the invention will be synthesized with the use of chirally pure reagents, such as specified L- or D-amino acids, using reagents, conditions and methods such that enantiomeric purity is maintained, but it is possible and contemplated that racemic mixtures may be made. Such racemic mixtures may optionally be separated using well-known techniques and an individual enantiomer may be used alone. In cases and under specific conditions of temperature, solvents and pH wherein peptides may exist in tautomeric forms, each tautomeric form is contemplated as being included within this invention whether existing in equilibrium or predominantly in one form. Thus a single enantiomer of a peptide of Formula (I), which is an optically active form, can be obtained by asymmetric synthesis, synthesis from optically pure precursors, or by resolution of the racemates.

The peptides of formulas (II) and (III) are specific stereoisomeric forms of the peptides of Formula (I), but the invention should not be construed as being limited to the stereoisomeric forms encompassed by formulas (II) and (III).

The invention is further intended to include prodrugs of the present peptides, which on administration undergo chemical conversion by metabolic processes before becoming active pharmacological peptides. In general, such prodrugs will be functional derivatives of the present peptides, which are readily convertible in vivo into a peptide of Formula (I). Prodrugs are any covalently bonded compounds, which release the active parent peptide drug of Formula (I) in vivo. Conventional procedures for the selection and preparation of suitable prodrug derivatives are described, for example, in "Design of Prodrugs", ed. H. Bundgaard, Elsevier, 1985. Typical examples of prodrugs have biologically labile protecting groups on a functional moiety, such as for example by esterification of hydroxyl, carboxyl or amino functions. Thus by way of example and not limitation, a prodrug includes peptides of Formula (I) wherein an ester prodrug form is employed, such as, for example, lower alkyl esters of the R group of Formula (I), such as where R is —OH, which lower alkyl esters may include from 1-8 carbons in an alkyl radical or aralkyl esters which have 6-12 carbons in an aralkyl radical. Broadly speaking, prodrugs include compounds that can be oxidized, reduced, aminated, deaminated, hydroxylated, dehydroxylated, hydrolyzed, dehydrolyzed, alkylated, dealkylated, acylated, deacylated, phosphorylated or dephosphorylated to produce an active parent peptide drug of Formula (I) in vivo.

Certain modifications of peptides of Formula I may be made in order to enhance the half-life of the peptide (see G. Pasuta and F. M. Veronese (2007) "Polymer-drug conjugation, recent achievements and general strategies" *Progress in Polymer Science* 32 (8-9): 933-961).

The subject invention also includes peptides which are identical to those recited in Formula (I), but for the fact that one or more atoms depicted in Formula (I) are replaced by an atom having an atomic mass or mass number different from the atomic mass or mass number usually found in nature. Examples of isotopes that can be incorporated into peptides of the invention include isotopes of hydrogen, carbon, nitrogen and oxygen, such as $^2$H, $^3$H, $^{13}$C, $^{14}$C, $^{15}$N, $^{18}$O and $^{17}$O, respectively. Peptides of the present invention and pharmaceutically acceptable salts or solvates of said peptides which contain the aforementioned isotopes and/or other isotopes of other atoms are within the scope of this invention. Certain isotopically-labeled peptides of the present invention, for example those into which radioactive isotopes such as $^3$H and $^{14}$C are incorporated, may have use in a variety of assays, such as in drug and/or substrate tissue distribution assays. Substitution with heavier isotopes, such as substitution of one or more hydrogen atoms with deuterium ($^2$H), can provide pharmacological advantages in some instances, including increased metabolic stability. Isotopically labeled peptides of Formula (I) can generally be prepared by substituting an isotopically labeled reagent for a non-isotopically labeled reagent.

In one embodiment of the peptides according to Formula (I), and in particular Formula (II) or (III), $R_1$ is —C(═O)—NH—, x is 2 and y is 3.

In another embodiment of the peptides according to Formula (I), and in particular Formula (II) or (III), $R_1$ is —C(═O)—NH—, x is 1 and y is 4.

In another embodiment of the peptides according to Formula (I), and in particular Formula (II) or (III), $R_1$ is —NH—C(═O)—, x is 3 and y is 2.

In still another embodiment of the peptides according to the Formula (I), and in particular Formula (II) or (III), $R_1$ is —NH—C(═O)—, x is 4 and y is 1.

In a particular embodiment of the peptides according to the Formula (I), and in particular Formula (II) or (III), $R_1$ is —C(═O)—NH—, x is 2 and y is 3, or alternatively $R_1$ is —NH—C(═O)—, x is 3 and y is 2. More specifically, $R_1$ is —C(═O)—NH—, x is 2 and y is 3. It has surprisingly and unexpectedly been found that peptides according to the invention having a lactam bridge wherein the amide bond is positioned by means of the side chain of Glu (at the N-terminus end of the cyclic portion) and the side chain of Orn (at the C-terminus end of the cyclic portion) generally provides improved potency as determined by $EC_{50}$, in particular in the herein described low density hMC4-R system, compared to peptides wherein the amide bond is positioned by means of the side chains of Asp and Lys, but which are otherwise identical. This discovery is contrary to assertions in the prior art that the location and direction of an amide bond in the lactam bridge of melanocortin receptor specific peptides is of little importance for activity and does not interact with receptors. See, for example, Bednarek M A et al., Potent and selective peptide agonists of α-melanotropin action at human melanocortin receptor 4: their synthesis and biological evaluation in vitro. *Biochem. Biophys. Res. Comm.* 286:641-645 (2001).

In an embodiment of the peptides according to Formula (I), and in particular Formula (II) or (III), $R_2$ is —H or —CH$_2$—, and if $R_2$ is —CH$_2$— forms with $R_3$ a pyrrolidine ring, the pyrrolidine ring optionally substituted with —OH;

$R_3$ is —(CH$_2$)$_2$— if $R_2$ is —CH$_2$—, and otherwise $R_3$ is selected from

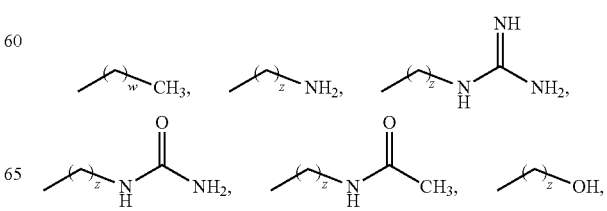

-continued

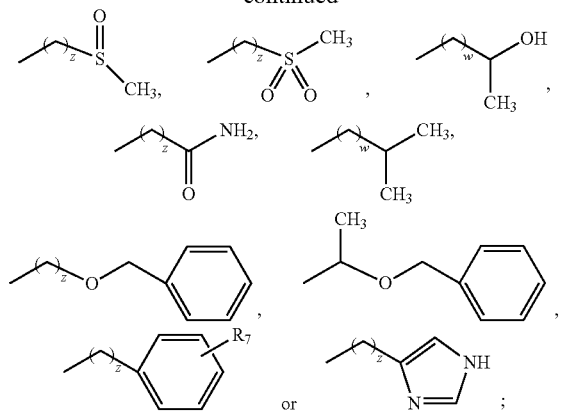

wherein w is in each instance independently selected from 0 to 5, and z is in each instance independently selected from 1 to 5.

In an embodiment of the peptides according to Formula (I), and in particular Formula (II) or (III), $R_2$ is —H or —$CH_2$—, and if $R_2$ is —$CH_2$— forms with $R_3$ a pyrrolidine ring, the pyrrolidine ring optionally substituted with —OH;

$R_3$ is —$(CH_2)_2$— if $R_2$ is —$CH_2$—, and otherwise $R_3$ is selected from

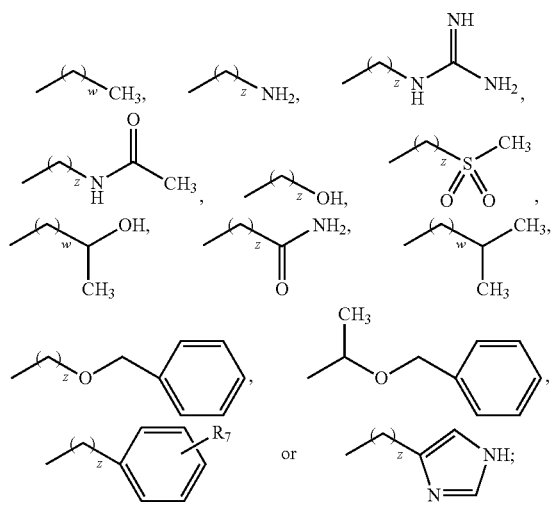

wherein w is in each instance independently selected from 0 to 5, and z is in each instance independently selected from 1 to 5.

In an embodiment of the peptides according to Formula (I), and in particular Formula (II) or (III), $R_2$ is H.

In an embodiment of the peptides according to Formula (I), and in particular Formula (II) or (III), $R_2$ is H or —$CH_2$—, and if $R_2$ is —$CH_2$— forms with $R_3$ a pyrrolidine ring, the pyrrolidine ring optionally substituted with —OH; and $R_3$ is —$(CH_2)_2$— if $R_2$ is —$CH_2$—, and otherwise $R_3$ is selected from

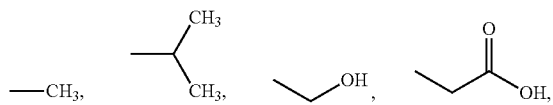

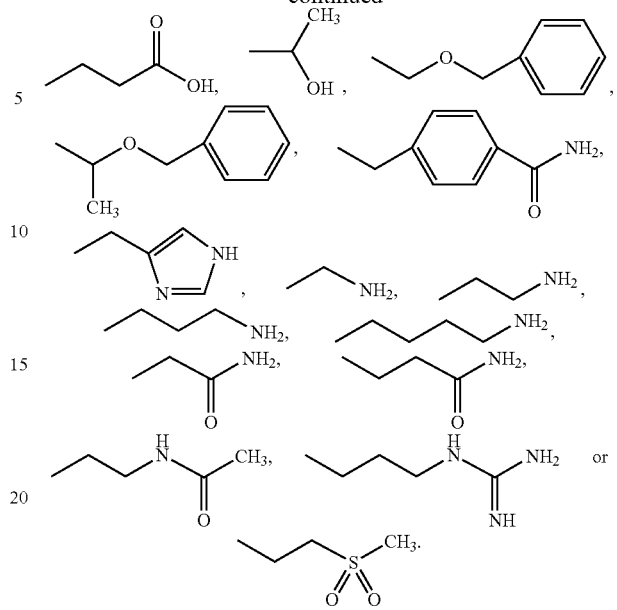

Without being bound by any theory, replacing His by a non-aromatic amino acid, in particular a non-polar, small aliphatic amino acid, such as Pro or Ala, or a polar uncharged or charged amino acid, such as Lys, Asp, Gln and Asn, is believed to contribute to attenuation of blood pressure effects. Thus, the His position in the core sequence may for instance be replaced by Dab, Dab(Acetyl), Ser, Met(O), Met($O_2$), Thr, Hyp, Gln, Pro, Ala, Asn, Cit, Orn, Dap, Lys, or Arg, in particular Pro, Asn or Gln.

Thus, in a further embodiment of the invention, there are provided peptides of Formula (I), in particular of Formula (II) or (III), wherein $R_2$ is —H or —$CH_2$—, and if $R_2$ is —$CH_2$— forms with $R_3$ a pyrrolidine ring, the pyrrolidine ring optionally substituted with —OH; and $R_3$ is —$(CH_2)_2$— if $R_2$ is —$CH_2$—, and otherwise $R_3$ is selected from

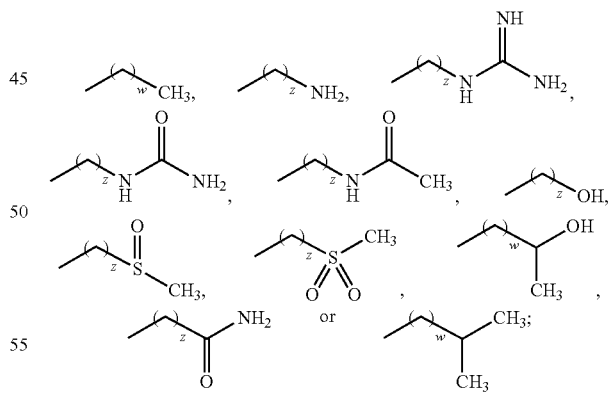

wherein w is in each instance independently selected from 0 to 5, and z is in each instance independently selected from 1 to 5.

In a further embodiment of the invention, there are provided peptides of Formula (I), in particular of Formula (II) or (III), wherein $R_2$ is —H or —$CH_2$—, and if $R_2$ is —$CH_2$— forms with $R_3$ a pyrrolidine ring, the pyrrolidine ring optionally substituted with —OH; and $R_3$ is —$(CH_2)_2$— if $R_2$ is —$CH_2$—, and otherwise $R_3$ is selected from

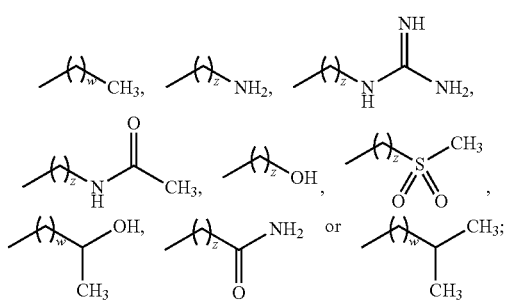

wherein w is in each instance independently selected from 0 to 5, and z is in each instance independently selected from 1 to 5.

In a particular embodiment of the invention, there are provided peptides of Formula (I), in particular of Formula (II) or (III), wherein $R_2$ is —H or —$CH_2$—, and if $R_2$ is —$CH_2$— forms with $R_3$ a pyrrolidine ring, the pyrrolidine ring optionally substituted with —OH; and $R_3$ is —$(CH_2)_2$— if $R_2$ is —$CH_2$—, and otherwise $R_3$ is selected from

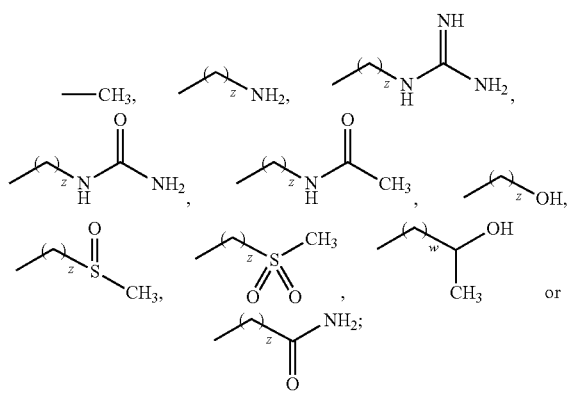

wherein w is in each instance independently selected from 0 to 5, in particular 0 to 2, such as 0, and z is in each instance independently selected from 1 to 5, in particular 1 to 4.

In a further particular embodiment of the invention, there are provided peptides of Formula (I), in particular of Formula (II) or (III), wherein $R_2$ is —H or —$CH_2$—, and if $R_2$ is —$CH_2$— forms with $R_3$ a pyrrolidine ring, the pyrrolidine ring optionally substituted with —OH; and $R_3$ is —$(CH_2)_2$— if $R_2$ is —$CH_2$—, and otherwise $R_3$ is selected from

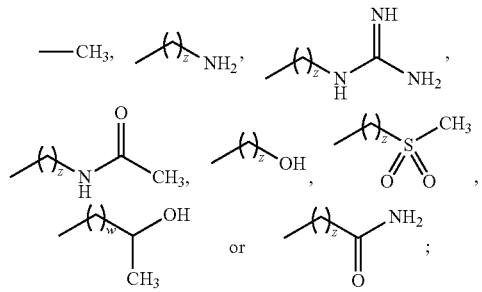

wherein w is in each instance independently selected from 0 to 5, in particular 0 to 2, such as 0, and z is in each instance independently selected from 1 to 5, in particular 1 to 4.

In further embodiments of the peptides according to Formula (I), and in particular Formula (II) or (III), $R_2$ is H or —$CH_2$—, and if $R_2$ is —$CH_2$— forms with $R_3$ a pyrrolidine ring, the pyrrolidine ring optionally substituted with —OH; and $R_3$ is selected from

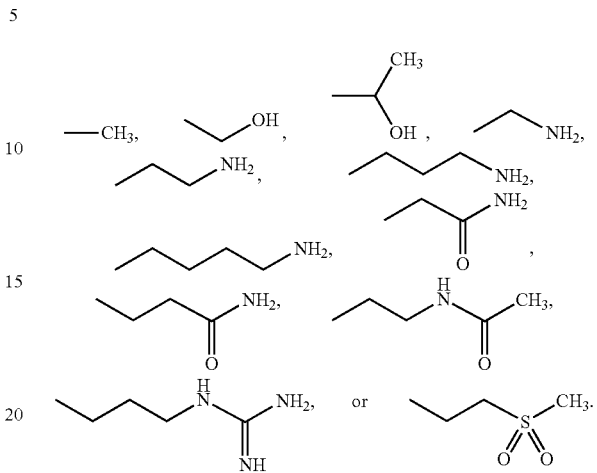

In another embodiment of the invention, there are provided peptides of Formula (I), in particular of Formula (II) or (III), wherein $R_2$ is H and $R_3$ is selected from

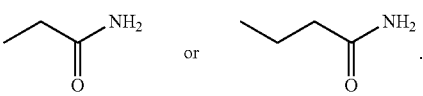

In another embodiment of the invention, there are provided peptides of Formula (I), in particular of Formula (II) or (III), wherein $R_2$ is H and $R_3$ is selected from

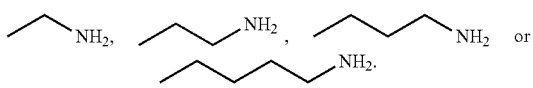

In another embodiment of the invention, there are provided peptides of Formula (I), and in particular Formula (II) or (III), wherein $R_2$ is —$CH_2$— and $R_3$ is —$(CH_2)_2$—, $R_2$ and $R_3$ together forming an unsubstituted pyrrolidine ring.

In still another embodiment of the invention, there are provided peptides of Formula (I), and in particular Formula (II) or (III), wherein $R_2$ is —$CH_2$— and $R_3$ is —$(CH_2)_2$—, $R_2$ and $R_3$ together forming an pyrrolidine ring substituted with —OH. In a further embodiment of the peptides according to Formula (I), and in particular Formula (II) or (III), $R_5$ is —$NH_2$ or —OH.

In a specific embodiment of the peptides according to Formula (I), and in particular Formula (II) or (III), $R_5$ is —$NH_2$.

One or more of the above embodiments may be combined to provide further specific embodiments of the peptides according to the invention.

Thus, in a particular embodiment of the invention, there are provided peptides according to Formula (I), in particular Formula (II) or (III), wherein $R_1$ is —C(=O)—NH—, x is 2 and y is 3;

$R_2$ is —H or —$CH_2$—, and if $R_2$ is —$CH_2$— forms with $R_3$ a pyrrolidine ring, the pyrrolidine ring optionally substituted with —OH;

$R_3$ is —$(CH_2)_2$— if $R_2$ is —$CH_2$—, and otherwise $R_3$ is selected from

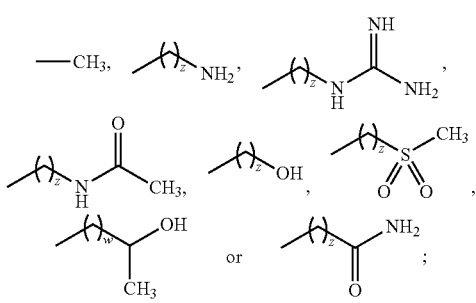

w is in each instance independently selected from 0 to 5;
z is in each instance independently selected from 1 to 5;
one or more of $R_{4a}$, $R_{4b}$ and $R_{4c}$ are each independently selected from

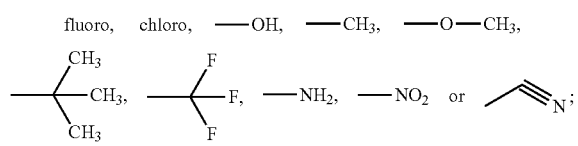

and
$R_5$ is —$NH_2$ or —OH.

Some specific peptides of the invention are one or more of the following:

Ac-Arg-cyclo(Glu-Dab-D-Phe(2-Cl)-Arg-Trp-Orn)-NH$_2$; (SEQ ID NO: 6)

Ac-Arg-cyclo(Glu-Dab-D-Phe(3-Cl)-Arg-Trp-Orn)-NH$_2$; (SEQ ID NO: 7)

Ac-Arg-cyclo(Glu-Dab-D-Phe(4-Cl)-Arg-Trp-Orn)-NH$_2$; (SEQ ID NO: 8)

Ac-Arg-cyclo(Glu-Dab-D-Phe(2,4-diCl)-Arg-Trp-Orn)-NH$_2$; (SEQ ID NO: 9)

Ac-Arg-cyclo(Glu-Dab-D-Phe(3,4-diCl)-Arg-Trp-Orn)-NH$_2$; (SEQ ID NO: 10)

Ac-Arg-cyclo(Glu-Dab-D-Phe(3-CN)-Arg-Trp-Orn)-NH$_2$; (SEQ ID NO: 11)

Ac-Arg-cyclo(Glu-Dab-D-Phe(4-CN)-Arg-Trp-Orn)-NH$_2$; (SEQ ID NO: 12)

Ac-Arg-cyclo(Glu-Dab-D-Tyr-Arg-Trp-Orn)-NH$_2$; (SEQ ID NO: 13)

Ac-Arg-cyclo(Glu-Dab-D-Phe(2-F)-Arg-Trp-Orn)-NH$_2$; (SEQ ID NO: 14)

Ac-Arg-cyclo(Glu-Dab-D-Phe(3-F)-Arg-Trp-Orn)-NH$_2$; (SEQ ID NO: 15)

Ac-Arg-cyclo(Glu-Dab-D-Phe(4-F)-Arg-Trp-Orn)-NH$_2$; (SEQ ID NO: 16)

Ac-Arg-cyclo(Glu-Dab-D-Phe(2-CN)-Arg-Trp-Orn)-NH$_2$; (SEQ ID NO: 17)

Ac-Arg-cyclo(Glu-Dab-D-Phe(2-CF$_3$)-Arg-Trp-Orn)-NH$_2$; (SEQ ID NO: 18)

Ac-Arg-cyclo(Glu-Dab-D-Phe(3-CF$_3$)-Arg-Trp-Orn)-NH$_2$; (SEQ ID NO: 19)

Ac-Arg-cyclo(Glu-Dab-D-Phe(4-Me)-Arg-Trp-Orn)-NH$_2$; (SEQ ID NO: 20)

Ac-Arg-cyclo(Glu-Dab-D-Phe(4-OMe)-Arg-Trp-Orn)-NH$_2$; (SEQ ID NO: 21)

Ac-Arg-cyclo(Glu-Dab-D-Phe(3,5-diF)-Arg-Trp-Orn)-NH$_2$; (SEQ ID NO: 22)

Ac-Arg-cyclo(Glu-Dab-D-Phe(2-Me)-Arg-Trp-Orn)-NH$_2$; (SEQ ID NO: 23)

Ac-Arg-cyclo(Glu-Dab-D-Phe(3-Me)-Arg-Trp-Orn)-NH$_2$; (SEQ ID NO: 24)

Ac-Arg-cyclo(Glu-Dab-D-Phe(4-CF$_3$)-Arg-Trp-Orn)-NH$_2$; (SEQ ID NO: 25)

Ac-Arg-cyclo(Glu-Dab-D-Phe(2,4-diMe)-Arg-Trp-Orn)-NH$_2$; (SEQ ID NO: 26)

Ac-Arg-cyclo(Glu-Dab-D-Phe(2-NO$_2$)-Arg-Trp-Orn-NH$_2$; (SEQ ID NO: 27)

Ac-Arg-cyclo(Glu-Dab-D-Phe(3-NO$_2$)-Arg-Trp-Orn)-NH$_2$; (SEQ ID NO: 28)

Ac-Arg-cyclo(Glu-Dab-D-Phe(4-NO$_2$)-Arg-Trp-Orn)-NH$_2$; (SEQ ID NO: 29)

Ac-Arg-cyclo(Glu-Dab-D-Phe(3,4-diOMe)-Arg-Trp-Orn)-NH$_2$; (SEQ ID NO: 30)

Ac-Arg-cyclo(Glu-Dab-D-Phe(3,4-diF)-Arg-Trp-Orn)-NH$_2$; (SEQ ID NO: 31)

Ac-Arg-cyclo(Glu-Dab-D-Phe(3,4,5-triF)-Arg-Trp-Orn)-NH$_2$; (SEQ ID NO: 32)

Ac-Arg-cyclo(Glu-Dab-D-Phe(4-NH$_2$)-Arg-Trp-Orn)-NH$_2$; (SEQ ID NO: 33)

Ac-Arg-cyclo(Glu-Dab-D-Phe(4-tBu)-Arg-Trp-Orn)-NH$_2$; (SEQ ID NO: 35)

Ac-Arg-cyclo(Glu-Ser-D-Phe(2-Cl)-Arg-Trp-Orn)-NH$_2$; (SEQ ID NO: 36)

Ac-Arg-cyclo(Glu-Thr-D-Phe(2-Cl)-Arg-Trp-Orn)-NH$_2$; (SEQ ID NO: 37)

Ac-Arg-cyclo(Glu-Hyp-D-Phe(2-Cl)-Arg-Trp-Orn)-NH$_2$; (SEQ ID NO: 38)

Ac-Arg-cyclo(Glu-Gln-D-Phe(2-Cl)-Arg-Trp-Orn)-NH$_2$; (SEQ ID NO: 39)

(SEQ ID NO: 40)
Ac-Arg-cyclo(Glu-Ser-D-Phe(3-Cl)-Arg-Trp-Orn)-NH₂;

(SEQ ID NO: 41)
Ac-Arg-cyclo(Glu-Thr-D-Phe(3-Cl)-Arg-Trp-Orn)-NH₂;

(SEQ ID NO: 42)
Ac-Arg-cyclo(Glu-Hyp-D-Phe(3-Cl)-Arg-Trp-Orn)-NH₂;

(SEQ ID NO: 43)
Ac-Arg-cyclo(Glu-Gln-D-Phe(3-Cl)-Arg-Trp-Orn)-NH₂;

(SEQ ID NO: 44)
Ac-Arg-cyclo(Glu-Pro-D-Phe(4-CN)-Arg-Trp-Orn)-NH₂;

(SEQ ID NO: 45)
Ac-Arg-cyclo(Glu-Hyp-D-Phe(4-CN)-Arg-Trp-Orn)-NH₂;

(SEQ ID NO: 46)
Ac-Arg-cyclo(Glu-Ala-D-Phe(4-CN)-Arg-Trp-Orn)-NH₂;

(SEQ ID NO: 48)
Ac-Arg-cyclo(Glu-Asn-D-Phe(4-CN)-Arg-Trp-Orn)-NH₂;

(SEQ ID NO: 49)
Ac-Arg-cyclo(Glu-Thr-D-Phe(4-CN)-Arg-Trp-Orn)-NH₂;

(SEQ ID NO: 50)
Ac-Arg-cyclo(Glu-Ser-D-Phe(4-CN)-Arg-Trp-Orn)-NH₂;

(SEQ ID NO: 51)
Ac-Arg-cyclo(Glu-Gln-D-Phe(4-CN)-Arg-Trp-Orn)-NH₂;

(SEQ ID NO: 54)
Ac-Arg-cyclo(Glu-Orn-D-Phe(2-Cl)-Arg-Trp-Orn)-OH;

(SEQ ID NO: 60)
Ac-Arg-cyclo(Glu-Orn-D-Phe(3-Cl)-Arg-Trp-Orn)-OH;

(SEQ ID NO: 61)
Ac-Arg-cyclo(Glu-Dab(Acetyl)-D-Phe(2-Cl)-Arg-Trp-Orn)-NH₂;

(SEQ ID NO: 63)
Ac-Arg-cyclo(Glu-Ser-D-Phe(2-F)-Arg-Trp-Orn)-NH₂;

(SEQ ID NO: 64)
Ac-Arg-cyclo(Glu-Gln-D-Phe(2-F)-Arg-Trp-Orn)-NH₂;

(SEQ ID NO: 65)
Ac-Arg-cyclo(Glu-Hyp-D-Phe(4-F)-Arg-Trp-Orn)-NH₂;

(SEQ ID NO: 66)
Ac-Arg-cyclo(Glu-Dap-D-Phe(3-Cl)-Arg-Trp-Orn)-NH₂;

(SEQ ID NO: 67)
Ac-Arg-cyclo(Glu-Dap-D-Phe(2-Cl)-Arg-Trp-Orn)-NH₂;

(SEQ ID NO: 69)
Ac-Arg-cyclo(Glu-Hyp-D-Phe(2-F)-Arg-Trp-Orn)-NH₂;

(SEQ ID NO: 70)
Ac-Arg-cyclo(Glu-Ser-D-Phe(4-F)-Arg-Trp-Orn)-NH₂;

(SEQ ID NO: 71)
Ac-Arg-cyclo(Glu-Pro-D-Phe(2-F)-Arg-Trp-Orn)-NH₂;

(SEQ ID NO: 72)
Ac-Arg-cyclo(Glu-Pro-D-Phe(4-F)-Arg-Trp-Orn)-NH₂;

(SEQ ID NO: 73)
Ac-Arg-cyclo(Glu-Met(O₂)-D-Phe(4-F)-Arg-Trp-Orn)-NH₂;

(SEQ ID NO: 74)
Ac-Arg-cyclo(Glu-Asn-D-Phe(4-F)-Arg-Trp-Orn)-NH₂;

(SEQ ID NO: 78)
Ac-Arg-cyclo(Glu-Asn-D-Phe(2-Me)-Arg-Trp-Orn)-NH₂;

(SEQ ID NO: 81)
Ac-Arg-cyclo(Glu-Asn-D-Phe(3,5-diF)-Arg-Trp-Orn)-NH₂;

(SEQ ID NO: 89)
Ac-Arg-cyclo(Glu-Asn-D-Phe(2-Cl)-Arg-Trp-Orn)-NH₂;

(SEQ ID NO: 90)
Ac-Arg-cyclo(Glu-Asn-D-Phe(4-CN)-Arg-Trp-Orn)-OH;

(SEQ ID NO: 91)
Ac-Arg-cyclo(Glu-Gln-D-Phe(4-CN)-Arg-Trp-Orn)-OH;

(SEQ ID NO: 92)
Ac-Arg-cyclo(Glu-Dab-D-Phe(3-OMe)-Arg-Trp-Orn)-NH₂;

(SEQ ID NO: 93)
Ac-Arg-cyclo(Glu-Pro-D-Phe(2-Cl)-Arg-Trp-Orn)-NH₂;

(SEQ ID NO: 97)
Ac-Arg-cyclo(Glu-Gln-D-Phe(4-F)-Arg-Trp-Orn)-NH₂;

(SEQ ID NO: 100)
Ac-Arg-cyclo(Glu-Asn-D-Phe(3,4,5-triF)-Arg-Trp-Orn)-NH₂;

(SEQ ID NO: 102)
Ac-Arg-cyclo(Glu-Gln-D-Phe(3,4,5-triF)-Arg-Trp-Orn)-NH₂;

(SEQ ID NO: 104)
Ac-Arg-cyclo(Glu-Arg-D-Phe(3-Cl)-Arg-Trp-Orn)-NH₂;

(SEQ ID NO: 105)
Ac-Arg-cyclo(Glu-Lys-D-Phe(3-Cl)-Arg-Trp-Orn)-NH₂;

(SEQ ID NO: 106)
Ac-Arg-cyclo(Glu-Orn-D-Phe(3-Cl)-Arg-Trp-Orn)-NH₂

(SEQ ID NO: 107)
Ac-Arg-cyclo(Glu-Pro-D-Phe(4-F)-Arg-Trp-Orn)-OH;

(SEQ ID NO: 111)
Ac-Arg-cyclo(Glu-Asp-D-Phe(4-CN)-Arg-Trp-Orn)-NH₂;

(SEQ ID NO: 112)
Ac-Arg-cyclo(Glu-Asp-D-Phe(4-CN)-Arg-Trp-Orn)-OH;

(SEQ ID NO: 113)
Ac-Arg-cyclo(Glu-Glu-D-Phe(4-CN)-Arg-Trp-Orn)-NH₂;

(SEQ ID NO: 114)
Ac-Arg-cyclo(Glu-Glu-D-Phe(4-CN)-Arg-Trp-Orn)-OH;

(SEQ ID NO: 115)
Ac-Arg-cyclo(Glu-Gln-D-Phe(2-Me)-Arg-Trp-Orn)-NH₂;

(SEQ ID NO: 119)
Ac-Arg-cyclo(Glu-Gln-D-Phe(2-CF₃)-Arg-Trp-Orn)-NH₂;

(SEQ ID NO: 121)
Ac-Arg-cyclo(Glu-Asn-D-Phe(2-CF₃)-Arg-Trp-Orn)-NH₂;

pharmaceutically acceptable salt of any of the foregoing. Particularly, the invention relates to:

(SEQ ID NO: 48)
Ac-Arg-cyclo(Glu-Asn-D-Phe(4-CN)-Arg-Trp-Orn)-NH₂;

-continued (SEQ ID NO: 74)
Ac-Arg-cyclo(Glu-Asn-D-Phe(4-F)-Arg-Trp-Orn)-NH$_2$;

(SEQ ID NO: 90)
Ac-Arg-cyclo(Glu-Asn-D-Phe(4-CN)-Arg-Trp-Orn)-OH, or a pharmaceutically acceptable salt of any of the foregoing.
Particularly, the invention also relates to:

(SEQ ID NO: 51)
Ac-Arg-cyclo(Glu-Gln-D-Phe(4-CN)-Arg-Trp-Orn)-NH$_2$;

(SEQ ID NO: 91)
Ac-Arg-cyclo(Glu-Gln-D-Phe(4-CN)-Arg-Trp-Orn)-OH;

(SEQ ID NO: 97)
Ac-Arg-cyclo(Glu-Gln-D-Phe(4-F)-Arg-Trp-Orn)-NH$_2$, or a pharmaceutically acceptable salt of any of the foregoing.
Particularly, the invention also relates to:

(SEQ ID NO: 44)
Ac-Arg-cyclo(Glu-Pro-D-Phe(4-CN)-Arg-Trp-Orn)-NH$_2$;

(SEQ ID NO: 72)
Ac-Arg-cyclo(Glu-Pro-D-Phe(4-F)-Arg-Trp-Orn)-NH$_2$, (SEQ ID NO: 107)
Ac-Arg-cyclo(Glu-Pro-D-Phe(4-F)-Arg-Trp-Orn)-OH;

or a pharmaceutically acceptable salt of any of the foregoing.
Some further specific peptides of the invention are:

(SEQ ID NO: 75)
Ac-Arg-cyclo(Orn-Asn-D-Phe(4-F)-Arg-Trp-Glu)-NH$_2$;

(SEQ ID NO: 76)
Ac-Arg-cyclo(Orn-Asn-D-Phe(2-F)-Arg-Trp-Glu)-NH$_2$;

(SEQ ID NO: 77)
Ac-Arg-cyclo(Orn-Asn-D-Phe(3-Me)-Arg-Trp-Glu)-NH$_2$;

(SEQ ID NO: 79)
Ac-Arg-cyclo(Orn-Asn-D-Phe(2-Me)-Arg-Trp-Glu)-NH$_2$;

(SEQ ID NO: 80)
Ac-Arg-cyclo(Orn-Asn-D-Phe(3,4-diF)-Arg-Trp-Glu)-NH$_2$;

(SEQ ID NO: 82)
Ac-Arg-cyclo(Orn-Asn-D-Phe(3,5-diF)-Arg-Trp-Glu)-NH$_2$;

(SEQ ID NO: 96)
Ac-Arg-cyclo(Orn-Asn-D-Phe(4-CN)-Arg-Trp-Glu)-NH$_2$;

(SEQ ID NO: 99)
Ac-Arg-cyclo(Orn-Gln-D-Phe(4-CN)-Arg-Trp-Glu)-NH$_2$;

(SEQ ID NO: 101)
Ac-Arg-cyclo(Orn-Asn-D-Phe(3,4,5-triF)-Arg-Trp-Glu)-NH$_2$;

(SEQ ID NO: 103)
Ac-Arg-cyclo(Orn-Gln-D-Phe(3,4,5-triF)-Arg-Trp-Glu)-NH$_2$;

(SEQ ID NO: 110)
Ac-Arg-cyclo(Orn-Pro-D-Phe(2-F)-Arg-Trp-Glu)-NH$_2$;

(SEQ ID NO: 116)
Ac-Arg-cyclo(Orn-Gln-D-Phe(2-Me)-Arg-Trp-Glu)-NH$_2$;

(SEQ ID NO: 117)
Ac-Arg-cyclo(Orn-Gln-D-Phe(2-Cl)-Arg-Trp-Glu)-NH$_2$;

(SEQ ID NO: 118)
Ac-Arg-cyclo(Orn-Asn-D-Phe(2-Cl)-Arg-Trp-Glu)-NH$_2$;

(SEQ ID NO: 120)
Ac-Arg-cyclo(Orn-Gln-D-Phe(2-CF$_3$)-Arg-Trp-Glu)-NH$_2$;

(SEQ ID NO: 122)
Ac-Arg-cyclo(Orn-Asn-D-Phe(2-CF$_3$)-Arg-Trp-Glu)-NH$_2$;

or a pharmaceutically acceptable salt of any of the foregoing.

6.1 Specific Peptides.

Peptides of the following structures were synthesized by the general methods described above, and except where indicated MC1-R Ki and MC4-R Ki values for each peptide were determined in competitive binding assays using [I$^{125}$]-NDP-α-MSH as described in 7.1 below. All peptides were prepared in the TFA acid salt form, except for the peptides of Examples 43, 46 and 67, which were prepared in the acetate salt form.

The syntheses of some specific peptides of the invention are illustrated below. These peptides were prepared using solid phase peptide synthesis by means of a Symphony Multiplex Peptide Synthesizer (Rainin Instrument Company/Protein Technologies Inc) automated peptide synthesizer.

Step 1: Coupling of Orn

The Sierber resin 9-Fmoc-Aminoxanthen-3-yloxy-polystyrene resin (0.39 mol/g, ChemPep Inc., #151902) was swelled in 3×5 mL of DMF for 10 min. Thereafter, Fmoc was deprotected using 2×5 mL of 20% piperidine in DMF for 10 min. The resin was then washed in 6×5 mL DMF for 30 sec. 5 mL of 200 mM Fmoc-Orn(Alloc)-OH in DMF and 5 mL 200 mM HBTU containing 400 mM NMM in DMF was added and after 30 min the resin was washed with 3×5 mL DMF for 30 sec.

Step 2: Coupling of Next 6 Amino Acids (AA)

The resin from step 1 was first swelled in 3×5 mL of DMF for 30 sec, Fmoc was deprotected using 2×5 mL of 20% piperidine in DMF for 10 min and then washed with 6×5 mL DMF for 30 sec. 5 mL of 200 mM Fmoc-AA-OH solution and 5 mL 200 mM HBTU containing 400 mM NMM in DMF was added and after 30 min the resin was washed with 3×5 mL DMF for 30 sec.

This step was repeated for each amino acid (AA).

Step 3: Acetylation

Fmoc was deprotected using 2×5 mL of 20% piperidine in DMF for 10 min and the resin was then washed with 3×5 mL DMF for 30 sec. Thereafter, 5 mL of 50% Ac$_2$O/DMF solution was added and after 30 mM the peptide resin was washed with 3×5 mL DMF for 30 sec and 6×5 mL DCM for 30 sec.

Step 4: Allyl/Alloc Deprotection

The peptide resin (0.6 mmol) was mixed with phenylsilane (Oakwood Chemical, #S13600) (20 eq.) in 20 mL of DCM and bubbled with nitrogen for 5 min.

Tetrakis(triphenylphosphine)-palladium(0) (Strem Chemicals, Inc., #46-2150) (0.2 eq.) was added and the mixture was agitated with nitrogen for 1 hour. The procedure was repeated one time for 1 hour and an additional time for 30 min with fresh reagents. The treated peptide resin was then washed with DCM×3 and DMF×3.

Step 5: Lactam Formation

The lactam ring was formed on the peptide resin using TBTU (2 eq.) and ethyldiisopropylamine (DIEA) (4 eq.) in 20 mL DMF for 1 hour. A second coupling may be needed if a positive Kaiser Ninhydrin test is observed.

Step 6: Peptide Cleavage

The peptide resin (0.6 mmol) was mixed with 20 mL of 5% sodium diethyldithio-carbamate trihydrate ($NaCS_2NEt_2$, Aldrich, #228680) in DMF for 20 min and then washed with DMF×3, DCM×3 and diethyl ether×2.

The resin (0.6 mmol) was then stirred in a 25 mL of TFA/TIS/H2O (90:5.0:5.0 v/v/v) for 2.5 hours. The resin was filtered. The filtrate was concentrated to about 10 mL in volume and about 140 mL of cold diethyl ether (pre-cooled to about 0° C.) was added.

The mixture was vortexed, and then placed in the refrigerator (about −4° C.) for 1 h, centrifuged for 5 min at 2800 rpm, and the ether layer was decanted.

The peptide was washed with 90 mL of cold diethyl ether (pre-cooled to about 0° C.), vortexed, centrifuged for 5 min at 2800 rpm, and ether layer decanted.

The resulting solid was dissolved in 50% $AcOH/H_2O$ and stored at room temperature overnight.

The crude peptide solution was concentrated to afford solid crude peptide for HPLC purification.

After HPLC purification, the peptide TFA salt was converted to peptide acetate salt using ion exchange (×100 eq.). The anion exchange resin used was Dowex SBR LC NG, OH-form (Supelco, Cat#14036-U).

Example 46

Ac-Arg-cyclo(Glu-Gln-D-Phe(4-CN)-Arg-Trp-Orn)-$NH_2$ (SEQ ID NO:51)

The procedure described above was followed in the preparation of the title peptide.

The amino acids added in step 2 were, in the order of being coupled, Fmoc-Trp(Boc)-OH, Fmoc-Arg(Pbf)-OH, Fmoc-D-Phe(4-CN)—OH, Fmoc-Gln(Trt)-OH, Fmoc-Glu(OAll)-OH, and Fmoc-Arg(Pbf)-OH.

The resulting peptide was purified by HPLC (column: Atlantis dC18 OBD™ 19×100 mm (5μ, Waters part #186001367) using 10% $MeOH/H_2O$ containing 0.1% TFA (solvent A) and 90% $MeOH/H_2O$ containing 0.1% TFA (solvent B). A gradient of 0%-5% of solvent B for 5 min and 5%-35% of solvent B for 30 min was used.

The peptide yield was 10%.

Example 67

Ac-Arg-cyclo(Glu-Pro-D-Phe(4-F)-Arg-Trp-Orn)-$NH_2$ (SEQ ID NO:72)

The procedure described above was followed in the preparation of the title peptide except for that 15 mL of 5% sodium diethyldithio-carbamate trihydrate in DMF, 16 mL of TFA/TIS/$H_2O$ and 90 mL+60 mL of diethyl ether were used in step 6. Moreover, the filtrate was concentrated to 5 mL.

The amino acids added in step 2 were, in the order of being coupled, Fmoc-Trp(Boc)-OH, Fmoc-Arg(Pbf)-OH, Fmoc-D-Phe(4-F)—OH, Fmoc-Pro-OH, Fmoc-Glu(OAll)-OH, and Fmoc-Arg(Pbf)-OH.

The resulting peptide was purified by HPLC (column: Atlantis dC18 OBD™ 19×100 mm (5μ, Waters part #186001367) using 10% $MeOH/H_2O$ containing 0.1% TFA (solvent A) and 90% $MeOH/H_2O$ containing 0.1% TFA (solvent B). A gradient of 5%-10% of solvent B for 5 min and 10%-40% of solvent B for 30 min was used.

The peptide yield was 16%.

| No. | Structure | Amino Acid Sequence | MC4-R Ki (nM) | MC1-R Ki (nM) |
|---|---|---|---|---|
| 1 | 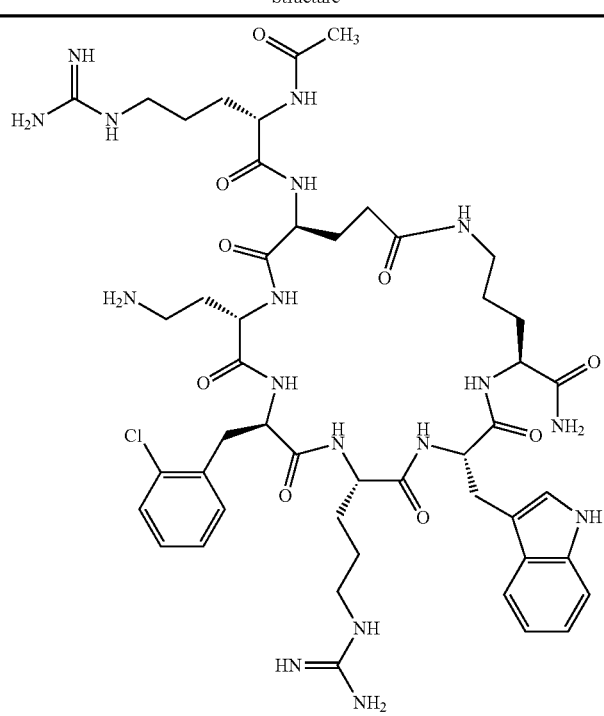 | Ac-Arg-cyclo(Glu-Dab-D-Phe(2-Cl)-Arg-Trp-Orn)-$NH_2$ (SEQ ID NO: 6) | 3 | 1 |

-continued

| No. | Structure | Amino Acid Sequence | MC4-R Ki (nM) | MC1-R Ki (nM) |
|---|---|---|---|---|
| 2 | 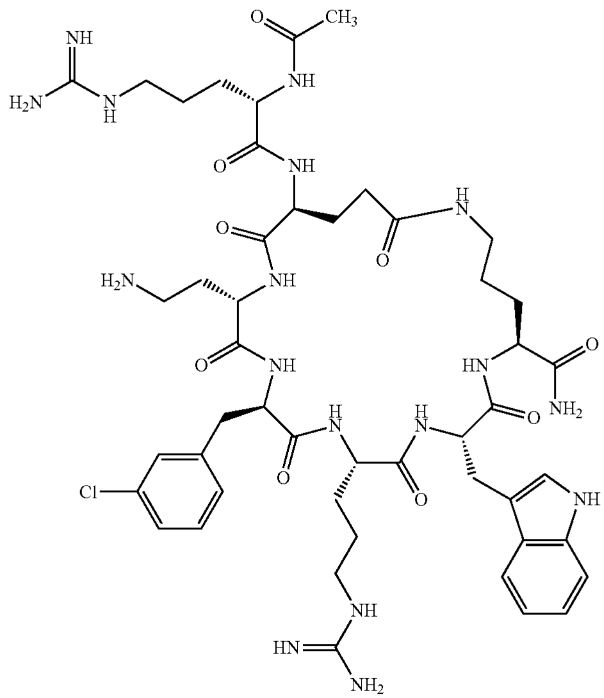 | Ac-Arg-cyclo(Glu-Dab-D-Phe(3-Cl)-Arg-Trp-Orn)-NH$_2$ (SEQ ID NO: 7) | 0.75 | 1 |
| 3 | 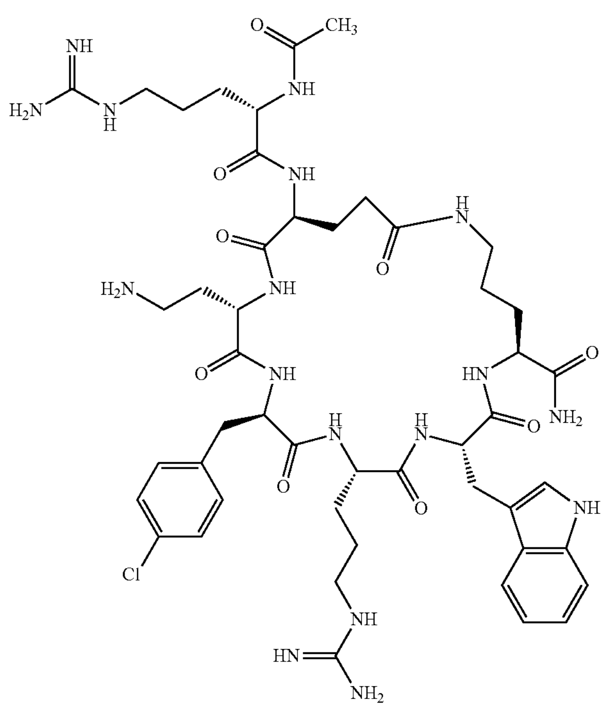 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(Cl)cc2)NC(=O)[C@H](CCN)NC1=O] | Ac-Arg-cyclo(Glu-Dab-D-Phe(4-Cl)-Arg-Trp-Orn)-NH$_2$ (SEQ ID NO: 8) | 0.08 | 0.3 |

| No. | Structure | Amino Acid Sequence | MC4-R Ki (nM) | MC1-R Ki (nM) |
|---|---|---|---|---|
| 4 | 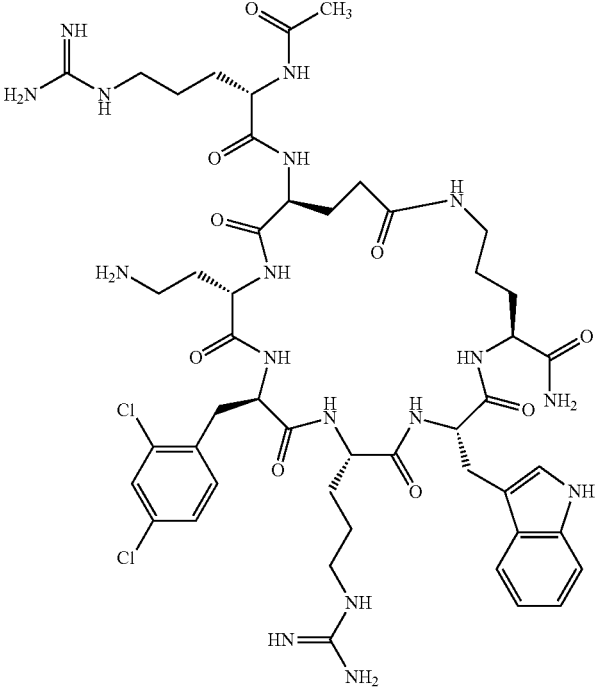 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(Cl)cc2Cl)NC(=O)[C@H](CCN)NC1=O] | Ac-Arg-cyclo(Glu-Dab-D-Phe(2,4-diCl)-Arg-Trp-Orn)-NH$_2$ (SEQ ID NO: 9) | 0.055 | 0.5 |
| 5 | 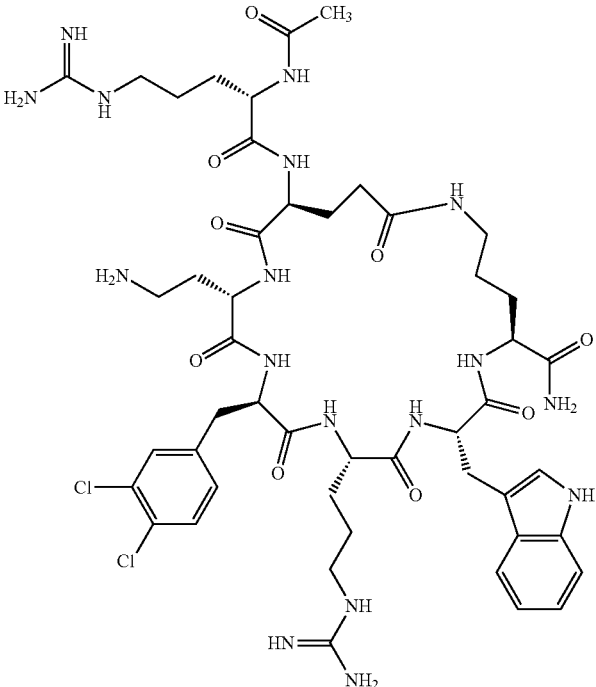 | Ac-Arg-cyclo(Glu-Dab-D-Phe(3,4-diCl)-Arg-Trp-Orn)-NH$_2$ (SEQ ID NO: 10) | 0.055 | 0.2 |

| No. | Structure | Amino Acid Sequence | MC4-R Ki (nM) | MC1-R Ki (nM) |
|---|---|---|---|---|
| 6 | 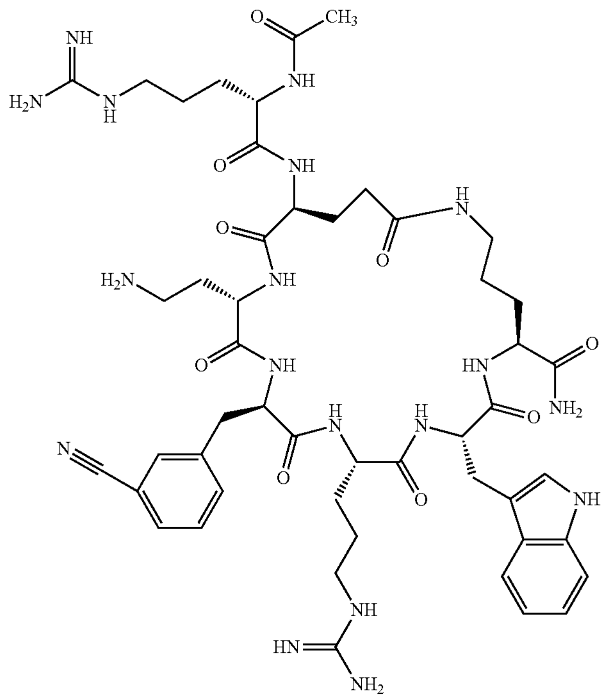 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2cccc(C#N)c2)NC(=O)[C@H](CCN)NC1=O] | Ac-Arg-cyclo(Glu-Dab-D-Phe(3-CN)-Arg-Trp-Orn)-NH$_2$ (SEQ ID NO: 11) | 33 | 43 |
| 7 | 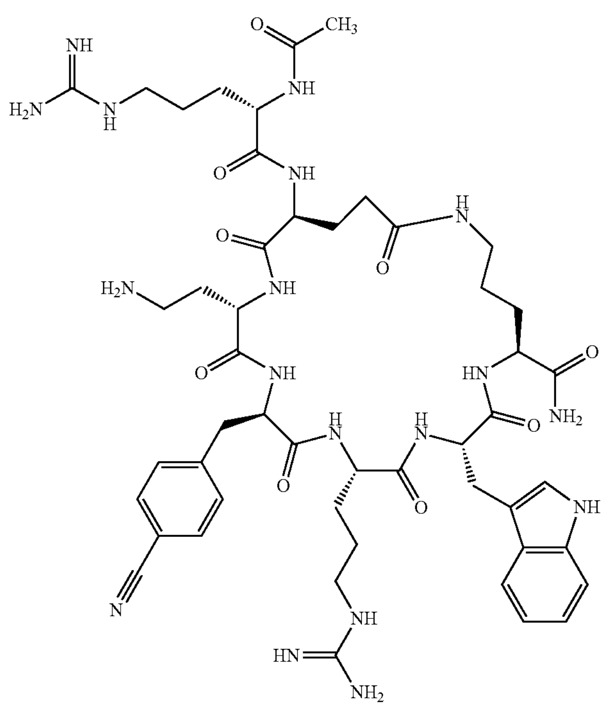 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(C#N)cc2)NC(=O)[C@H](CCN)NC1=O] | Ac-Arg-cyclo(Glu-Dab-D-Phe(4-CN)-Arg-Trp-Orn)-NH$_2$ (SEQ ID NO: 12) | 0.833 | 5 |

| No. | Structure | Amino Acid Sequence | MC4-R Ki (nM) | MC1-R Ki (nM) |
|---|---|---|---|---|
| 8 | 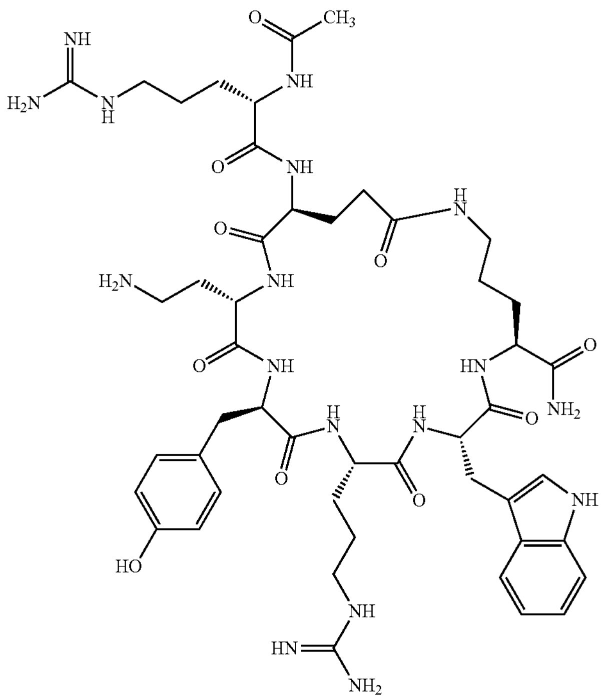 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(O)cc2)NC(=O)[C@H](CCN)NC1=O] | Ac-Arg-cyclo(Glu-Dab-D-Tyr-Arg-Trp-Orn)-NH$_2$ (SEQ ID NO: 13) | 75 | 15 |
| 9 | 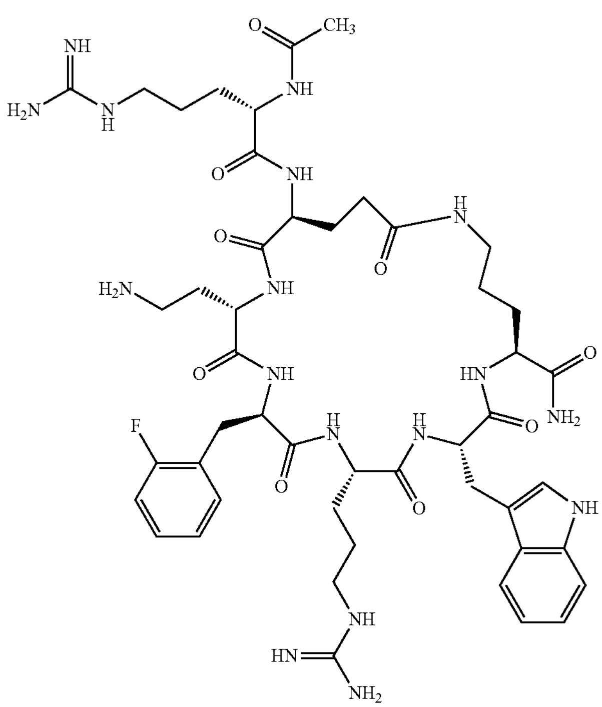 | Ac-Arg-cyclo(Glu-Dab-D-Phe(2-F)-Arg-Trp-Orn)-NH$_2$ (SEQ ID NO: 14) | 0.7 | 0.8 |

| No. | Structure | Amino Acid Sequence | MC4-R Ki (nM) | MC1-R Ki (nM) |
|---|---|---|---|---|
| 10 | 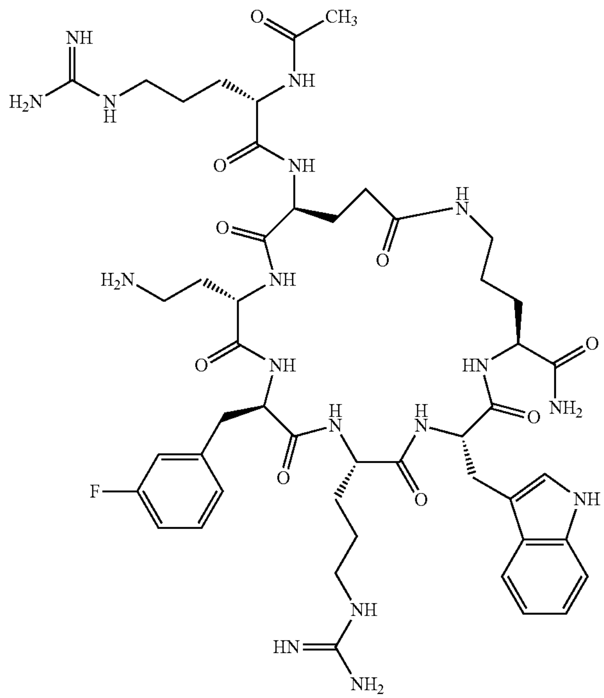 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2cccc(F)c2)NC(=O)[C@H](CCN)NC1=O] | Ac-Arg-cyclo(Glu-Dab-D-Phe(3-F)-Arg-Trp-Orn)-NH$_2$ (SEQ ID NO: 15) | 2 | 2 |
| 11 | 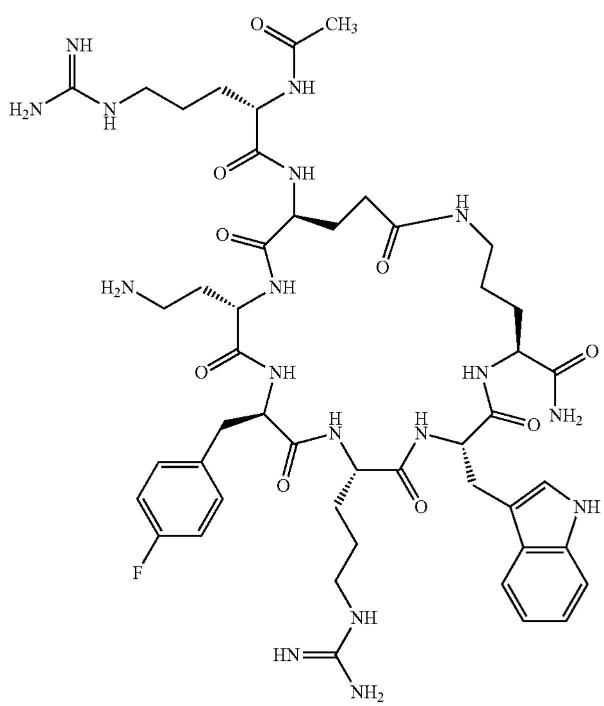 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(F)cc2)NC(=O)[C@H](CCN)NC1=O] | Ac-Arg-cyclo(Glu-Dab-D-Phe(4-F)-Arg-Trp-Orn)-NH$_2$ (SEQ ID NO: 16) | 0.25 | 0.5 |

| No. | Structure | Amino Acid Sequence | MC4-R Ki (nM) | MC1-R Ki (nM) |
|---|---|---|---|---|
| 12 | 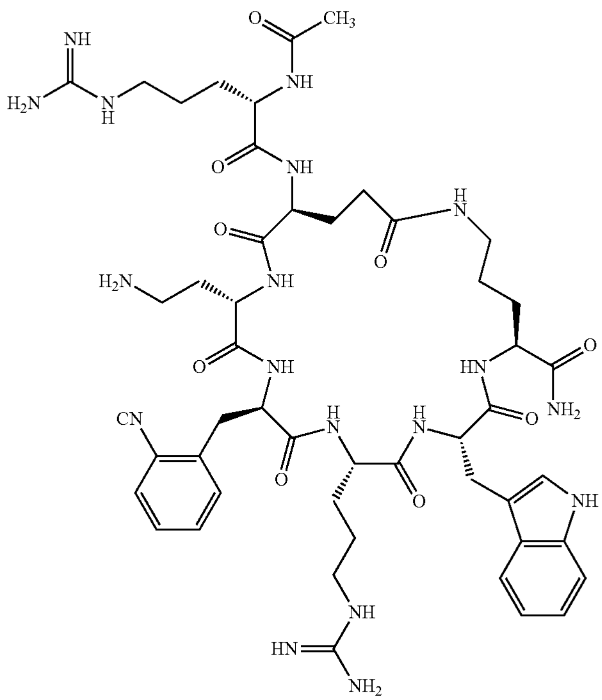 | Ac-Arg-cyclo(Glu-Dab-D-Phe(2-CN)-Arg-Trp-Orn)-NH$_2$ (SEQ ID NO: 17) | 45 | 35 |
| 13 | 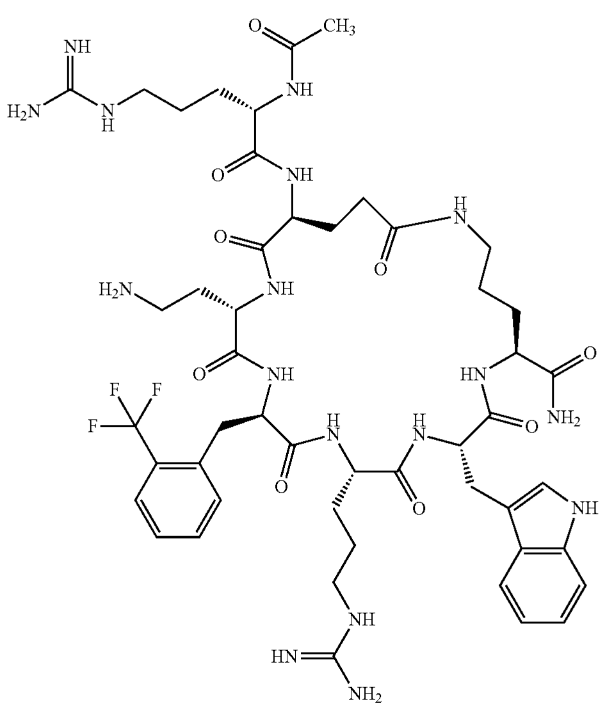 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2C(F)(F)F)NC(=O)[C@H](CCN)NC1=O] | Ac-Arg-cyclo(Glu-Dab-D-Phe(2-CF$_3$)-Arg-Trp-Orn)-NH$_2$ (SEQ ID NO: 18) | 0.6 | 3 |

| No. | Structure | Amino Acid Sequence | MC4-R Ki (nM) | MC1-R Ki (nM) |
|---|---|---|---|---|
| 14 | 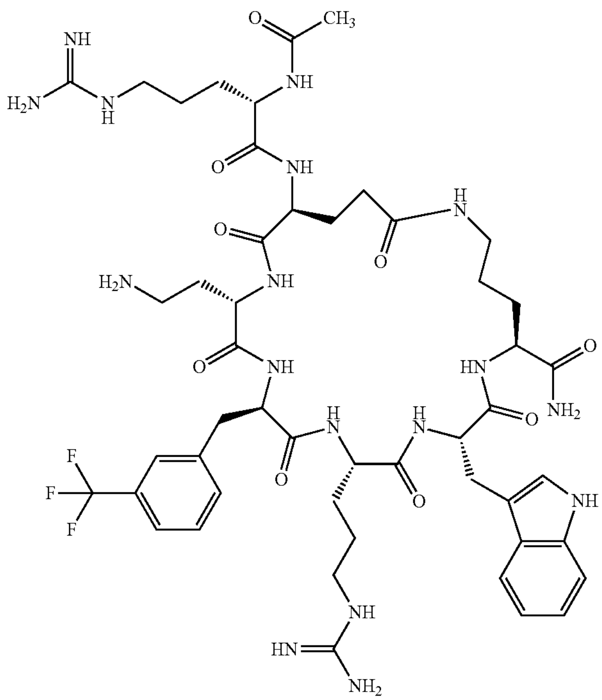 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2cccc(C(F)(F)F)c2)NC(=O)[C@H](CCN)NC1=O] | Ac-Arg-cyclo(Glu-Dab-D-Phe(3-CF₃)-Arg-Trp-Orn)-NH₂ (SEQ ID NO: 19) | 0.95 | 9 |
| 15 | 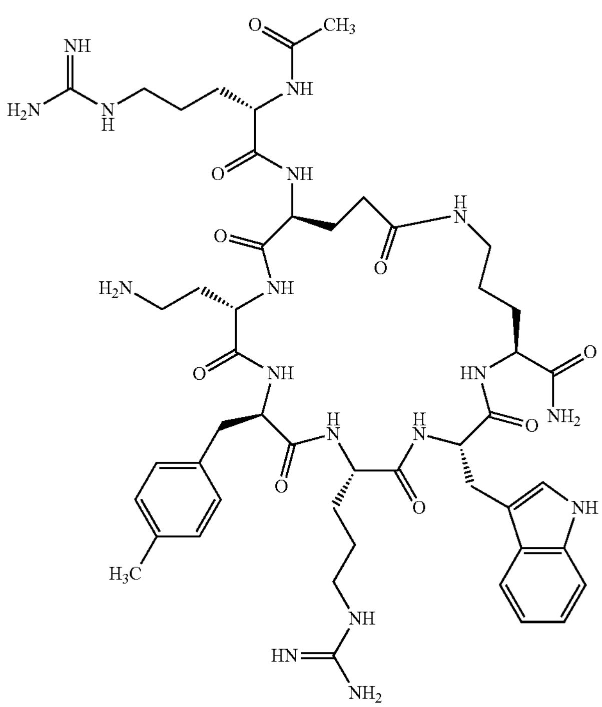 | Ac-Arg-cyclo(Glu-Dab-D-Phe(4-Me)-Arg-Trp-Orn)-NH₂ (SEQ ID NO: 20) | 0.145 | 0.75 |

| No. | Structure | Amino Acid Sequence | MC4-R Ki (nM) | MC1-R Ki (nM) |
|---|---|---|---|---|
| 16 | 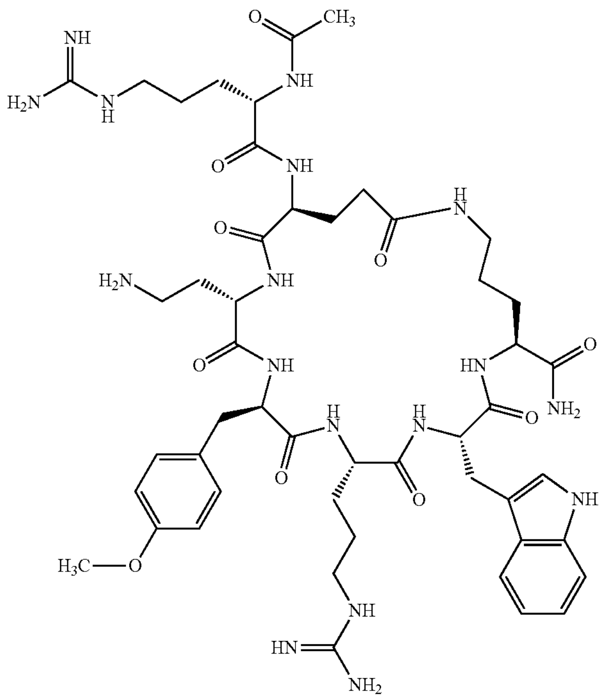 [SMILES: COc1ccc(C[C@H]2NC(=O)[C@H](CCN)NC(=O)[C@@H](NC(=O)[C@H](CCCNC(=N)N)NC(C)=O)CCC(=O)NCCC[C@@H](C(N)=O)NC(=O)[C@H](Cc3c[nH]c4ccccc34)NC(=O)[C@H](CCCNC(=N)N)NC2=O)cc1] | Ac-Arg-cyclo(Glu-Dab-D-Phe(4-OMe)-Arg-Trp-Orn)-NH₂ (SEQ ID NO: 21) | 0.25 | 0.15 |
| 17 | 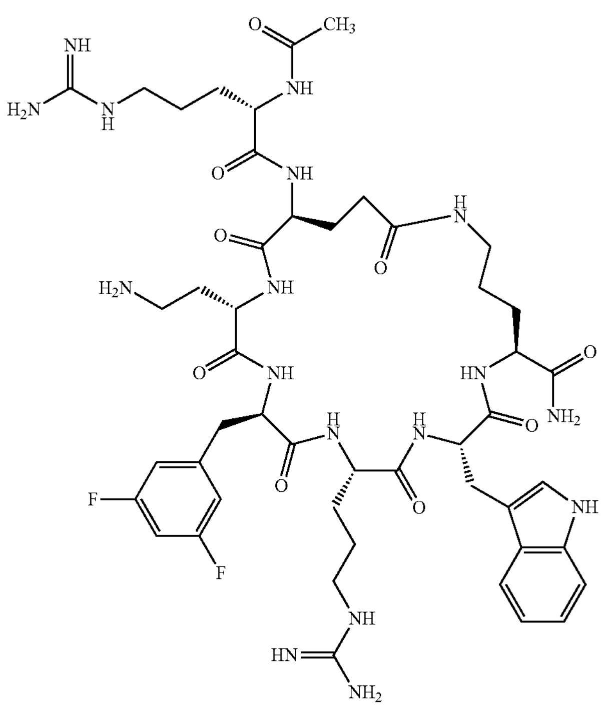 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2cc(F)cc(F)c2)NC(=O)[C@H](CCN)NC1=O] | Ac-Arg-cyclo(Glu-Dab-D-Phe(3,5-diF)-Arg-Trp-Orn)-NH₂ (SEQ ID NO: 22) | 2 | — |

| No. | Structure | Amino Acid Sequence | MC4-R Ki (nM) | MC1-R Ki (nM) |
|---|---|---|---|---|
| 18 | 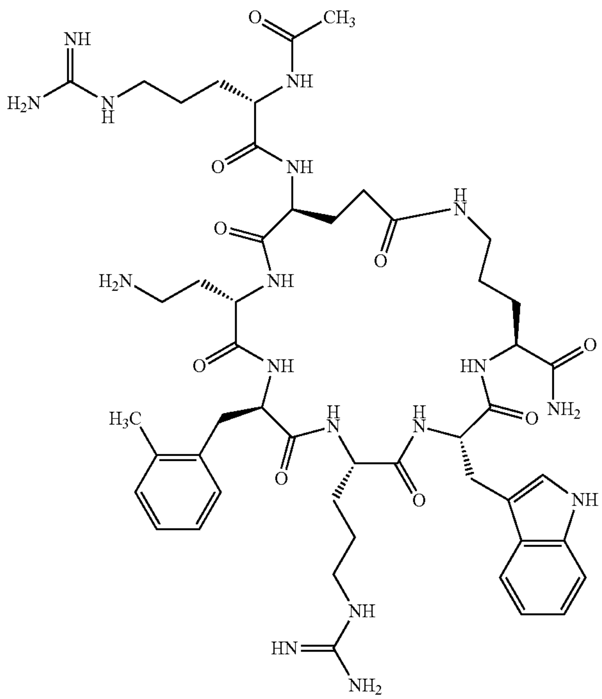 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2C)NC(=O)[C@H](CCN)NC1=O] | Ac-Arg-cyclo(Glu-Dab-D-Phe(2-Me)-Arg-Trp-Orn)-NH$_2$ (SEQ ID NO: 23) | 0.5 | — |
| 19 | 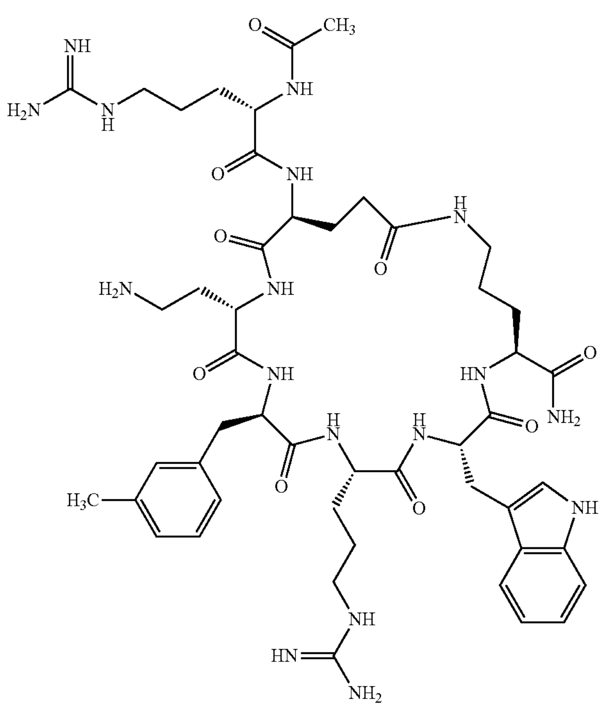 | Ac-Arg-cyclo(Glu-Dab-D-Phe(3-Me)-Arg-Trp-Orn)-NH$_2$ (SEQ ID NO: 24) | 0.4 | — |

| No. | Structure | Amino Acid Sequence | MC4-R Ki (nM) | MC1-R Ki (nM) |
|---|---|---|---|---|
| 20 | 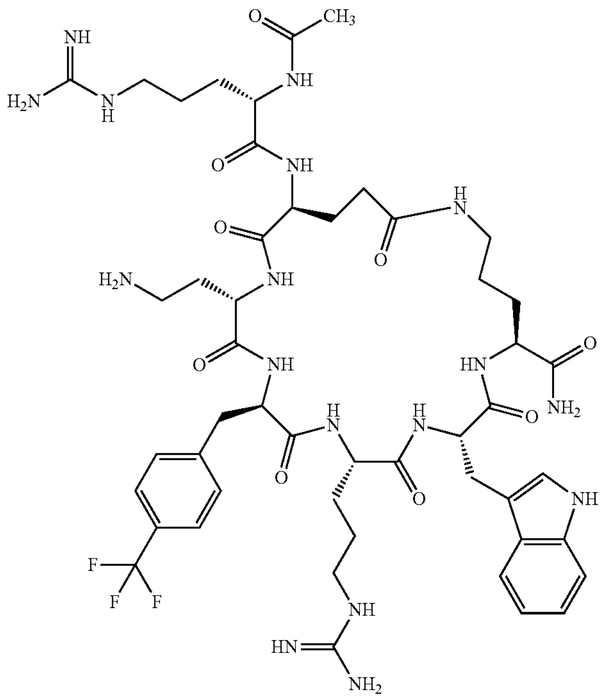 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(C(F)(F)F)cc2)NC(=O)[C@H](CCN)NC1=O] | Ac-Arg-cyclo(Glu-Dab-D-Phe(4-CF$_3$)-Arg-Trp-Orn)-NH$_2$ (SEQ ID NO: 25) | 0.06 | — |
| 21 | 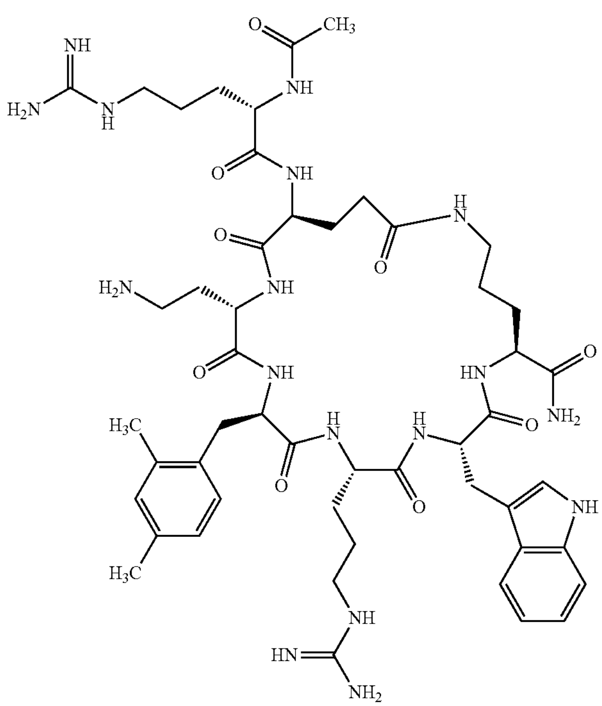 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(C)cc2C)NC(=O)[C@H](CCN)NC1=O] | Ac-Arg-cyclo(Glu-Dab-D-Phe(2,4-diMe)-Arg-Trp-Orn)-NH$_2$ (SEQ ID NO: 26) | 0.085 | — |

-continued

| No. | Structure | Amino Acid Sequence | MC4-R Ki (nM) | MC1-R Ki (nM) |
|---|---|---|---|---|
| 22 | 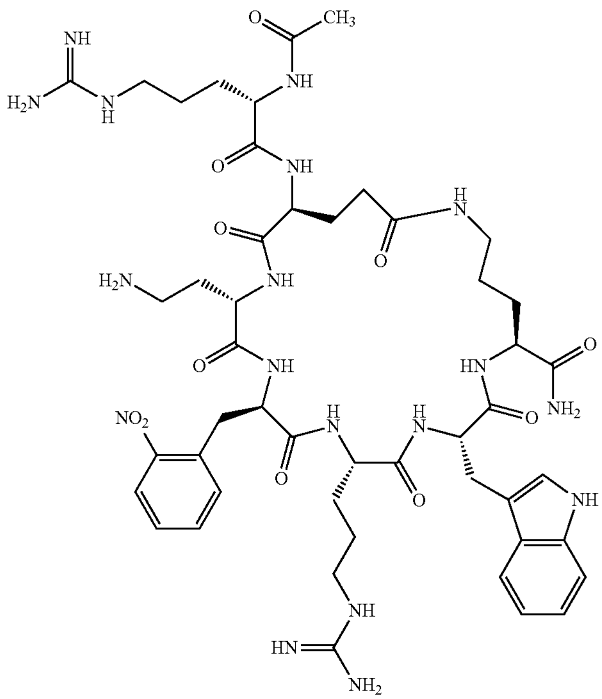 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2[N+](=O)[O-])NC(=O)[C@H](CCN)NC1=O] | Ac-Arg-cyclo(Glu-Dab-D-Phe(2-NO$_2$)-Arg-Trp-Orn)-NH$_2$ (SEQ ID NO: 27) | 11 | — |
| 23 | 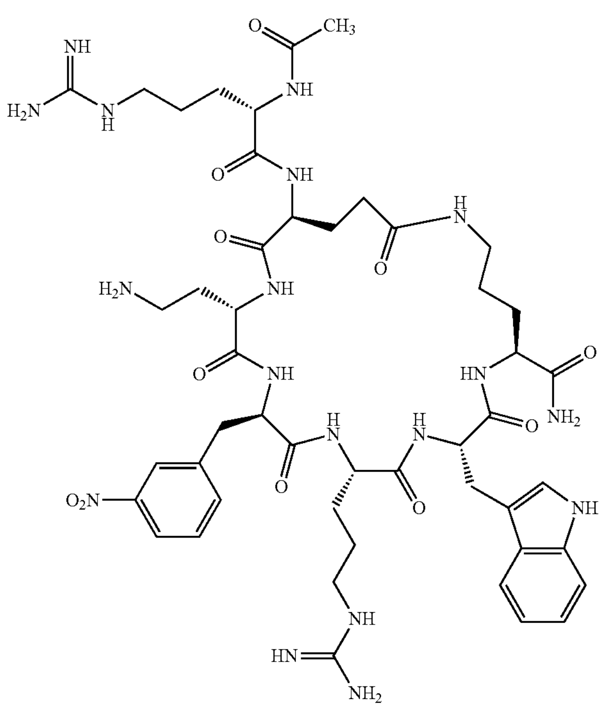 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2cccc([N+](=O)[O-])c2)NC(=O)[C@H](CCN)NC1=O] | Ac-Arg-cyclo(Glu-Dab-D-Phe(3-NO$_2$)-Arg-Trp-Orn)-NH$_2$ (SEQ ID NO: 28) | 0.7 | — |

| No. | Structure | Amino Acid Sequence | MC4-R Ki (nM) | MC1-R Ki (nM) |
|---|---|---|---|---|
| 24 | 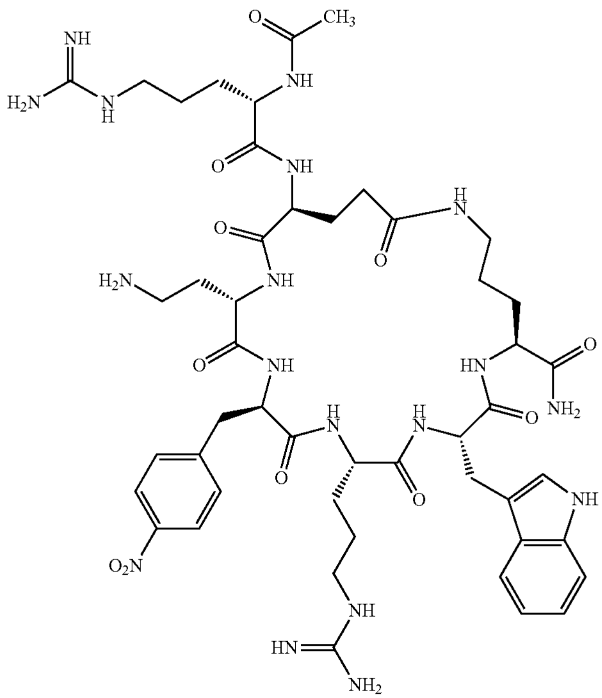 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc([N+](=O)[O-])cc2)NC(=O)[C@H](CCN)NC1=O] | Ac-Arg-cyclo(Glu-Dab-D-Phe(4-NO$_2$)-Arg-Trp-Orn)-NH$_2$ (SEQ ID NO: 29) | 0.45 | — |
| 25 | 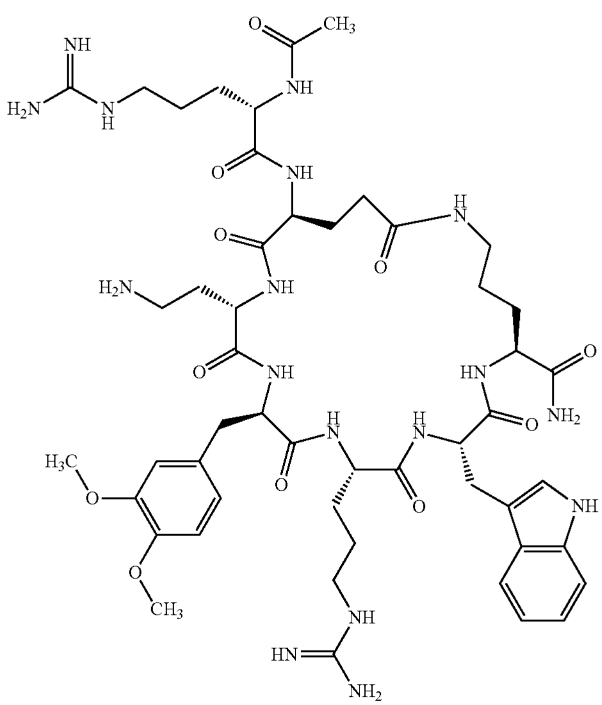 [SMILES: COc1ccc(C[C@H]2NC(=O)[C@H](CCN)NC(=O)[C@@H](NC(=O)[C@H](CCCNC(=N)N)NC(C)=O)CCC(=O)NCCC[C@@H](C(N)=O)NC(=O)[C@H](Cc3c[nH]c4ccccc34)NC(=O)[C@H](CCCNC(=N)N)NC2=O)cc1OC] | Ac-Arg-cyclo(Glu-Dab-D-Phe(3,4-diOMe)-Arg-Trp-Orn)-NH$_2$ (SEQ ID NO: 30) | 35 | — |

| No. | Structure | Amino Acid Sequence | MC4-R Ki (nM) | MC1-R Ki (nM) |
|---|---|---|---|---|
| 26 | 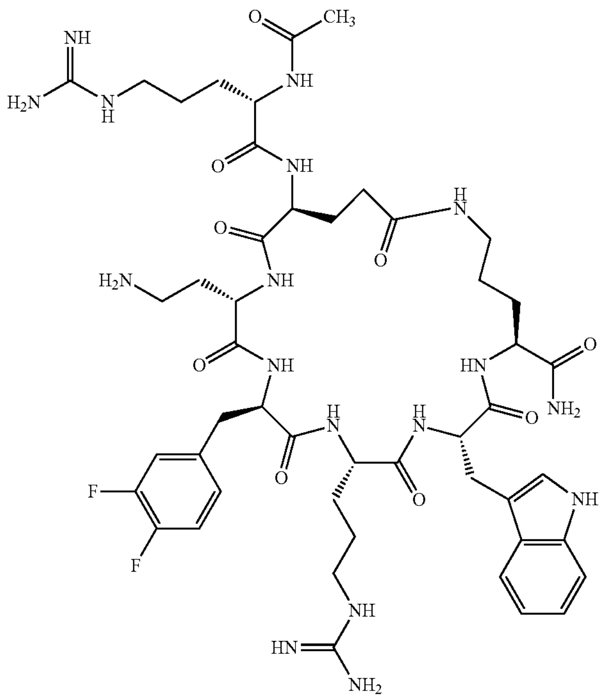 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(F)c(F)c2)NC(=O)[C@H](CCN)NC1=O] | Ac-Arg-cyclo(Glu-Dab-D-Phe(3,4-diF)-Arg-Trp-Orn)-NH$_2$ (SEQ ID NO: 31) | 0.3 | — |
| 27 | 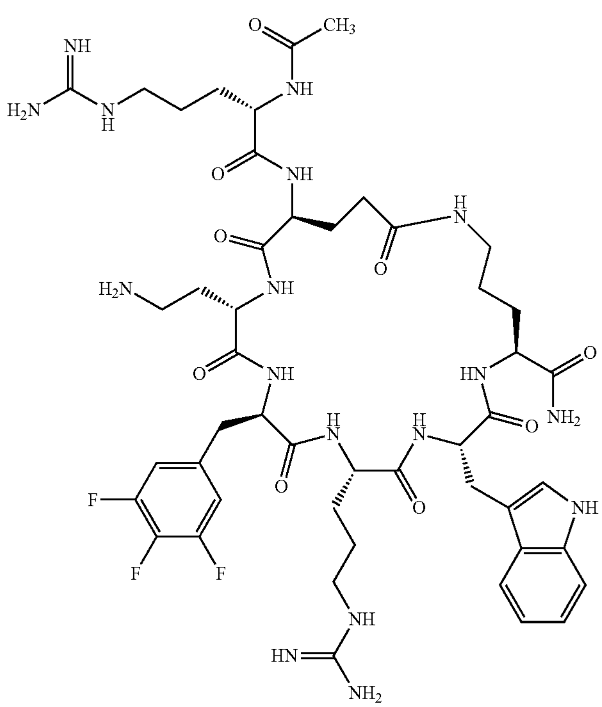 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2cc(F)c(F)c(F)c2)NC(=O)[C@H](CCN)NC1=O] | Ac-Arg-cyclo(Glu-Dab-D-Phe(3,4,5-triF)-Arg-Trp-Orn)-NH$_2$ (SEQ ID NO: 32) | 0.667 | — |

| No. | Structure | Amino Acid Sequence | MC4-R Ki (nM) | MC1-R Ki (nM) |
|---|---|---|---|---|
| 28 | 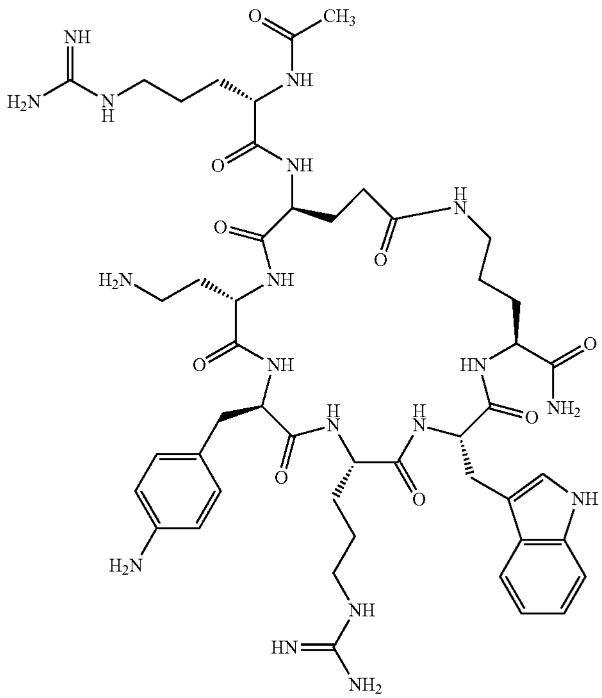 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(N)cc2)NC(=O)[C@H](CCN)NC1=O] | Ac-Arg-cyclo(Glu-Dab-D-Phe(4-NH$_2$)-Arg-Trp-Orn)-NH$_2$ (SEQ ID NO: 33) | 48 | — |
| 29 | 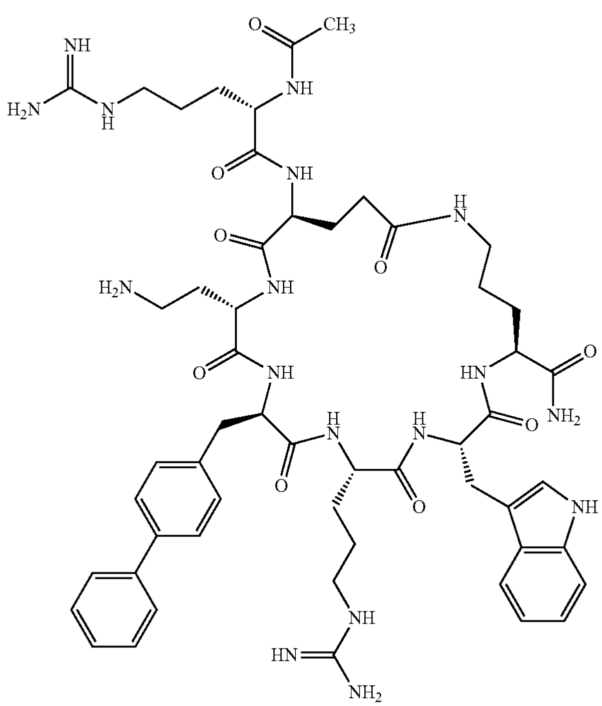 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(-c3ccccc3)cc2)NC(=O)[C@H](CCN)NC1=O] | Ac-Arg-cyclo(Glu-Dab-D-Phe(4-Ph)-Arg-Trp-Orn)-NH$_2$ (SEQ ID NO: 34) | 0.5 | — |

| No. | Structure | Amino Acid Sequence | MC4-R Ki (nM) | MC1-R Ki (nM) |
|---|---|---|---|---|
| 30 | 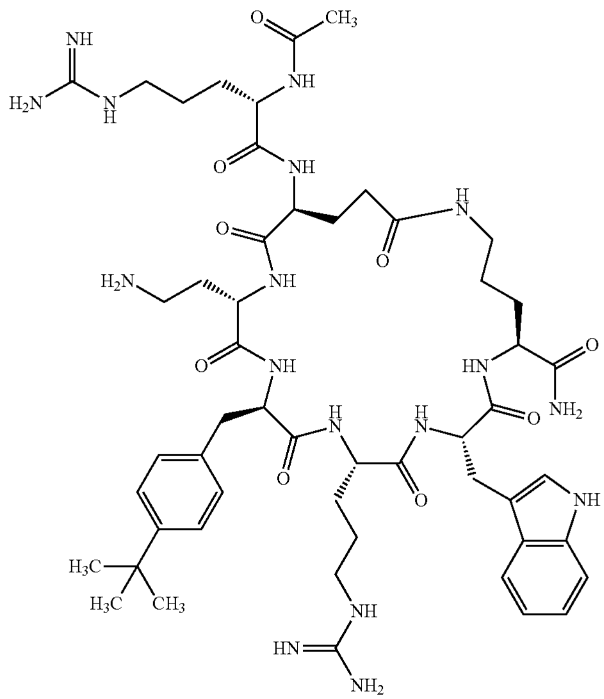 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(C(C)(C)C)cc2)NC(=O)[C@H](CCN)NC1=O] | Ac-Arg-cyclo(Glu-Dab-D-Phe(4-tBu)-Arg-Trp-Orn)-NH$_2$ (SEQ ID NO: 35) | 4 | — |
| 31 | 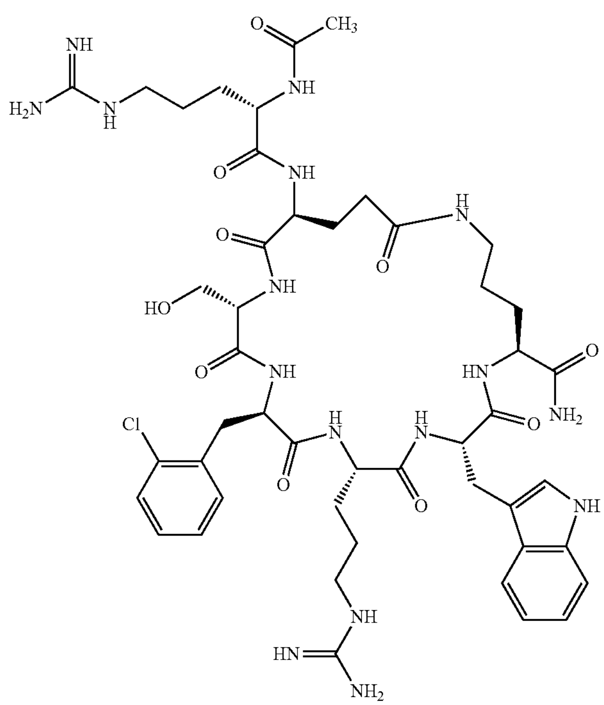 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2Cl)NC(=O)[C@H](CO)NC1=O] | Ac-Arg-cyclo(Glu-Ser-D-Phe(2-Cl)-Arg-Trp-Orn)-NH$_2$ (SEQ ID NO: 36) | 8 | 300 |

-continued

| No. | Structure | Amino Acid Sequence | MC4-R Ki (nM) | MC1-R Ki (nM) |
|---|---|---|---|---|
| 32 | 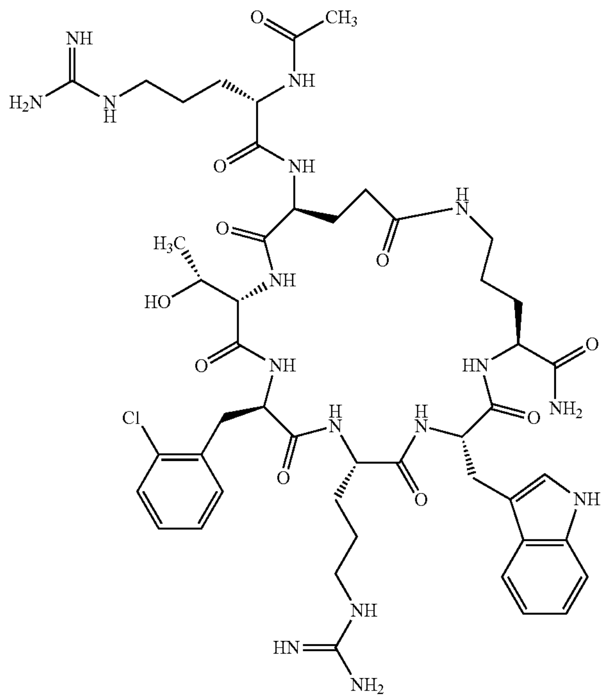 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2Cl)NC(=O)[C@H]([C@@H](C)O)NC1=O] | Ac-Arg-cyclo(Glu-Thr-D-Phe(2-Cl)-Arg-Trp-Orn)-NH₂ (SEQ ID NO: 37) | 11 | 540 |
| 33 | 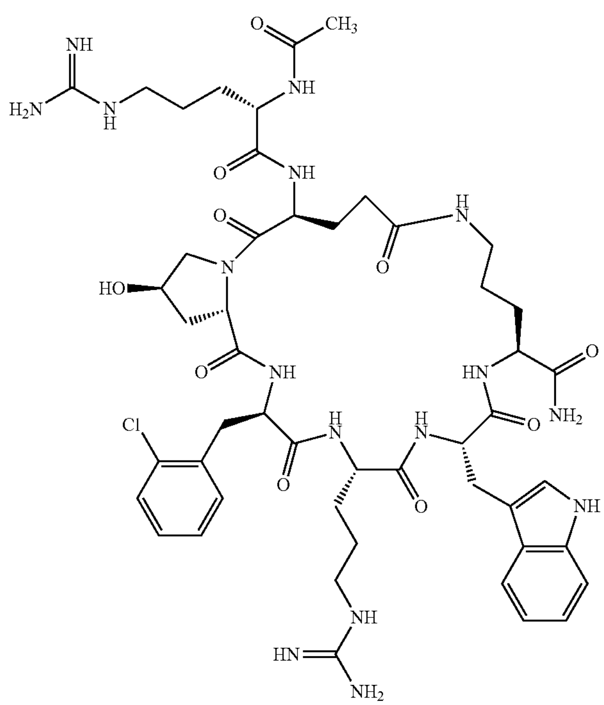 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2Cl)NC(=O)[C@@H]2C[C@@H](O)CN2C1=O] | Ac-Arg-cyclo(Glu-Hyp-D-Phe(2-Cl)-Arg-Trp-Orn)-NH₂ (SEQ ID NO: 38) | 1 | 143 |

| No. | Structure | Amino Acid Sequence | MC4-R Ki (nM) | MC1-R Ki (nM) |
|---|---|---|---|---|
| 34 | 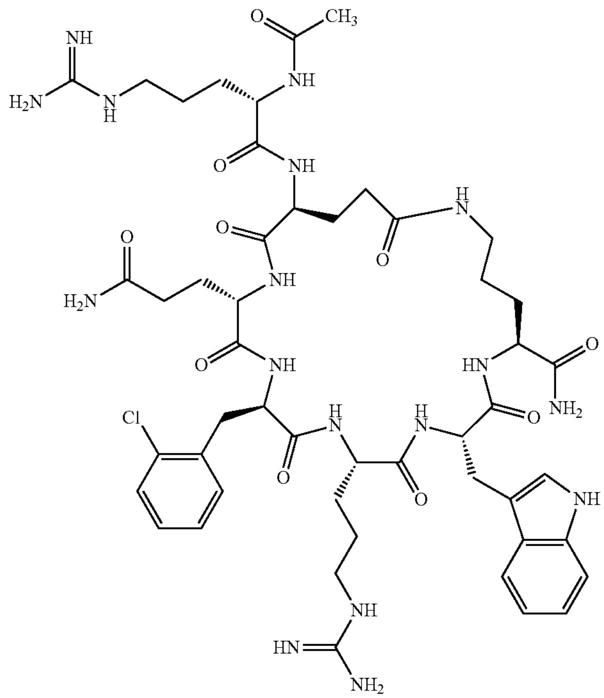 | Ac-Arg-cyclo(Glu-Gln-D-Phe(2-Cl)-Arg-Trp-Orn)-NH$_2$ (SEQ ID NO: 39) | 7 | 128 |
| 35 | 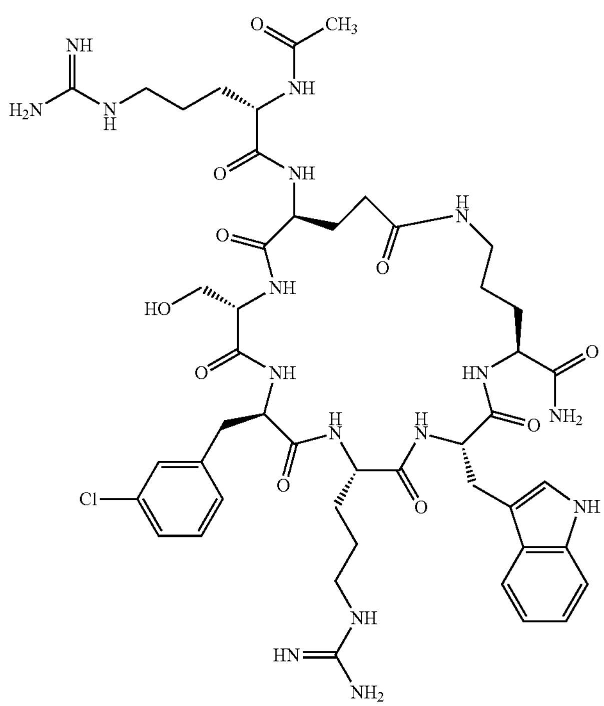 | Ac-Arg-cyclo(Glu-Ser-D-Phe(3-Cl)-Arg-Trp-Orn)-NH$_2$ (SEQ ID NO: 40) | 10 | 810 |

| No. | Structure | Amino Acid Sequence | MC4-R Ki (nM) | MC1-R Ki (nM) |
|---|---|---|---|---|
| 36 | 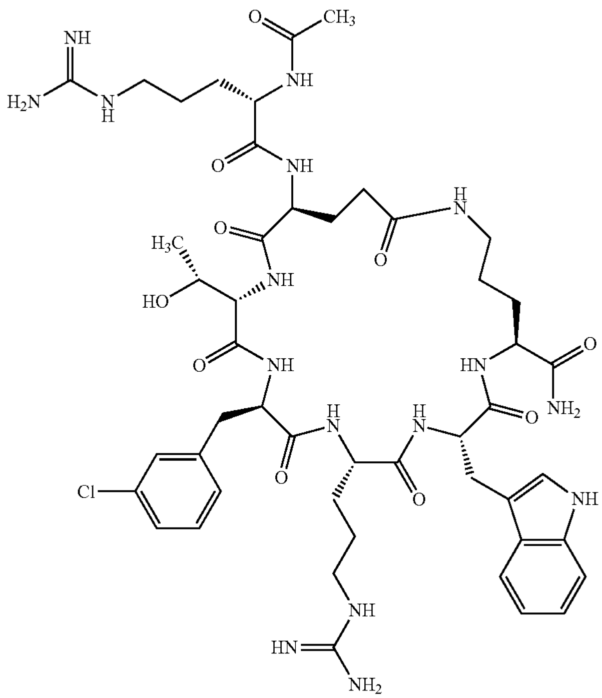 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2cccc(Cl)c2)NC(=O)[C@H]([C@@H](C)O)NC1=O] | Ac-Arg-cyclo(Glu-Thr-D-Phe(3-Cl)-Arg-Trp-Orn)-NH$_2$ (SEQ ID NO: 41) | 6 | 380 |
| 37 | 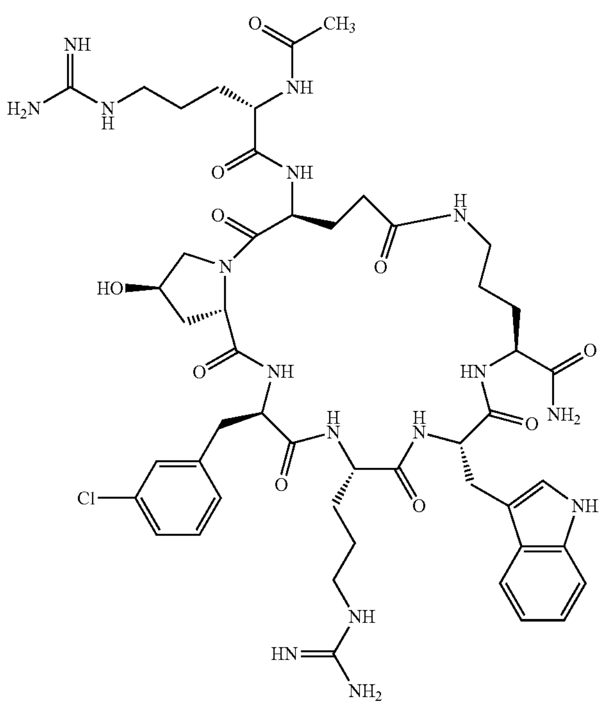 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2cccc(Cl)c2)NC(=O)[C@@H]2C[C@@H](O)CN2C1=O] | Ac-Arg-cyclo(Glu-Hyp-D-Phe(3-Cl)-Arg-Trp-Orn)-NH$_2$ (SEQ ID NO: 42) | 2 | 430 |

| No. | Structure | Amino Acid Sequence | MC4-R Ki (nM) | MC1-R Ki (nM) |
|---|---|---|---|---|
| 38 | 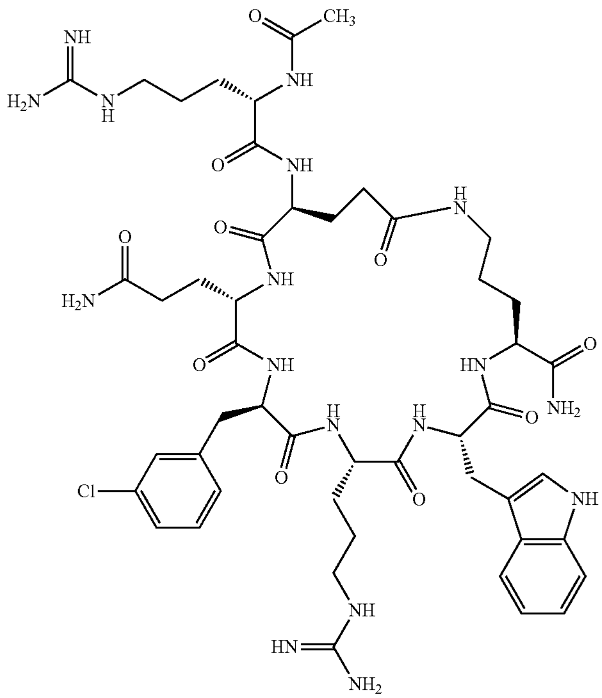 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2cccc(Cl)c2)NC(=O)[C@H](CCC(N)=O)NC1=O] | Ac-Arg-cyclo(Glu-Gln-D-Phe(3-Cl)-Arg-Trp-Orn)-NH$_2$ (SEQ ID NO: 43) | 3 | 290 |
| 39 | 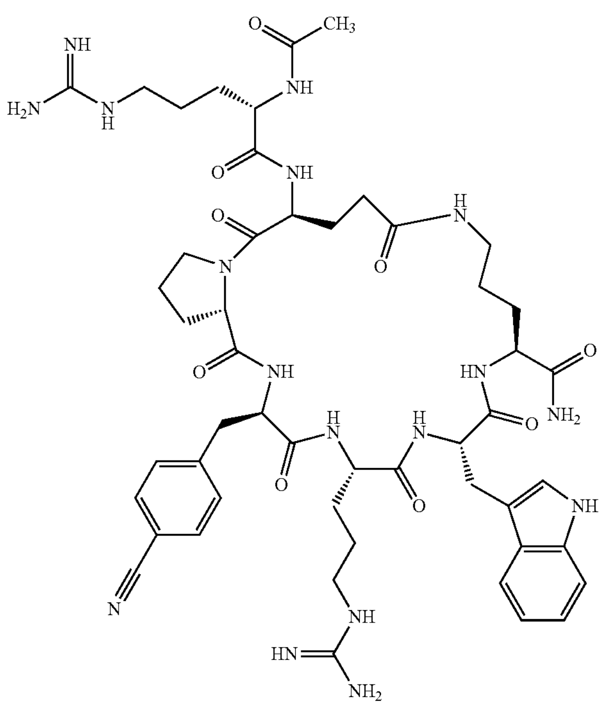 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(C#N)cc2)NC(=O)[C@@H]2CCCN2C1=O] | Ac-Arg-cyclo(Glu-Pro-D-Phe(4-CN)-Arg-Trp-Orn)-NH$_2$ (SEQ ID NO: 44) | 4 | 1550 |

| No. | Structure | Amino Acid Sequence | MC4-R Ki (nM) | MC1-R Ki (nM) |
|---|---|---|---|---|
| 40 | 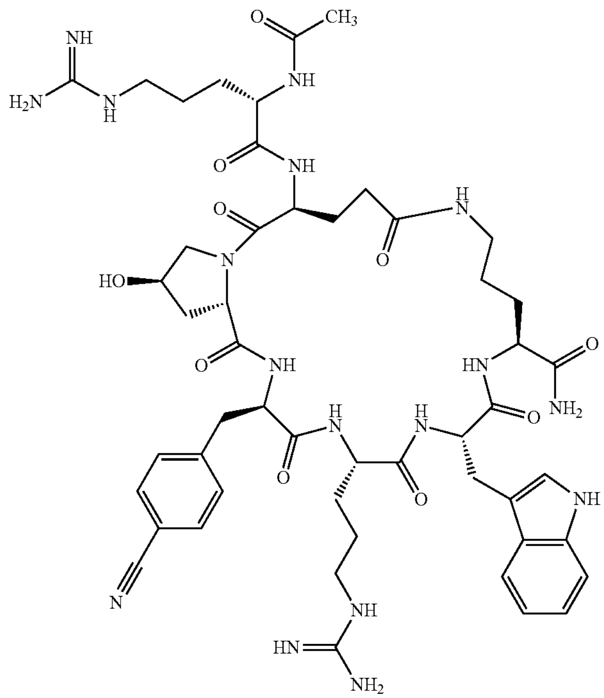 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(C#N)cc2)NC(=O)[C@@H]2C[C@@H](O)CN2C1=O] | Ac-Arg-cyclo(Glu-Hyp-D-Phe(4-CN)-Arg-Trp-Orn)-NH$_2$ (SEQ ID NO: 45) | 2 | 880 |
| 41 | 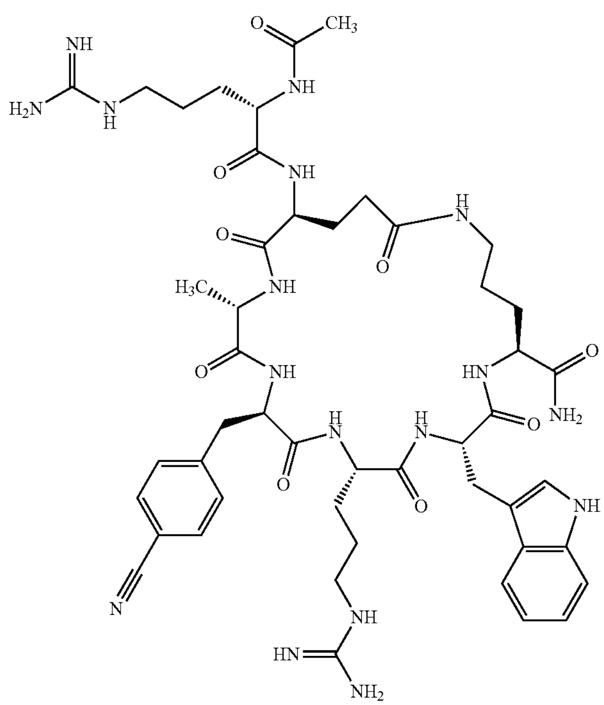 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(C#N)cc2)NC(=O)[C@H](C)NC1=O] | Ac-Arg-cyclo(Glu-Ala-D-Phe(4-CN)-Arg-Trp-Orn)-NH$_2$ (SEQ ID NO: 46) | 3 | 4300 |

| No. | Structure | Amino Acid Sequence | MC4-R Ki (nM) | MC1-R Ki (nM) |
|---|---|---|---|---|
| 42 | 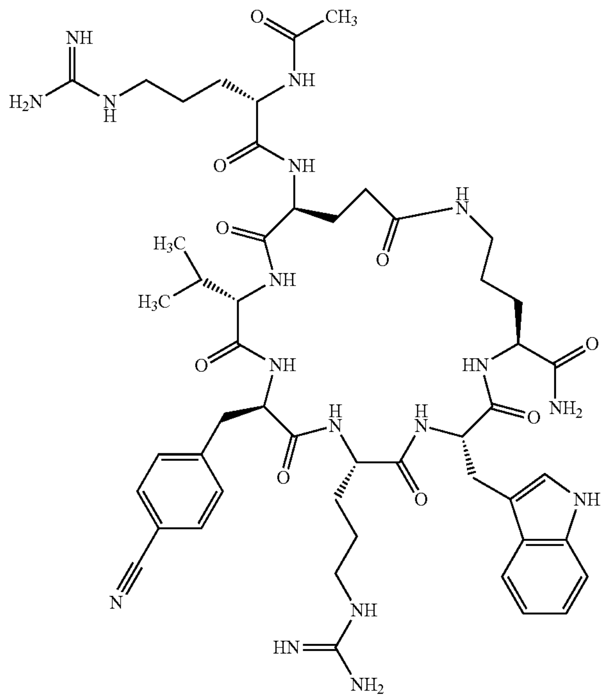 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(C#N)cc2)NC(=O)[C@H](C(C)C)NC1=O] | Ac-Arg-cyclo(Glu-Val-D-Phe(4-CN)-Arg-Trp-Orn)-NH$_2$ (SEQ ID NO: 47) | 6 | 420 |
| 43 | 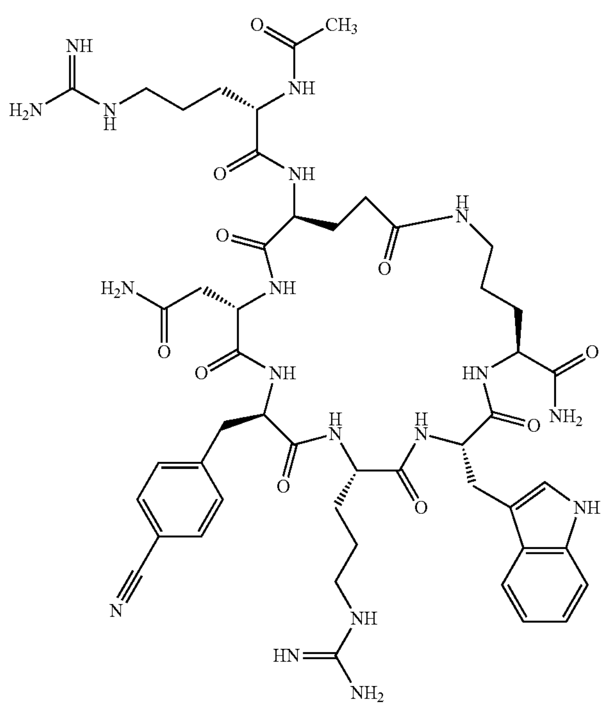 | Ac-Arg-cyclo(Glu-Asn-D-Phe(4-CN)-Arg-Trp-Orn)-NH$_2$ (SEQ ID NO: 48) | 5 | 870 |

| No. | Structure | Amino Acid Sequence | MC4-R Ki (nM) | MC1-R Ki (nM) |
|---|---|---|---|---|
| 44 | 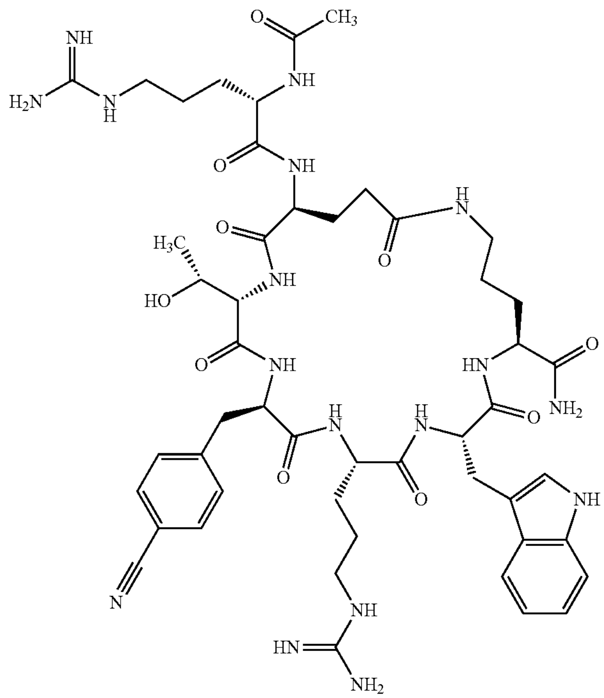 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(C#N)cc2)NC(=O)[C@H]([C@@H](C)O)NC1=O] | Ac-Arg-cyclo(Glu-Thr-D-Phe(4-CN)-Arg-Trp-Orn)-NH$_2$ (SEQ ID NO: 49) | 18 | 1625 |
| 45 | 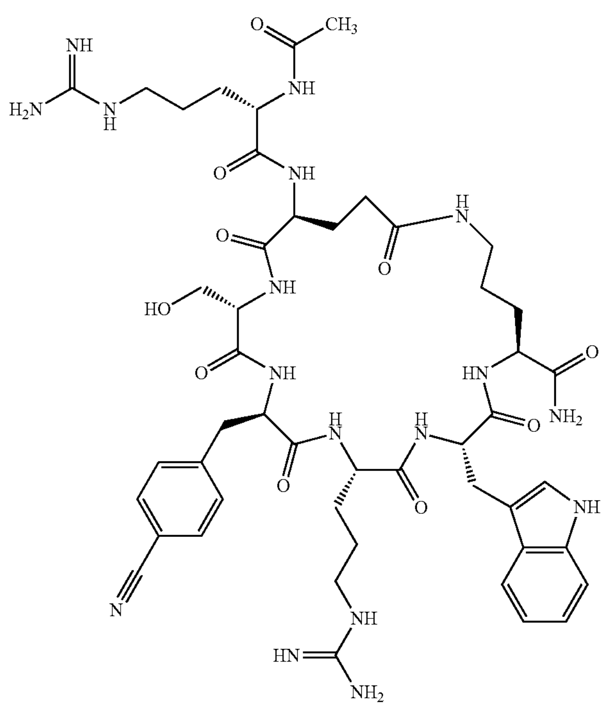 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(C#N)cc2)NC(=O)[C@H](CO)NC1=O] | Ac-Arg-cyclo(Glu-Ser-D-Phe(4-CN)-Arg-Trp-Orn)-NH$_2$ (SEQ ID NO: 50) | 10 | 10000 |

| No. | Structure | Amino Acid Sequence | MC4-R Ki (nM) | MC1-R Ki (nM) |
|---|---|---|---|---|
| 46 | 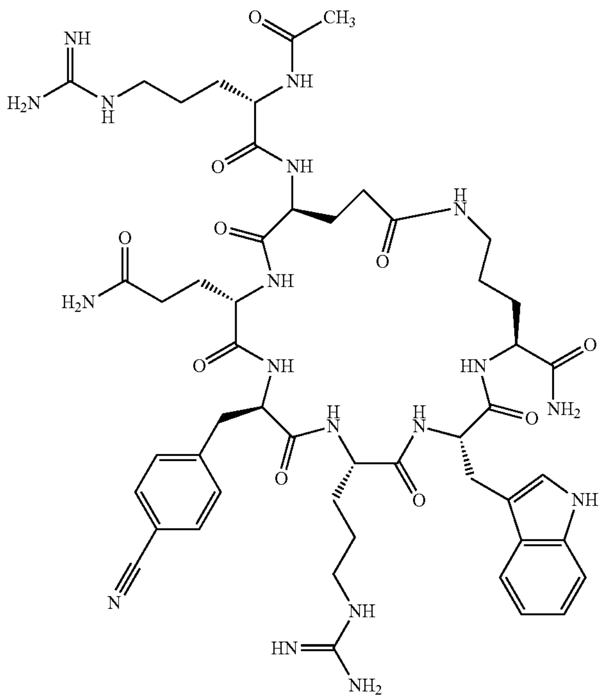 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(C#N)cc2)NC(=O)[C@H](CCC(N)=O)NC1=O] | Ac-Arg-cyclo(Glu-Gln-D-Phe(4-CN)-Arg-Trp-Orn)-NH$_2$ (SEQ ID NO: 51) | 4 | 425 |
| 47 | 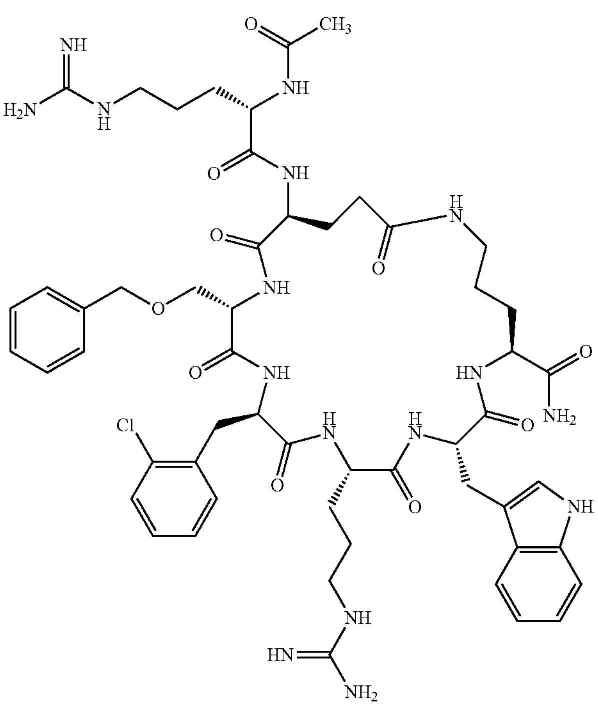 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2Cl)NC(=O)[C@H](COCc2ccccc2)NC1=O] | Ac-Arg-cyclo(Glu-Ser(Bzl)-D-Phe(2-Cl)-Arg-Trp-Orn)-NH$_2$ (SEQ ID NO: 52) | 0.3 | 25 |

| No. | Structure | Amino Acid Sequence | MC4-R Ki (nM) | MC1-R Ki (nM) |
|---|---|---|---|---|
| 48 | 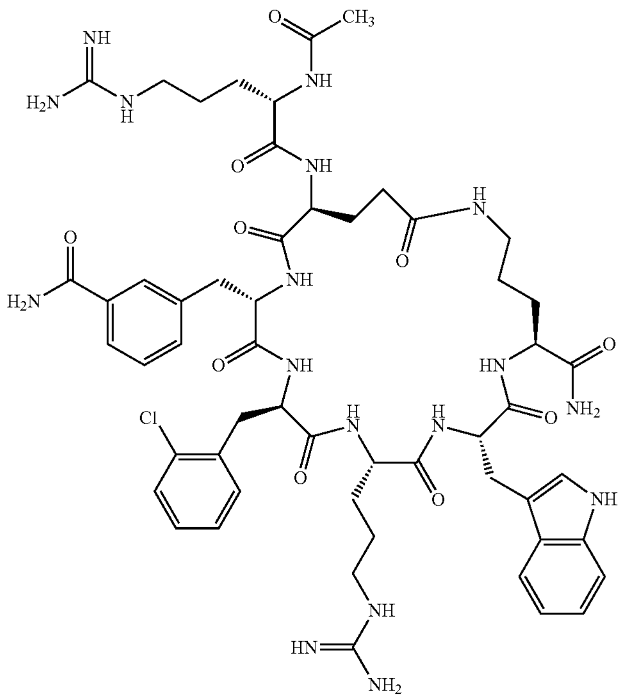 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2Cl)NC(=O)[C@H](Cc2cccc(C(N)=O)c2)NC1=O] | Ac-Arg-cyclo(Glu-Phe(3-C(=O)—NH₂)-D-Phe(2-Cl)-D-Phe-Arg-Trp-Orn)-NH₂ (SEQ ID NO: 53) | 15 | 545 |
| 49 | 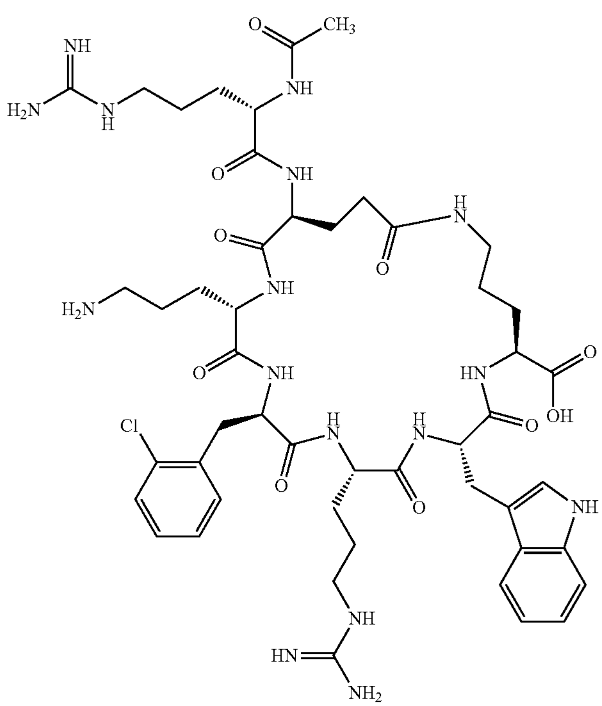 [SMILES: CC(=O)N[C@@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccccc2Cl)NC(=O)[C@H](CCCN)NC1=O] | Ac-Arg-cyclo(Glu-Orn-D-Phe(2-Cl)-Arg-Trp-Orn)-OH (SEQ ID NO: 54) | 8 | 8 |

| No. | Structure | Amino Acid Sequence | MC4-R Ki (nM) | MC1-R Ki (nM) |
|---|---|---|---|---|
| 50 | 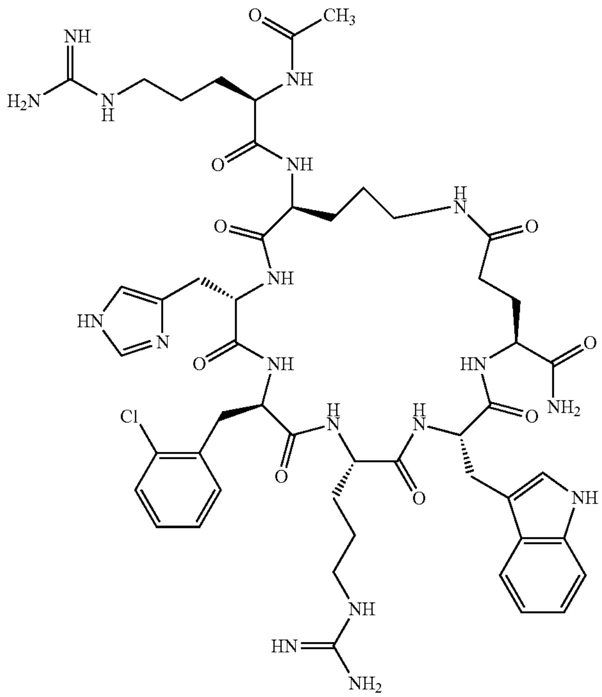 | Ac-D-Arg-cyclo(Orn-His-D-Phe(2-Cl)-Arg-Trp-Glu)-NH$_2$ (SEQ ID NO: 55) | 1 | 2 |
| 51 | 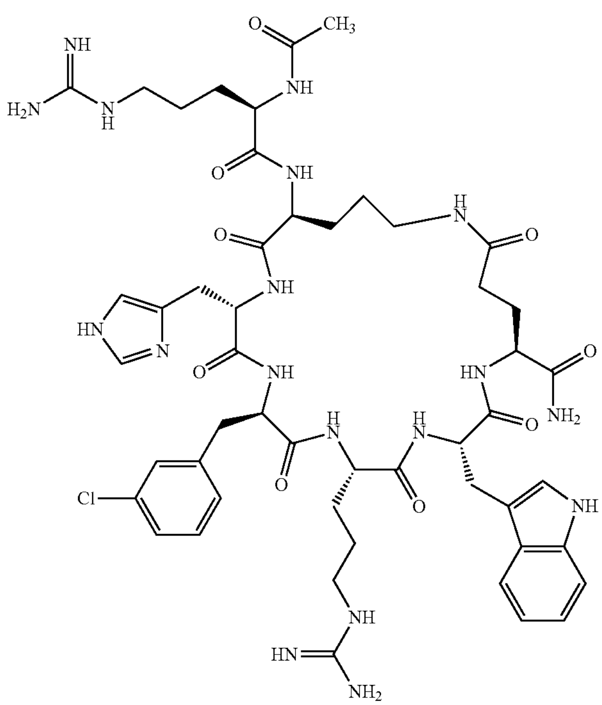 [SMILES: CC(=O)N[C@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2cccc(Cl)c2)NC(=O)[C@H](Cc2c[nH]cn2)NC1=O] | Ac-D-Arg-cyclo(Orn-His-D-Phe(3-Cl)-Arg-Trp-Glu)-NH$_2$ (SEQ ID NO: 56) | 0.6 | 3 |

-continued

| No. | Structure | Amino Acid Sequence | MC4-R Ki (nM) | MC1-R Ki (nM) |
|---|---|---|---|---|
| 52 | 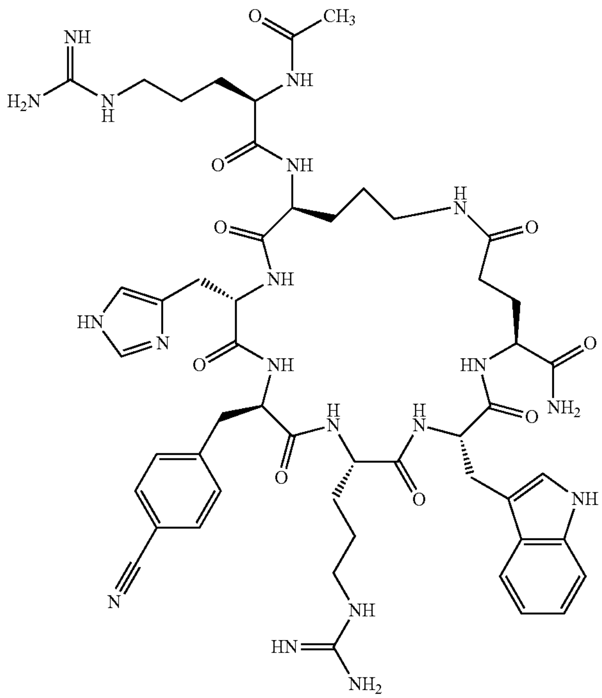 [SMILES: CC(=O)N[C@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccc(C#N)cc2)NC(=O)[C@H](Cc2c[nH]cn2)NC1=O] | Ac-D-Arg-cyclo(Orn-His-D-Phe(4-CN)-Arg-Trp-Glu)-NH$_2$ (SEQ ID NO: 57) | 0.6 | 6 |
| 53 | 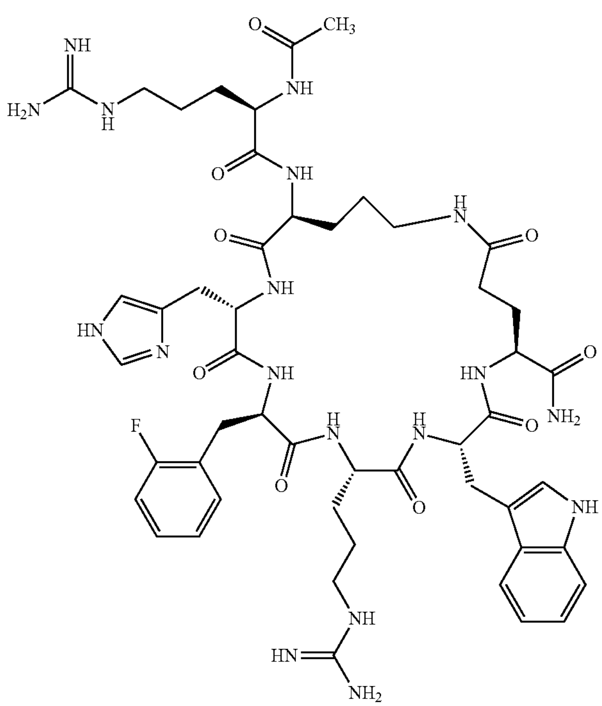 [SMILES: CC(=O)N[C@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2F)NC(=O)[C@H](Cc2c[nH]cn2)NC1=O] | Ac-D-Arg-cyclo(Orn-His-D-Phe(2-F)-Arg-Trp-Glu)-NH$_2$ (SEQ ID NO: 58) | 0.95 | 0.75 |

| No. | Structure | Amino Acid Sequence | MC4-R Ki (nM) | MC1-R Ki (nM) |
|---|---|---|---|---|
| 54 | 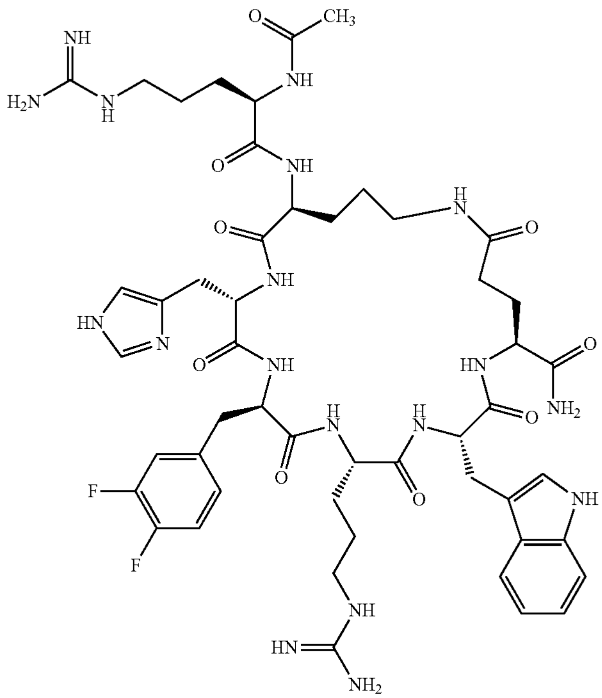 [SMILES: CC(=O)N[C@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccc(F)c(F)c2)NC(=O)[C@H](Cc2c[nH]cn2)NC1=O] | Ac-D-Arg-cyclo(Orn-His-D-Phe(3,4-diF)-Arg-Trp-Glu)-NH$_2$ (SEQ ID NO: 59) | 0.25 | 0.7 |
| 55 | 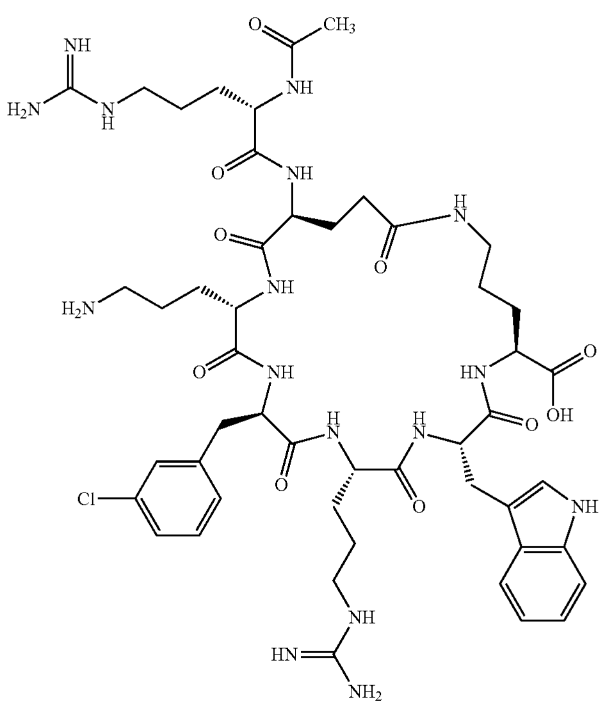 [SMILES: CC(=O)N[C@@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2cccc(Cl)c2)NC(=O)[C@H](CCCN)NC1=O] | Ac-Arg-cyclo(Glu-Orn-D-Phe(3-Cl)-Arg-Trp-Orn)-OH (SEQ ID NO: 60) | 20 | 23 |

| No. | Structure | Amino Acid Sequence | MC4-R Ki (nM) | MC1-R Ki (nM) |
|---|---|---|---|---|
| 56 | 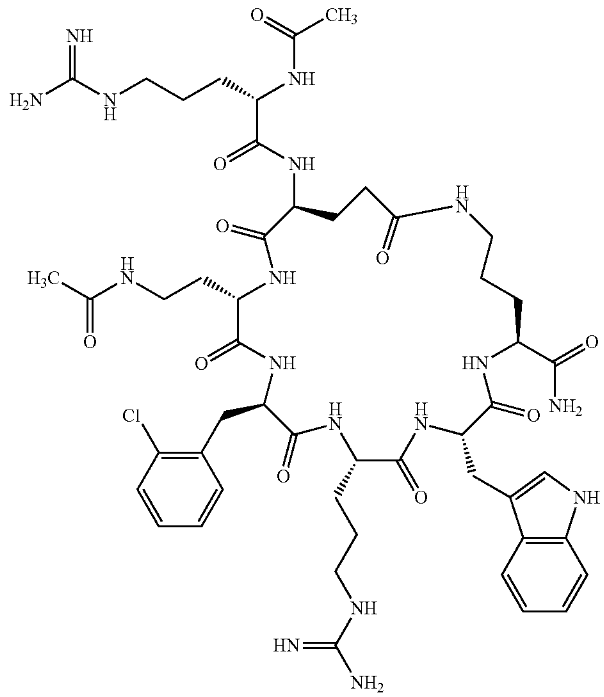 [SMILES: CC(=O)NCC[C@@H]1NC(=O)[C@@H](NC(=O)[C@H](CCCNC(=N)N)NC(C)=O)CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2Cl)NC1=O] | Ac-Arg-cyclo(Glu-Dab(Acetyl)-D-Phe(2-Cl)-Arg-Trp-Orn)-NH$_2$ (SEQ ID NO: 61) | 11 | 30 |
| 57 | 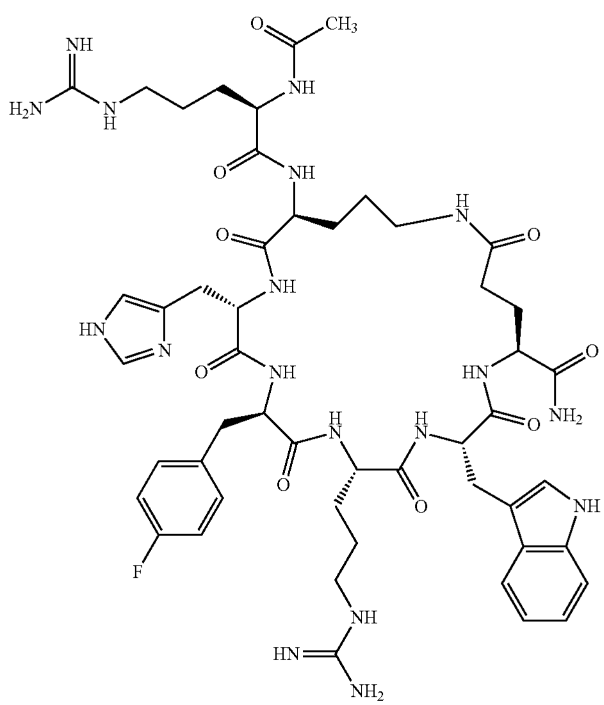 [SMILES: CC(=O)N[C@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccc(F)cc2)NC(=O)[C@H](Cc2c[nH]cn2)NC1=O] | Ac-D-Arg-cyclo(Orn-His-D-Phe(4-F)-Arg-Trp-Glu)-NH$_2$ (SEQ ID NO: 62) | 0.65 | 1 |

| No. | Structure | Amino Acid Sequence | MC4-R Ki (nM) | MC1-R Ki (nM) |
|---|---|---|---|---|
| 58 | 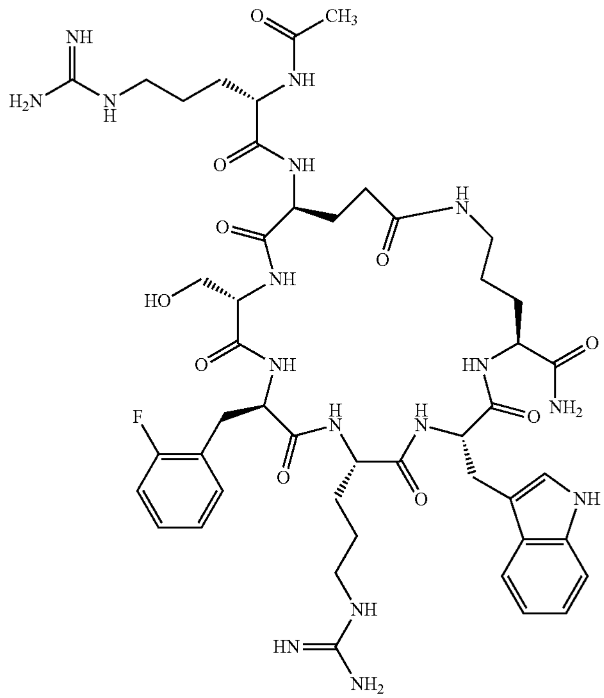 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2F)NC(=O)[C@H](CO)NC1=O] | Ac-Arg-cyclo(Glu-Ser-D-Phe(2-F)-Arg-Trp-Orn)-NH$_2$ (SEQ ID NO: 63) | 15 | 138 |
| 59 | 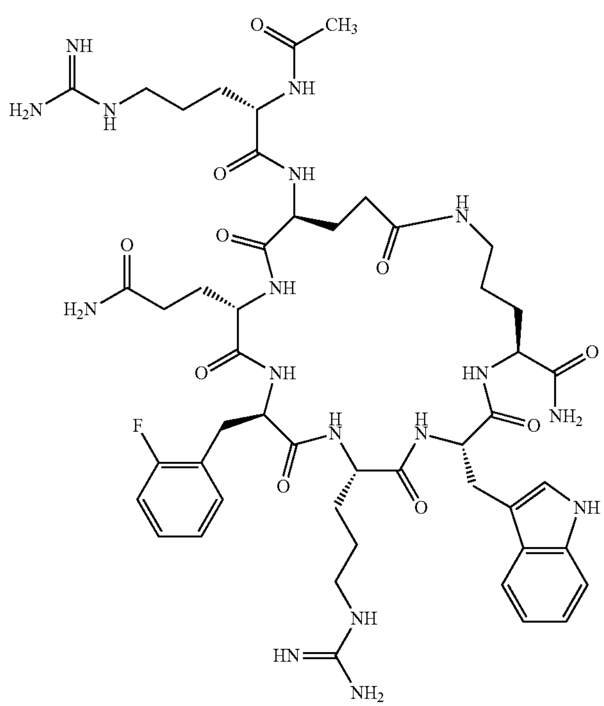 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2F)NC(=O)[C@H](CCC(N)=O)NC1=O] | Ac-Arg-cyclo(Glu-Gln-D-Phe(2-F)-Arg-Trp-Orn)-NH$_2$ (SEQ ID NO: 64) | 7 | 58 |

-continued

| No. | Structure | Amino Acid Sequence | MC4-R Ki (nM) | MC1-R Ki (nM) |
|---|---|---|---|---|
| 60 | 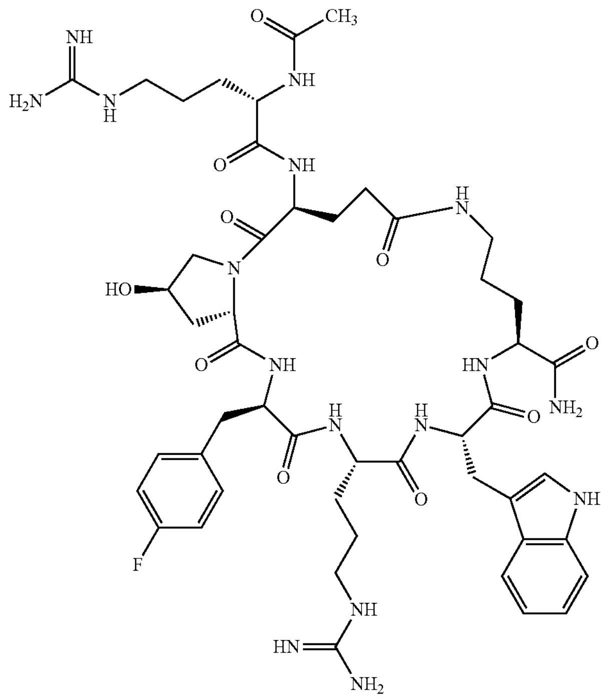 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(F)cc2)NC(=O)[C@@H]2C[C@@H](O)CN2C1=O] | Ac-Arg-cyclo(Glu-Hyp-D-Phe(4-F)-Arg-Trp-Orn)-NH$_2$ (SEQ ID NO: 65) | 1 | 89 |
| 61 | 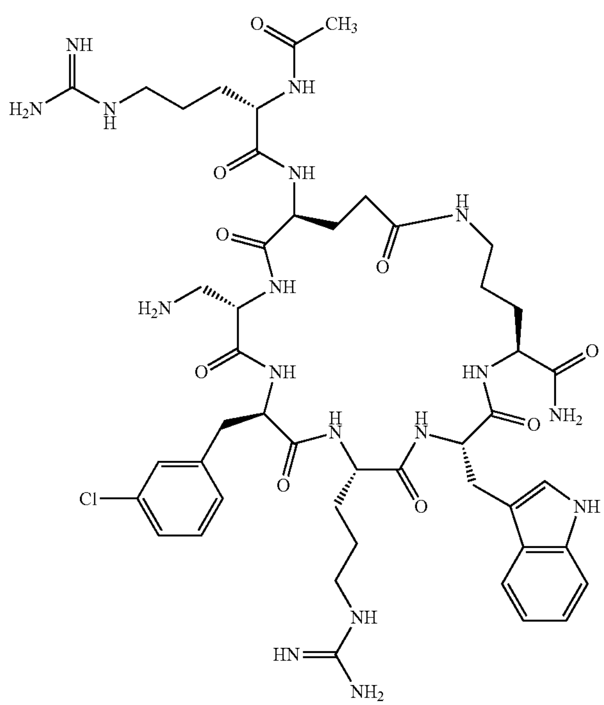 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2cccc(Cl)c2)NC(=O)[C@H](CN)NC1=O] | Ac-Arg-cyclo(Glu-Dap-D-Phe(3-Cl)-Arg-Trp-Orn)-NH$_2$ (SEQ ID NO: 66) | 4 | 25 |

| No. | Structure | Amino Acid Sequence | MC4-R Ki (nM) | MC1-R Ki (nM) |
|-----|-----------|---------------------|---------------|---------------|
| 62 | 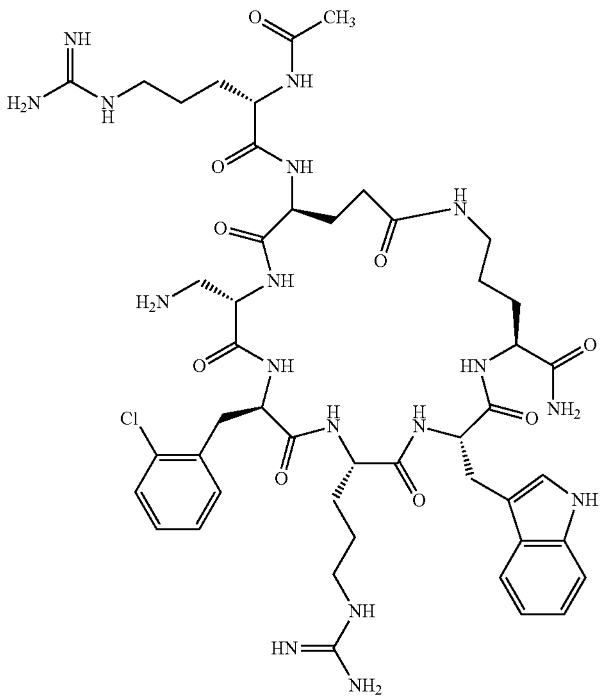 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2Cl)NC(=O)[C@H](CN)NC1=O] | Ac-Arg-cyclo(Glu-Dap-D-Phe(2-Cl)-Arg-Trp-Orn)-NH$_2$ (SEQ ID NO: 67) | 9 | 28 |
| 63 | 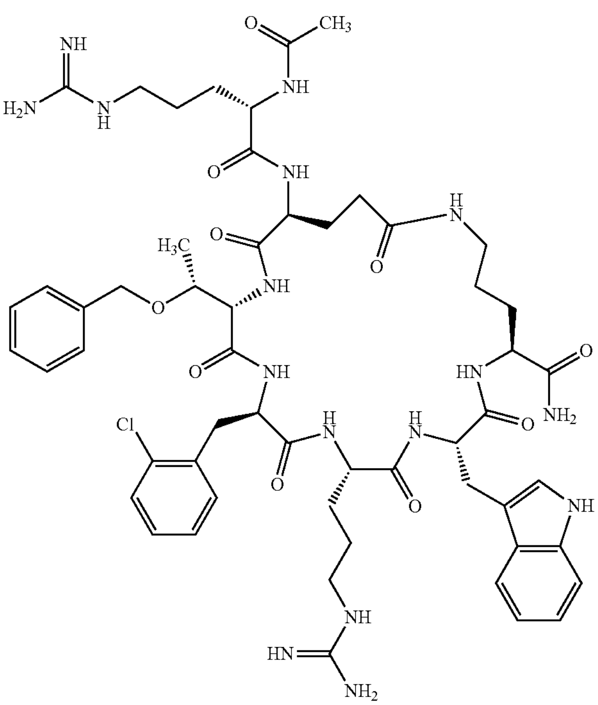 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2Cl)NC(=O)[C@H]([C@@H](C)OCc2ccccc2)NC1=O] | Ac-Arg-cyclo(Glu-Thr(Bzl)-D-Phe(2-Cl)-Arg-Trp-Orn)-NH$_2$ (SEQ ID NO: 68) | 0.35 | 12 |

| No. | Structure | Amino Acid Sequence | MC4-R Ki (nM) | MC1-R Ki (nM) |
|---|---|---|---|---|
| 64 | 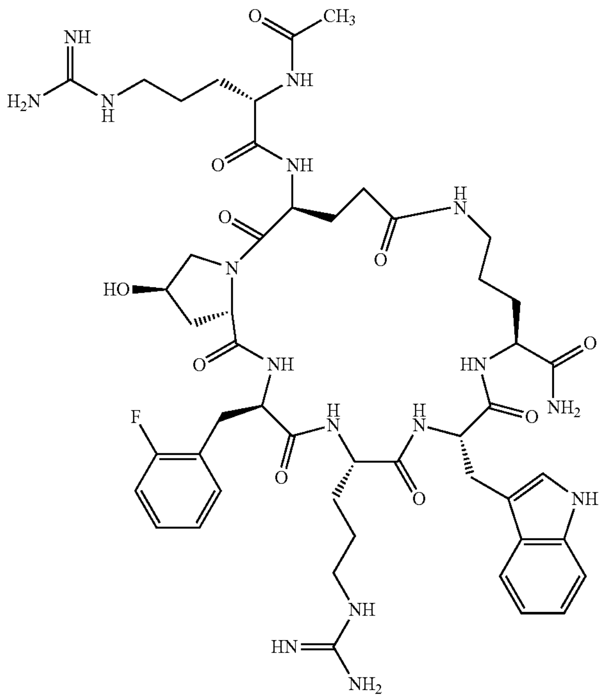 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2F)NC(=O)[C@@H]2C[C@@H](O)CN2C1=O] | Ac-Arg-cyclo(Glu-Hyp-D-Phe(2-F)-Arg-Trp-Orn)-NH$_2$ (SEQ ID NO: 69) | 3 | 53 |
| 65 | 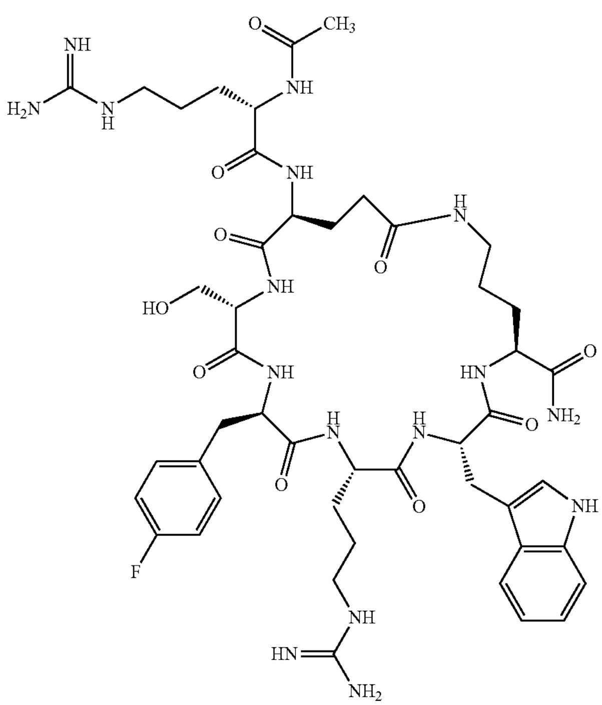 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(F)cc2)NC(=O)[C@H](CO)NC1=O] | Ac-Arg-cyclo(Glu-Ser-D-Phe(4-F)-Arg-Trp-Orn)-NH$_2$ (SEQ ID NO: 70) | 5 | 43 |

| No. | Structure | Amino Acid Sequence | MC4-R Ki (nM) | MC1-R Ki (nM) |
|---|---|---|---|---|
| 66 | 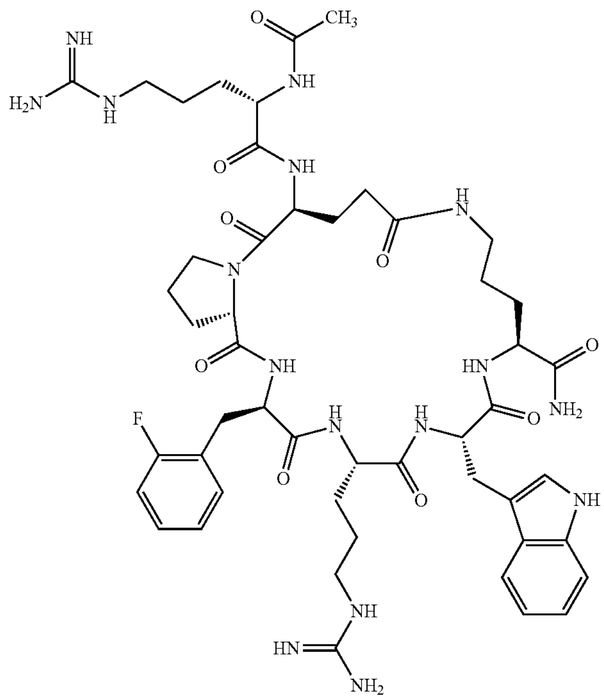 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2F)NC(=O)[C@@H]2CCCN2C1=O] | Ac-Arg-cyclo(Glu-Pro-D-Phe(2-F)-Arg-Trp-Orn)-NH$_2$ (SEQ ID NO: 71) | 6 | 95 |
| 67 | 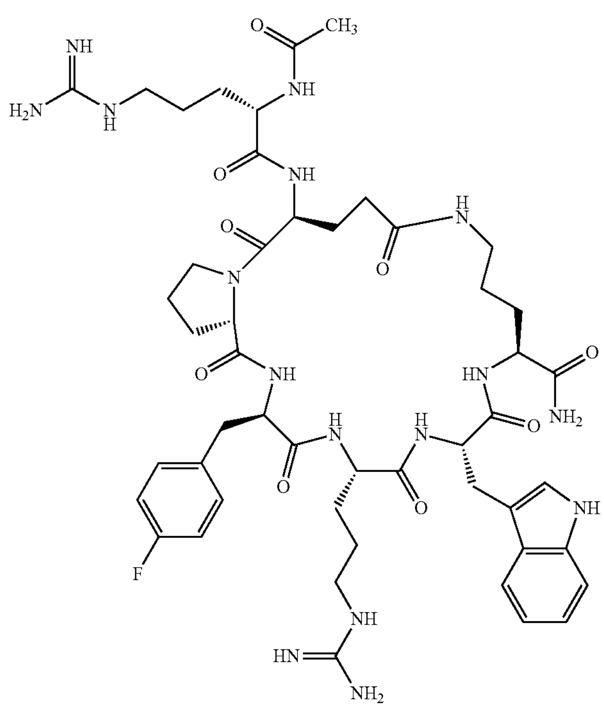 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(F)cc2)NC(=O)[C@@H]2CCCN2C1=O] | Ac-Arg-cyclo(Glu-Pro-D-Phe(4-F)-Arg-Trp-Orn)-NH$_2$ (SEQ ID NO: 72) | 5 | 130 |

| No. | Structure | Amino Acid Sequence | MC4-R Ki (nM) | MC1-R Ki (nM) |
|---|---|---|---|---|
| 68 | 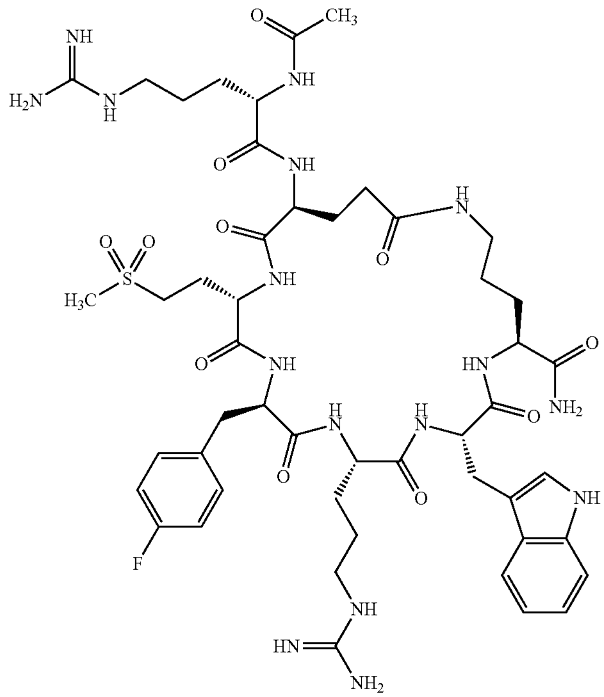 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(F)cc2)NC(=O)[C@H](CCS(C)(=O)=O)NC1=O] | Ac-Arg-cyclo(Glu-Met(O₂)-D-Phe(4-F)-Arg-Trp-Orn)-NH₂ (SEQ ID NO: 73) | 2 | 33 |
| 69 | 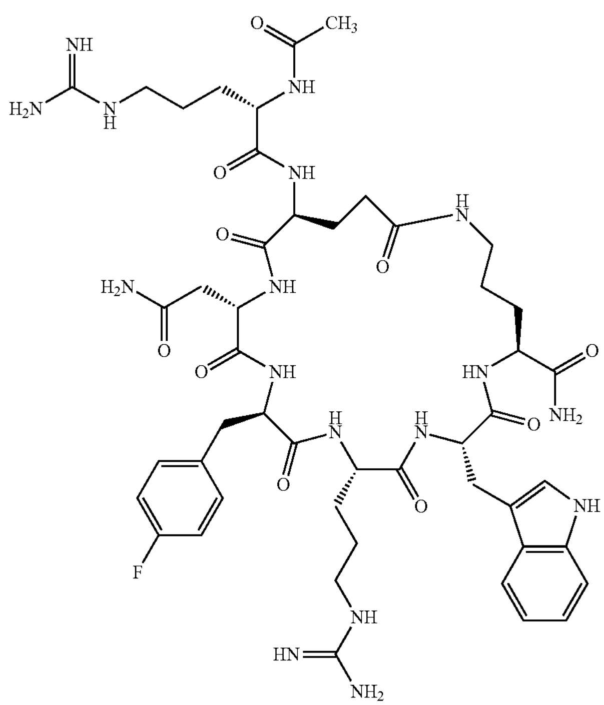 | Ac-Arg-cyclo(Glu-Asn-D-Phe(4-F)-Arg-Trp-Orn)-NH₂ (SEQ ID NO: 74) | 3 | 150 |

| No. | Structure | Amino Acid Sequence | MC4-R Ki (nM) | MC1-R Ki (nM) |
|---|---|---|---|---|
| 70 | 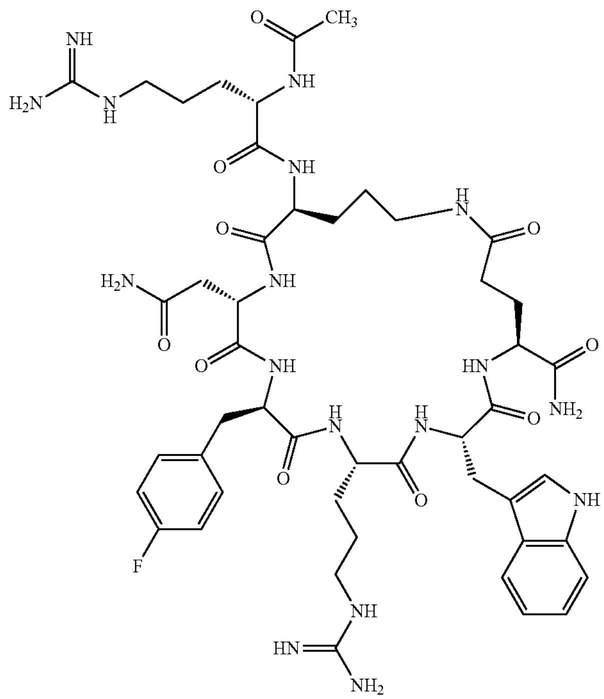 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccc(F)cc2)NC(=O)[C@H](CC(N)=O)NC1=O] | Ac-Arg-cyclo(Orn-Asn-D-Phe(4-F)-Arg-Trp-Glu)-NH$_2$ (SEQ ID NO: 75) | 3 | 170 |
| 71 | 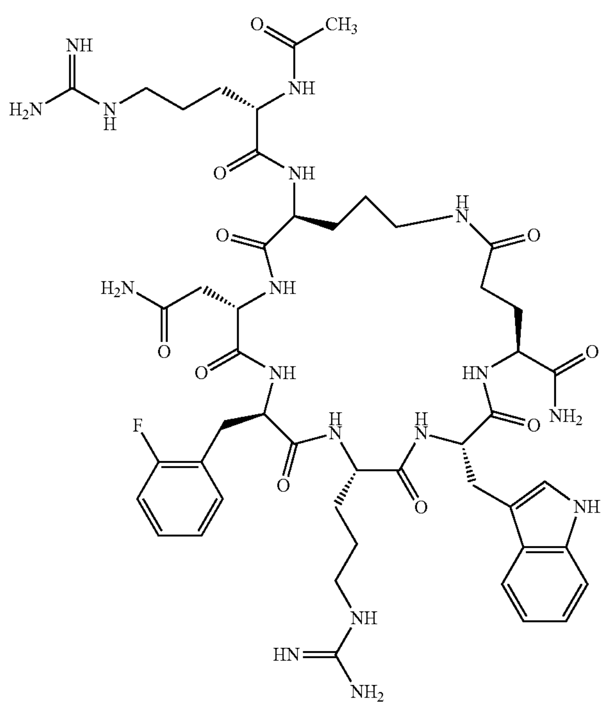 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2F)NC(=O)[C@H](CC(N)=O)NC1=O] | Ac-Arg-cyclo(Orn-Asn-D-Phe(2-F)-Arg-Trp-Glu)-NH$_2$ (SEQ ID NO: 76) | 9 | 335 |

-continued

| No. | Structure | Amino Acid Sequence | MC4-R Ki (nM) | MC1-R Ki (nM) |
|---|---|---|---|---|
| 72 | 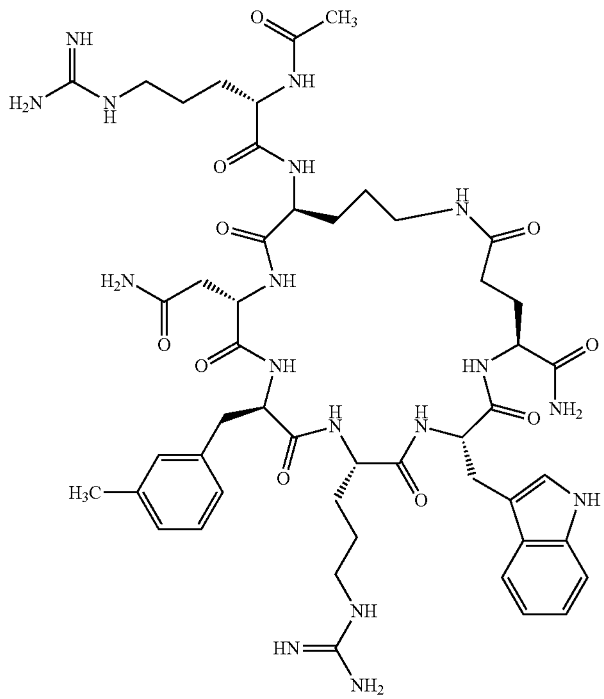 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2cccc(C)c2)NC(=O)[C@H](CC(N)=O)NC1=O] | Ac-Arg-cyclo(Orn-Asn-D-Phe(3-Me)-Arg-Trp-Glu)-NH$_2$ (SEQ ID NO: 77) | 4 | 2300 |
| 73 | 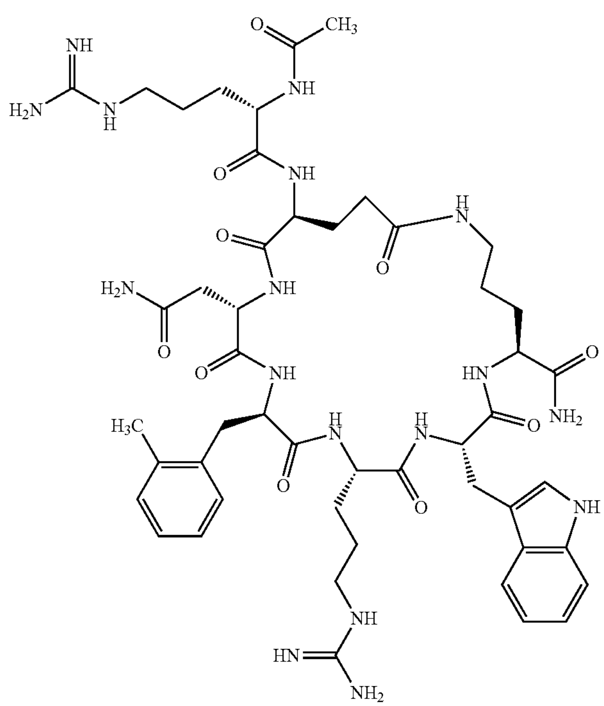 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2C)NC(=O)[C@H](CC(N)=O)NC1=O] | Ac-Arg-cyclo(Glu-Asn-D-Phe(2-Me)-Arg-Trp-Orn)-NH$_2$ (SEQ ID NO: 78) | 4 | 160 |

-continued

| No. | Structure | Amino Acid Sequence | MC4-R Ki (nM) | MC1-R Ki (nM) |
|---|---|---|---|---|
| 74 | 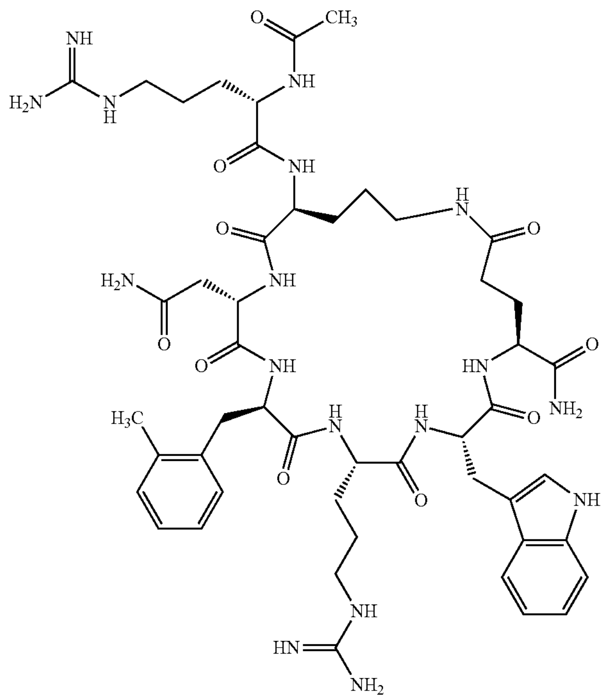 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2C)NC(=O)[C@H](CC(N)=O)NC1=O] | Ac-Arg-cyclo(Orn-Asn-D-Phe(2-Me)-Arg-Trp-Glu)-NH$_2$ (SEQ ID NO: 79) | 5 | 405 |
| 75 | 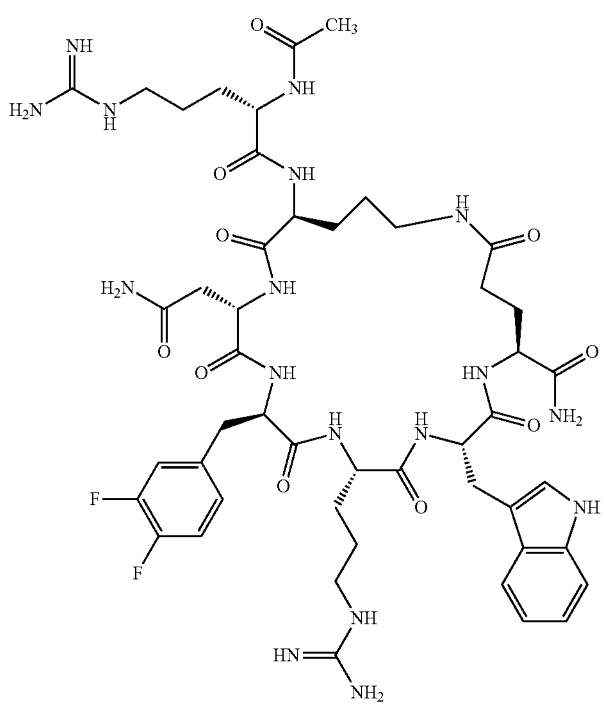 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccc(F)c(F)c2)NC(=O)[C@H](CC(N)=O)NC1=O] | Ac-Arg-cyclo(Orn-Asn-D-Phe(3,4-diF)-Arg-Trp-Glu)-NH$_2$ (SEQ ID NO: 80) | 3 | 190 |

-continued

| No. | Structure | Amino Acid Sequence | MC4-R Ki (nM) | MC1-R Ki (nM) |
|---|---|---|---|---|
| 76 | 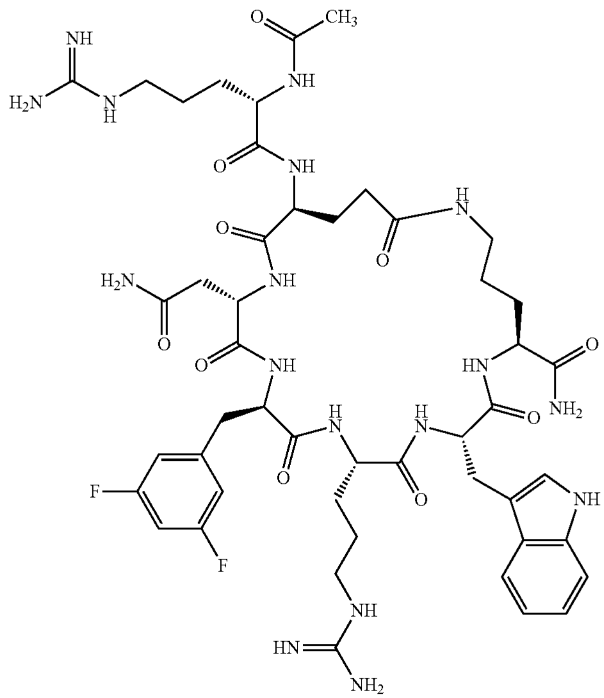 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2cc(F)cc(F)c2)NC(=O)[C@H](CC(N)=O)NC1=O] | Ac-Arg-cyclo(Glu-Asn-D-Phe(3,4-diF)-Arg-Trp-Orn)-NH$_2$ (SEQ ID NO: 81) | 20 | 260 |
| 77 | 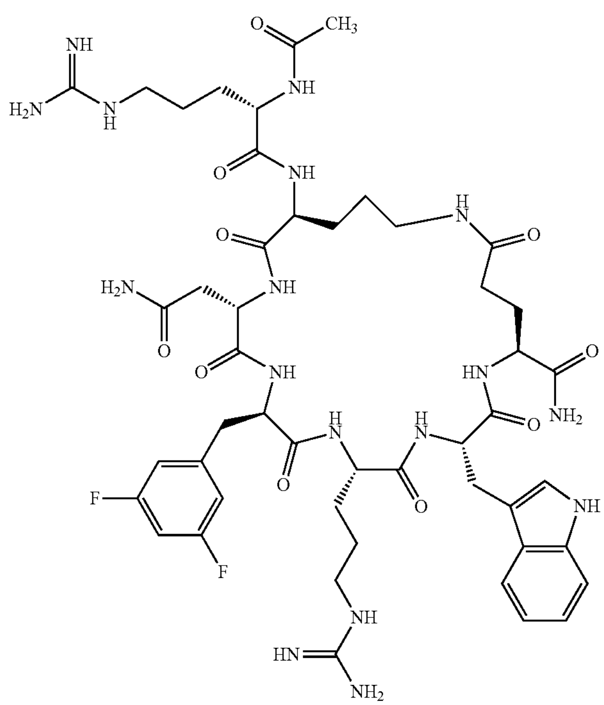 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2cc(F)cc(F)c2)NC(=O)[C@H](CC(N)=O)NC1=O] | Ac-Arg-cyclo(Orn-Asn-D-Phe(3,5-diF)-Arg-Trp-Glu)-NH$_2$ (SEQ ID NO: 82) | 8 | 190 |

-continued

| No. | Structure | Amino Acid Sequence | MC4-R Ki (nM) | MC1-R Ki (nM) |
|---|---|---|---|---|
| 78 | 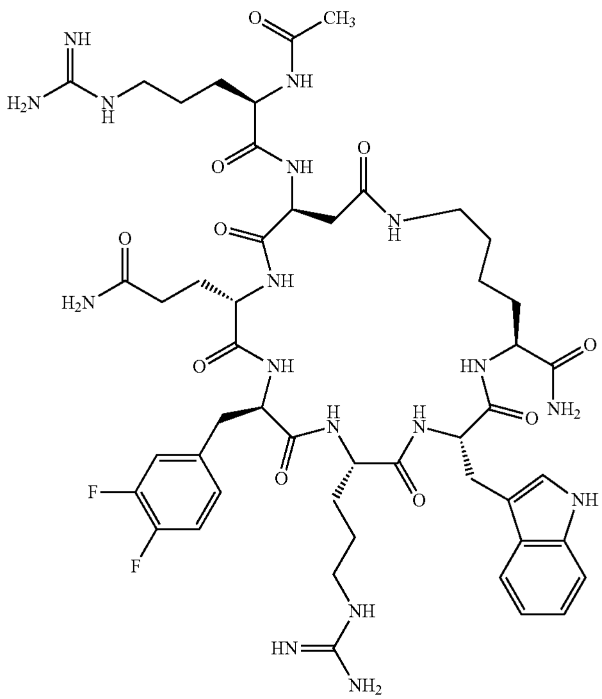 [SMILES: CC(=O)N[C@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccc(F)c(F)c2)NC(=O)[C@H](CCC(N)=O)NC1=O] | Ac-D-Arg-cyclo(Asp-Gln-D-Phe(3,4-diF)-Arg-Trp-Lys)-NH$_2$ (SEQ ID NO: 83) | 8 | 515 |
| 79 | 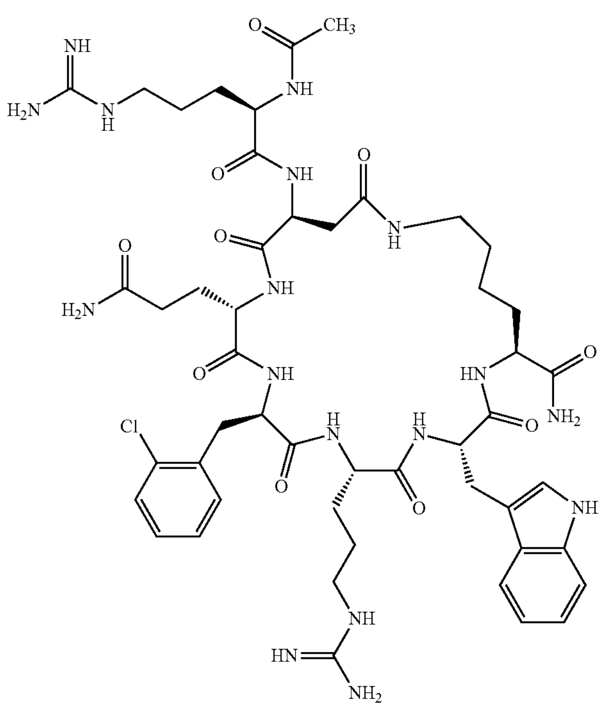 [SMILES: CC(=O)N[C@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2Cl)NC(=O)[C@H](CCC(N)=O)NC1=O] | Ac-D-Arg-cyclo(Asp-Gln-D-Phe(2-Cl)-Arg-Trp-Lys)-NH$_2$ (SEQ ID NO: 84) | 10 | 395 |

| No. | Structure | Amino Acid Sequence | MC4-R Ki (nM) | MC1-R Ki (nM) |
|---|---|---|---|---|
| 80 | 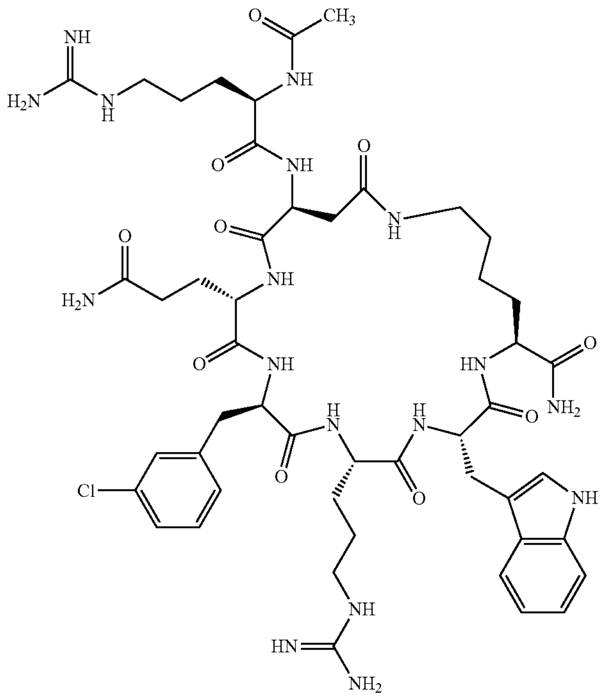 [SMILES: CC(=O)N[C@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2cccc(Cl)c2)NC(=O)[C@H](CCC(N)=O)NC1=O] | Ac-D-Arg-cyclo(Asp-Gln-D-Phe(3-Cl)-Arg-Trp-Lys)-NH₂ (SEQ ID NO: 85) | 7 | 1750 |
| 81 | 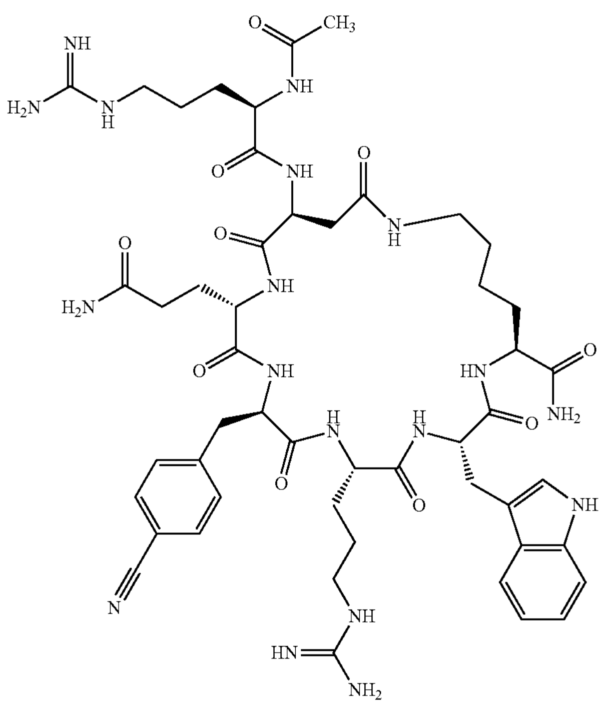 [SMILES: CC(=O)N[C@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccc(C#N)cc2)NC(=O)[C@H](CCC(N)=O)NC1=O] | Ac-D-Arg-cyclo(Asp-Gln-D-Phe(4-CN)-Arg-Trp-Lys)-NH₂ (SEQ ID NO: 86) | 13 | 10000 |

-continued

| No. | Structure | Amino Acid Sequence | MC4-R Ki (nM) | MC1-R Ki (nM) |
|---|---|---|---|---|
| 82 | 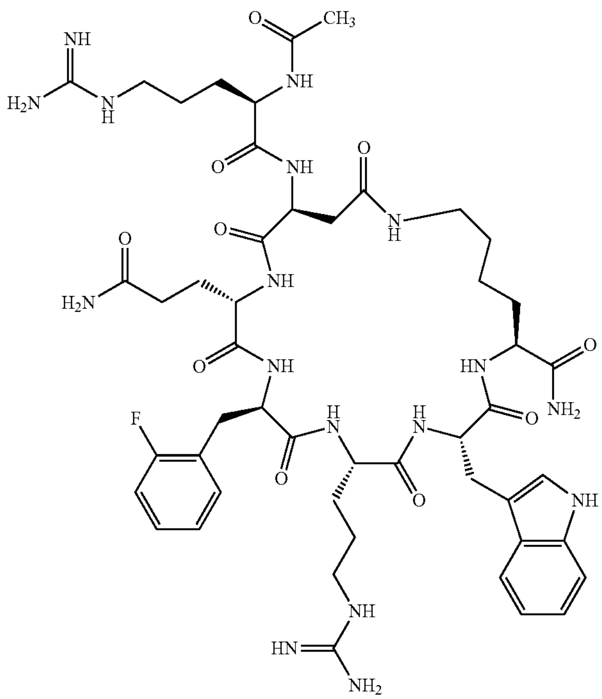 [SMILES: CC(=O)N[C@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2F)NC(=O)[C@H](CCC(N)=O)NC1=O] | Ac-D-Arg-cyclo(Asp-Gln-D-Phe(2-F)-Arg-Trp-Lys)-NH$_2$ (SEQ ID NO: 87) | 10 | 220 |
| 83 | 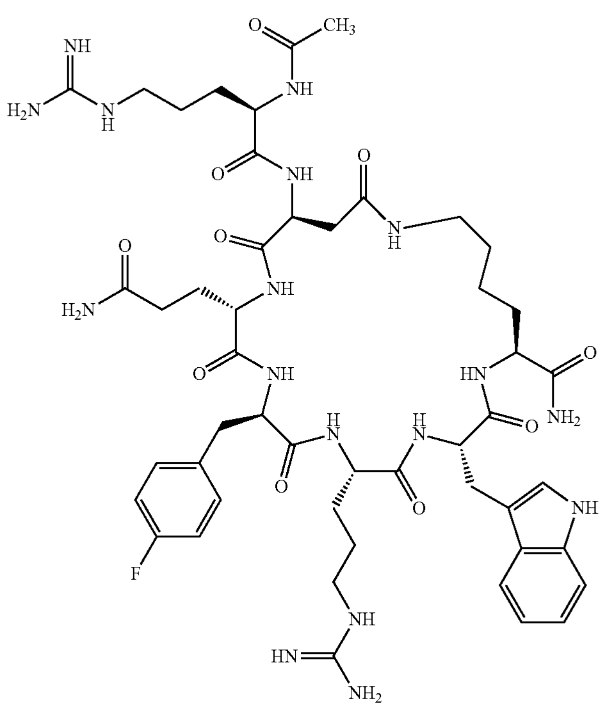 [SMILES: CC(=O)N[C@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccc(F)cc2)NC(=O)[C@H](CCC(N)=O)NC1=O] | Ac-D-Arg-cyclo(Asp-Gln-D-Phe(4-F)-Arg-Trp-Lys)-NH$_2$ (SEQ ID NO: 88) | 6 | 260 |

| No. | Structure | Amino Acid Sequence | MC4-R Ki (nM) | MC1-R Ki (nM) |
|---|---|---|---|---|
| 84 | 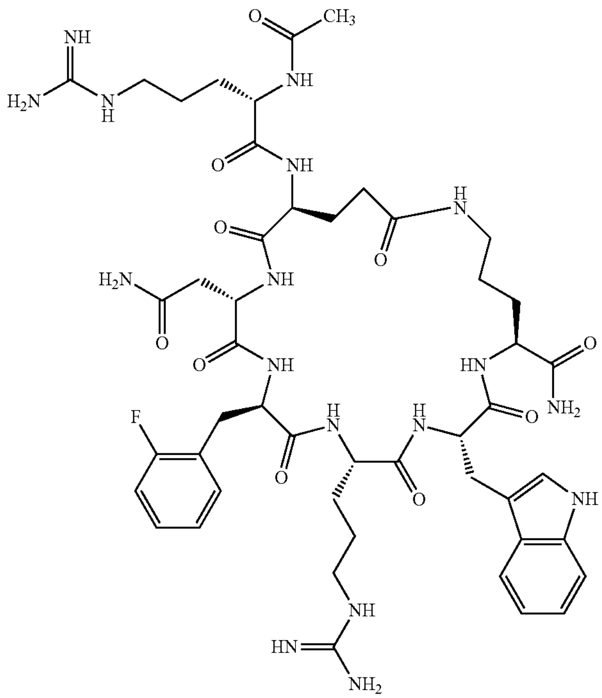 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2F)NC(=O)[C@H](CC(N)=O)NC1=O] | Ac-Arg-cyclo(Glu-Asn-D-Phe(2-Cl)-Arg-Trp-Orn)-NH₂ (SEQ ID NO: 89) | 7 | 245 |
| 85 | 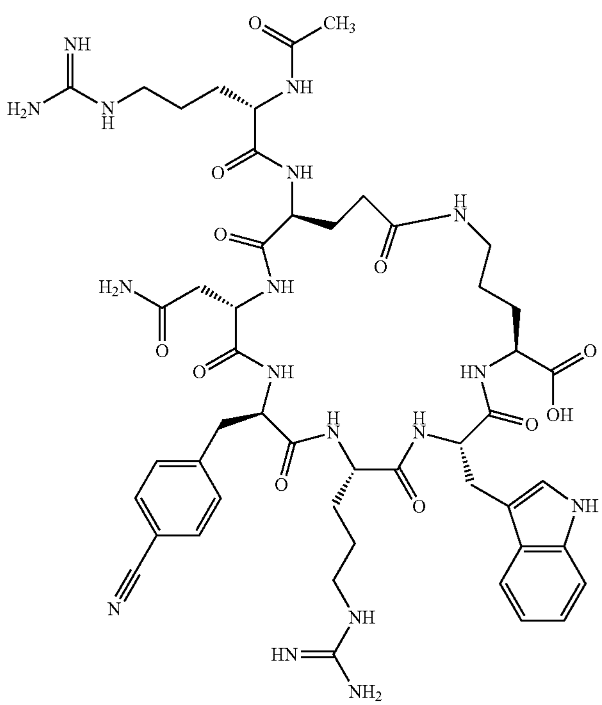 [SMILES: CC(=O)N[C@@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2ccc(C#N)cc2)NC(=O)[C@H](CC(N)=O)NC1=O] | Ac-Arg-cyclo(Glu-Asn-D-Phe(4-CN)-Arg-Trp-Orn)-OH (SEQ ID NO: 90) | 64 | 10000 |

| No. | Structure | Amino Acid Sequence | MC4-R Ki (nM) | MC1-R Ki (nM) |
|---|---|---|---|---|
| 86 | 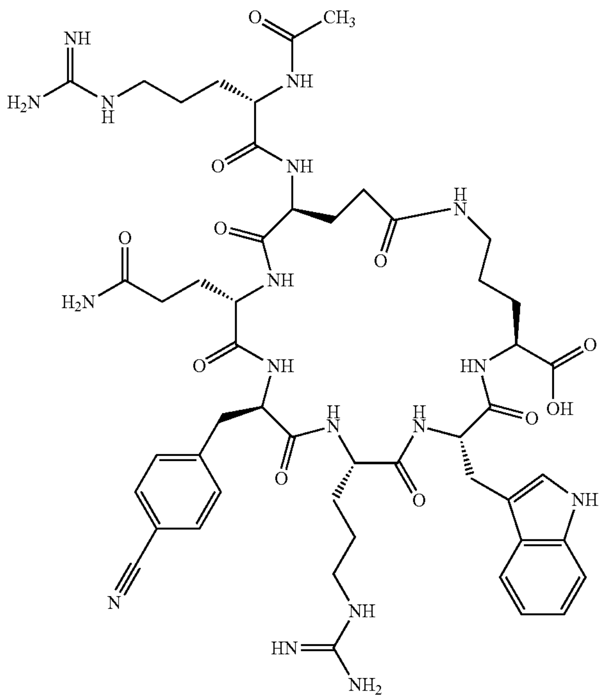 | Ac-Arg-cyclo(Glu-Gln-D-Phe(4-CN)-Arg-Trp-Orn)-OH (SEQ ID NO: 91) | 40 | 3968 |
| 87 | 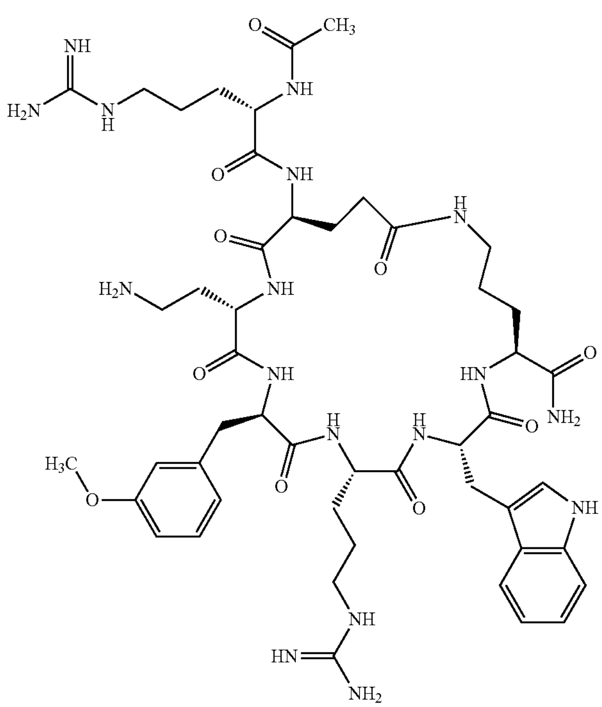 [SMILES: COc1cccc(C[C@H]2NC(=O)[C@H](CCN)NC(=O)[C@@H](NC(=O)[C@H](CCCNC(=N)N)NC(C)=O)CCC(=O)NCCC[C@@H](C(N)=O)NC(=O)[C@H](Cc3c[nH]c4ccccc34)NC(=O)[C@H](CCCNC(=N)N)NC2=O)c1] | Ac-Arg-cyclo(Glu-Dab-D-Phe(3-OMe)-Arg-Trp-Orn)-NH$_2$ (SEQ ID NO: 92) | 3 | — |

| No. | Structure | Amino Acid Sequence | MC4-R Ki (nM) | MC1-R Ki (nM) |
|---|---|---|---|---|
| 88 | 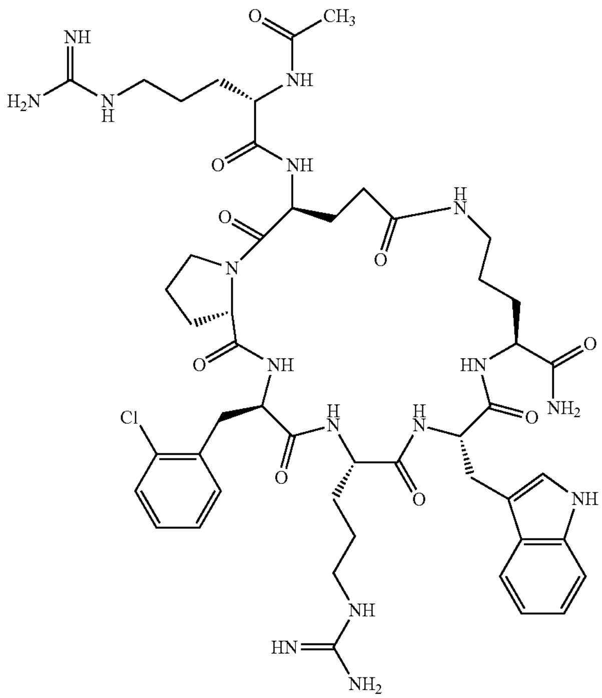 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2Cl)NC(=O)[C@@H]2CCCN2C1=O] | Ac-Arg-cyclo(Glu-Pro-D-Phe(2-Cl)-Arg-Trp-Orn)-NH$_2$ (SEQ ID NO: 93) | 5 | — |
| 89 | 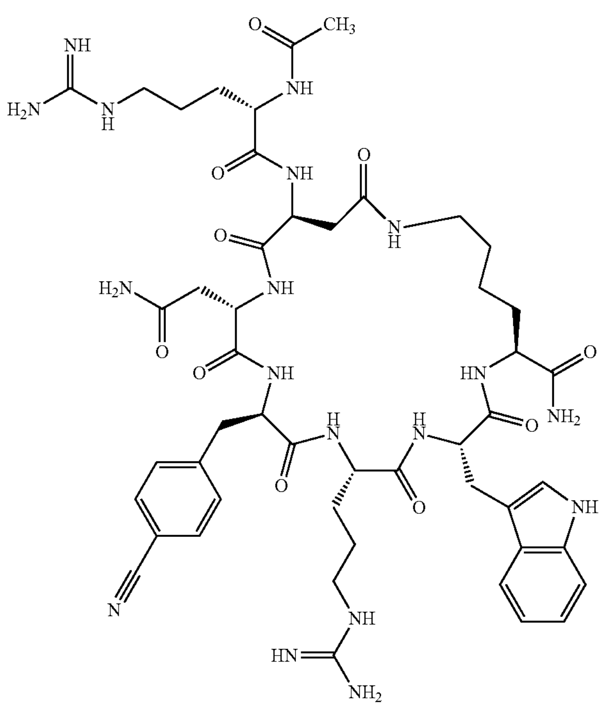 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccc(C#N)cc2)NC(=O)[C@H](CC(N)=O)NC1=O] | Ac-Arg-cyclo(Asp-Asn-D-Phe(4-CN)-Arg-Trp-Lys)-NH$_2$ (SEQ ID NO: 94) | 48 | — |

| No. | Structure | Amino Acid Sequence | MC4-R Ki (nM) | MC1-R Ki (nM) |
|---|---|---|---|---|
| 90 | 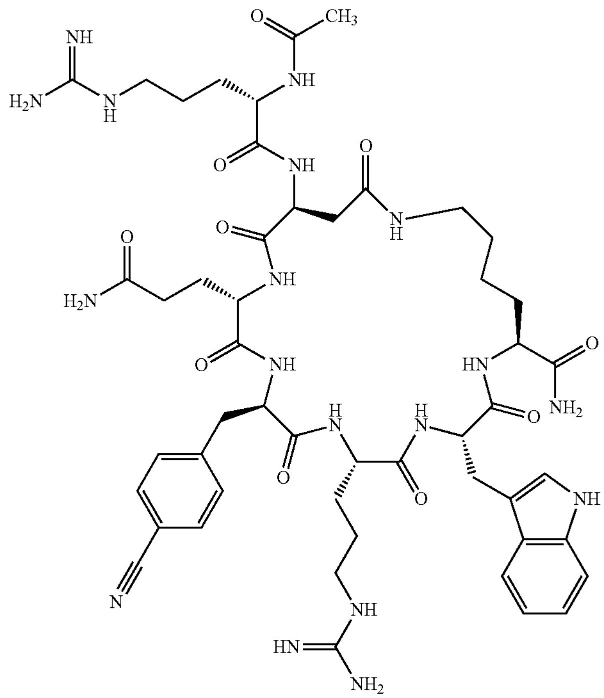 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccc(C#N)cc2)NC(=O)[C@H](CCC(N)=O)NC1=O] | Ac-Arg-cyclo(Asp-Gln-D-Phe(4-CN)-Arg-Trp-Lys)-NH$_2$ (SEQ ID NO: 95) | 5 | — |
| 91 | 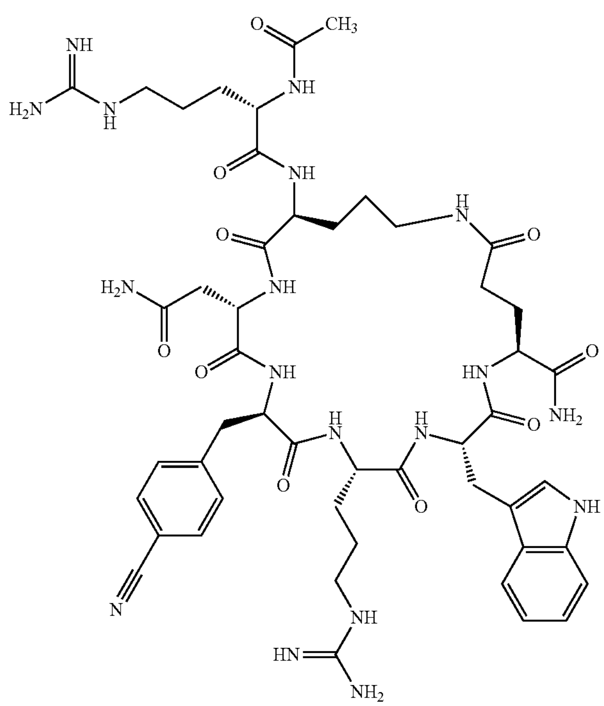 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccc(C#N)cc2)NC(=O)[C@H](CC(N)=O)NC1=O] | Ac-Arg-cyclo(Orn-Asn-D-Phe(4-CN)-Arg-Trp-Glu)-NH$_2$ (SEQ ID NO: 96) | 4 | — |

| No. | Structure | Amino Acid Sequence | MC4-R Ki (nM) | MC1-R Ki (nM) |
|---|---|---|---|---|
| 92 | 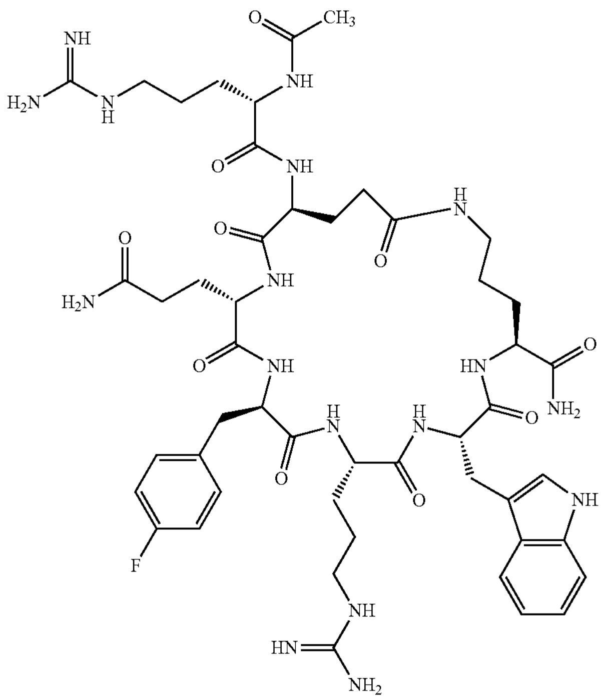 | Ac-Arg-cyclo(Glu-Gln-D-Phe(4-F)-Arg-Trp-Orn)-NH$_2$ (SEQ ID NO: 97) | 2 | — |
| 93 | 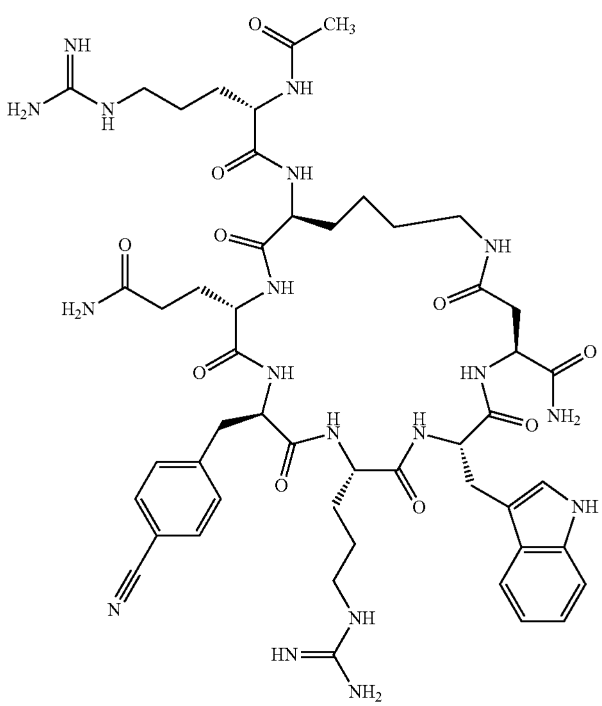 [SMILES: CC(=O)N[C@@H](CCCNC(=N)N)C(=O)N[C@H]1CCCCNC(=O)C[C@@H](C(N)=O)NC(=O)[C@H](Cc2c[nH]c3ccccc23)NC(=O)[C@H](CCCNC(=N)N)NC(=O)[C@@H](Cc2ccc(C#N)cc2)NC(=O)[C@H](CCC(N)=O)NC1=O] | Ac-Arg-cyclo(Lys-Gln-D-Phe(4-CN)-Arg-Trp-Asp)-NH$_2$ (SEQ ID NO: 98) | 1 | — |

| No. | Structure | Amino Acid Sequence | MC4-R Ki (nM) | MC1-R Ki (nM) |
|---|---|---|---|---|
| 94 | 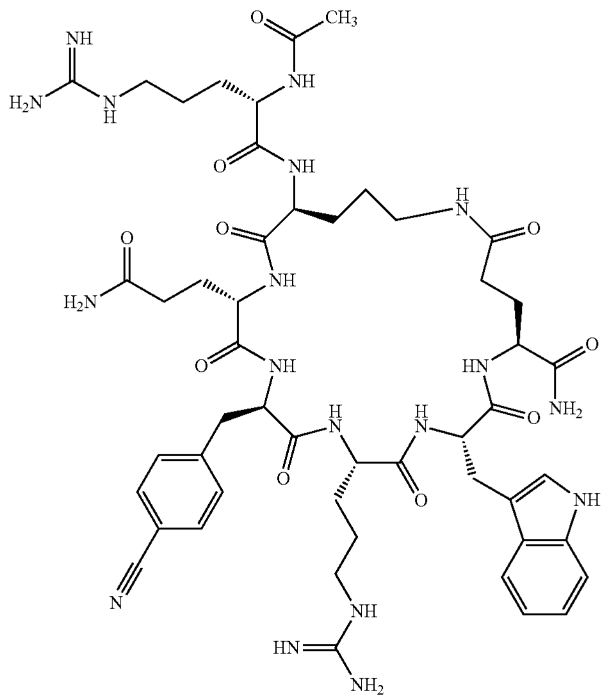 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccc(C#N)cc2)NC(=O)[C@H](CCC(N)=O)NC1=O] | Ac-Arg-cyclo(Orn-Gln-D-Phe(4-CN)-Arg-Trp-Glu)-NH$_2$ (SEQ ID NO: 99) | 0.9 | — |
| 95 | 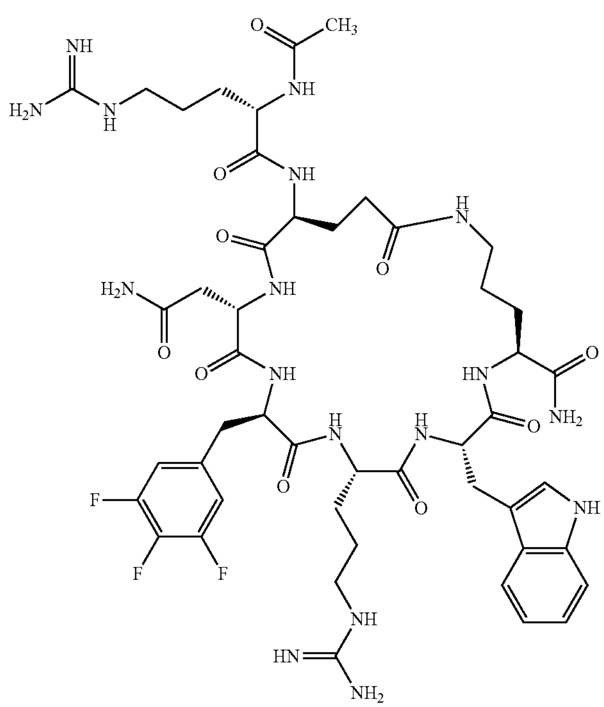 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2cc(F)c(F)c(F)c2)NC(=O)[C@H](CC(N)=O)NC1=O] | Ac-Arg-cyclo(Glu-Asn-D-Phe(3,4,5-triF)-Arg-Trp-Orn)-NH$_2$ (SEQ ID NO: 100) | 3 | — |

| No. | Structure | Amino Acid Sequence | MC4-R Ki (nM) | MC1-R Ki (nM) |
|---|---|---|---|---|
| 96 | 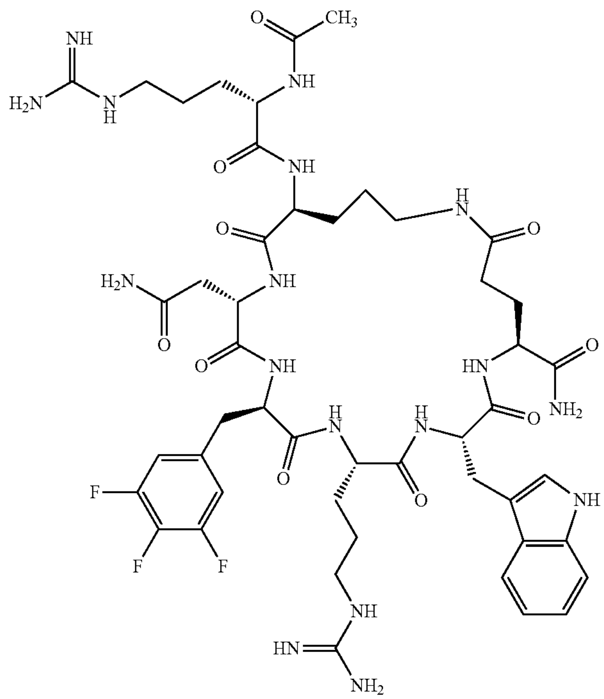 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2cc(F)c(F)c(F)c2)NC(=O)[C@H](CC(N)=O)NC1=O] | Ac-Arg-cyclo(Orn-Asn-D-Phe(3,4,5-triF)-Arg-Trp-Glu)-NH$_2$ (SEQ ID NO: 101) | 2 | — |
| 97 | 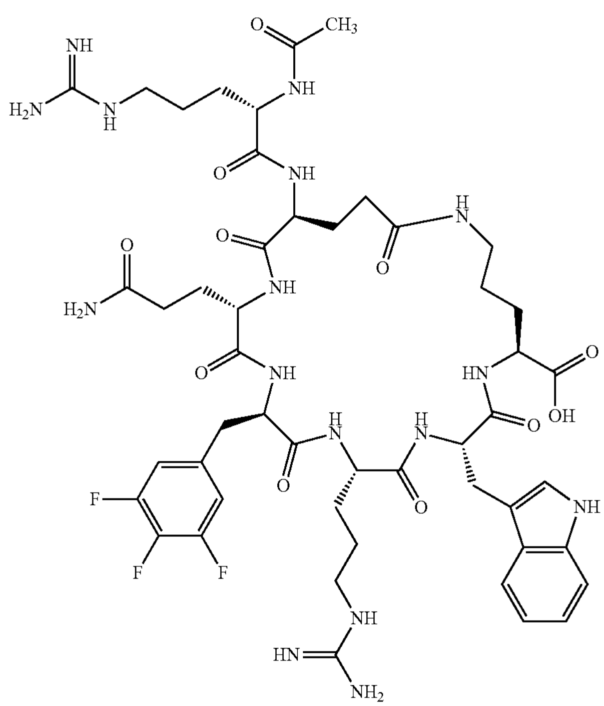 [SMILES: CC(=O)N[C@@H](CCCNC(=N)N)C(=O)N[C@H]1CCC(=O)NCCC[C@@H](C(=O)O)NC(=O)[C@H](Cc2c[nH]c3ccccc23)NC(=O)[C@H](CCCNC(=N)N)NC(=O)[C@@H](Cc2cc(F)c(F)c(F)c2)NC(=O)[C@H](CCC(N)=O)NC1=O] | Ac-Arg-cyclo(Glu-Gln-D-Phe(3,4,5-triF)-Arg-Trp-Orn)-NH$_2$ (SEQ ID NO: 102) | 0.75 | — |

| No. | Structure | Amino Acid Sequence | MC4-R Ki (nM) | MC1-R Ki (nM) |
|---|---|---|---|---|
| 98 | 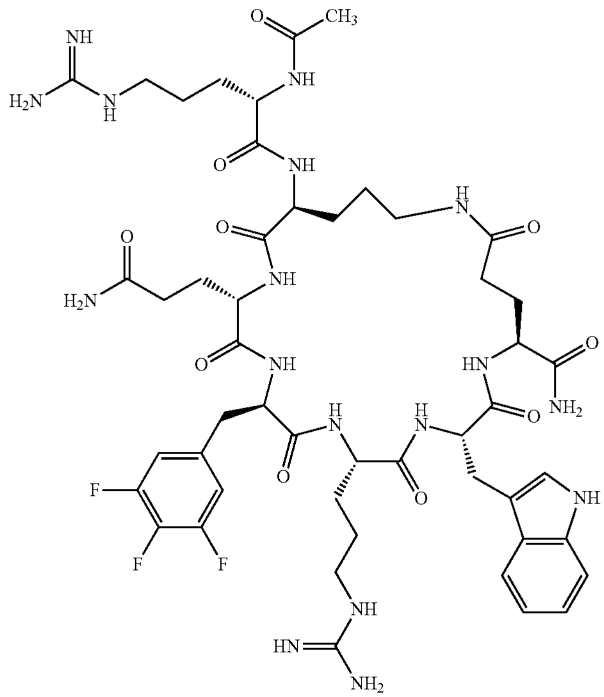 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2cc(F)c(F)c(F)c2)NC(=O)[C@H](CCC(N)=O)NC1=O] | Ac-Arg-cyclo(Orn-Gln-D-Phe(3,4,5-triF)-Arg-Trp-Glu)-NH$_2$ (SEQ ID NO: 103) | 0.75 | — |
| 99 | 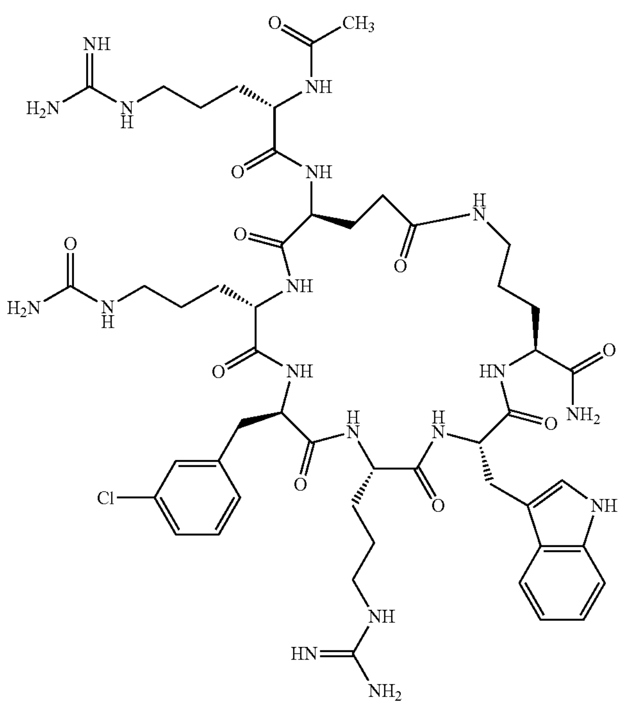 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2cccc(Cl)c2)NC(=O)[C@H](CCCNC(N)=O)NC1=O] | Ac-Arg-cyclo(Glu-Arg-D-Phe(3-Cl)-Arg-Trp-Orn)-NH$_2$ (SEQ ID NO: 104) | 0.5 | — |

| No. | Structure | Amino Acid Sequence | MC4-R Ki (nM) | MC1-R Ki (nM) |
|---|---|---|---|---|
| 100 | 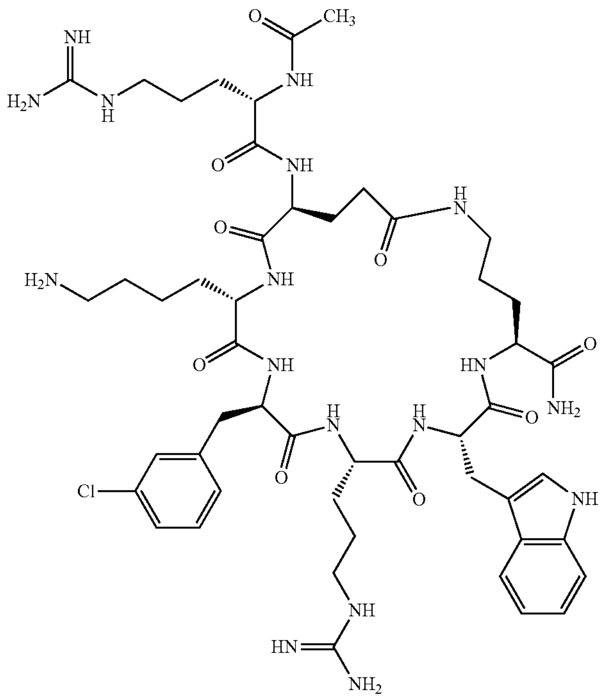 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2cccc(Cl)c2)NC(=O)[C@H](CCCCN)NC1=O] | Ac-Arg-cyclo(Glu-Lys-D-Phe(3-Cl)-Arg-Trp-Orn)-NH$_2$ (SEQ ID NO: 105) | 4 | — |
| 101 | 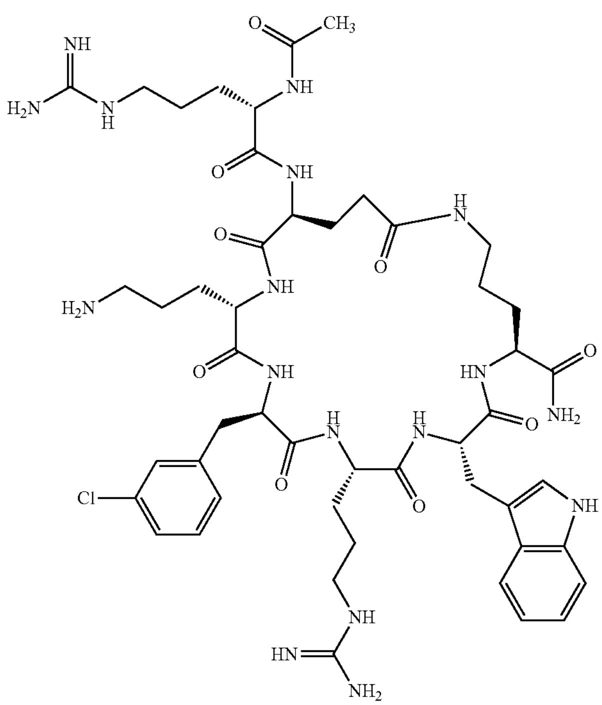 | Ac-Arg-cyclo(Glu-Orn-D-Phe(3-Cl)-Arg-Trp-Orn)-NH$_2$ (SEQ ID NO: 106) | 1 | — |

-continued

| No. | Structure | Amino Acid Sequence | MC4-R Ki (nM) | MC1-R Ki (nM) |
|---|---|---|---|---|
| 102 | 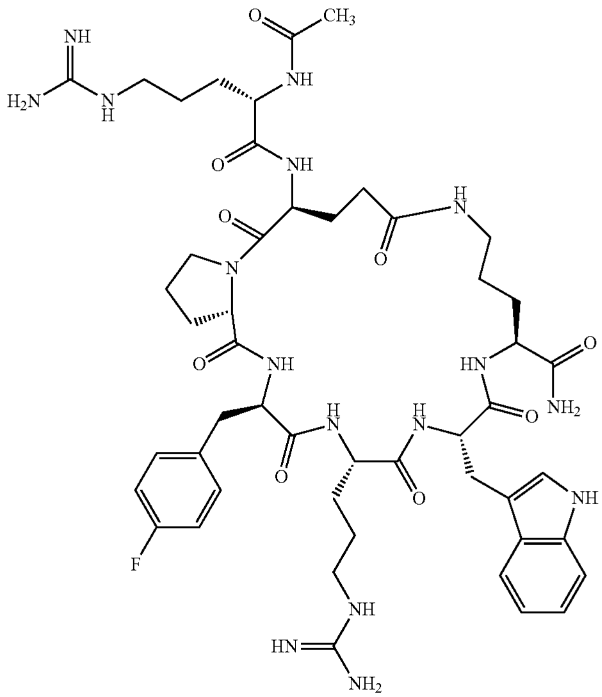 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccc(F)cc2)NC(=O)[C@@H]2CCCN2C1=O] | Ac-Arg-cyclo(Glu-Pro-D-Phe(4-F)-Arg-Trp-Orn)-OH (SEQ ID NO: 107) | 30 | 730 |
| 103 | 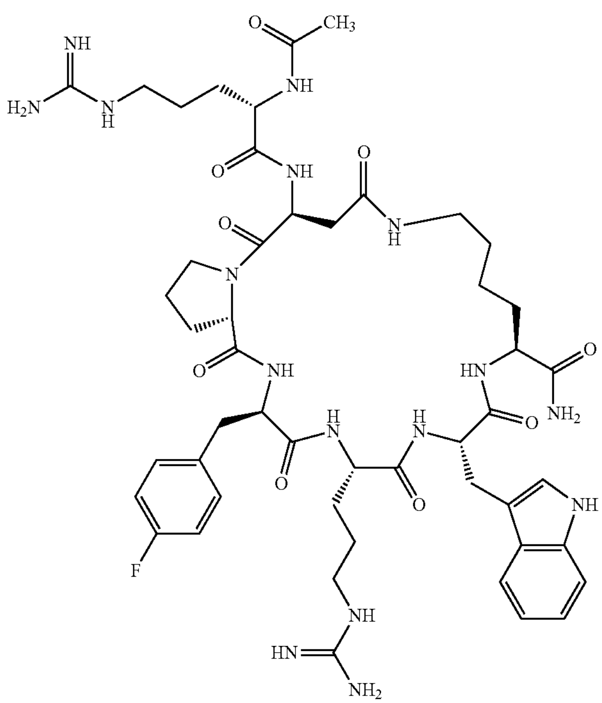 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccc(F)cc2)NC(=O)[C@@H]2CCCN2C1=O] | Ac-Arg-cyclo(Asp-Pro-D-Phe(4-F)-Arg-Trp-Lys)-NH$_2$ (SEQ ID NO: 108) | 4 | — |

-continued

| No. | Structure | Amino Acid Sequence | MC4-R Ki (nM) | MC1-R Ki (nM) |
|---|---|---|---|---|
| 104 | 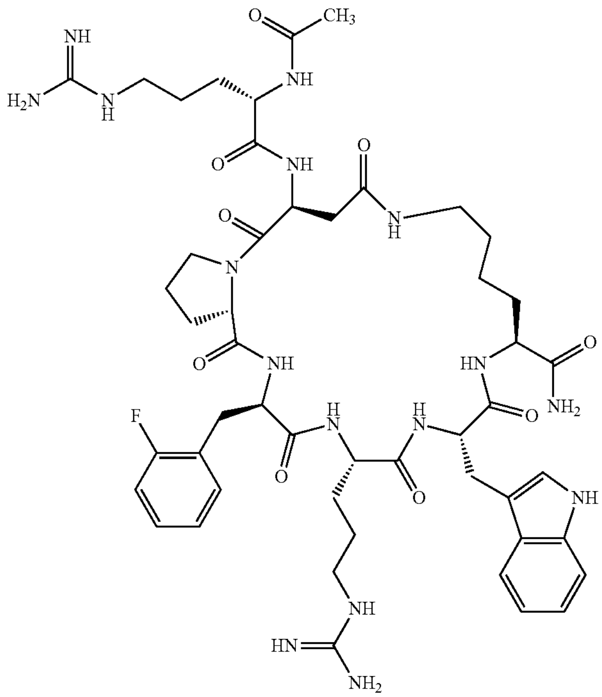 [SMILES: CC(=O)N[C@@H](CCCNC(=N)N)C(=O)N[C@H]1CC(=O)NCCCC[C@@H](C(N)=O)NC(=O)[C@H](Cc2c[nH]c3ccccc23)NC(=O)[C@H](CCCNC(=N)N)NC(=O)[C@@H](Cc2ccccc2F)NC(=O)[C@@H]2CCCN2C1=O] | Ac-Arg-cyclo(Asp-Pro-D-Phe(2-F)-Arg-Trp-Lys)-NH$_2$ (SEQ ID NO: 109) | 78 | — |
| 105 | 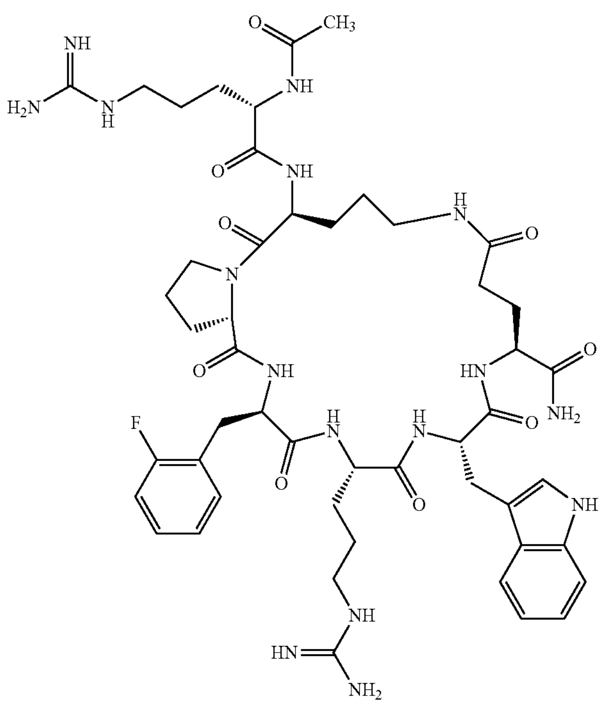 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2F)NC(=O)[C@@H]2CCCN2C1=O] | Ac-Arg-cyclo(Orn-Pro-D-Phe(2-F)-Arg-Trp-Glu)-NH$_2$ (SEQ ID NO: 110) | 7 | — |

| No. | Structure | Amino Acid Sequence | MC4-R Ki (nM) | MC1-R Ki (nM) |
|---|---|---|---|---|
| 106 | 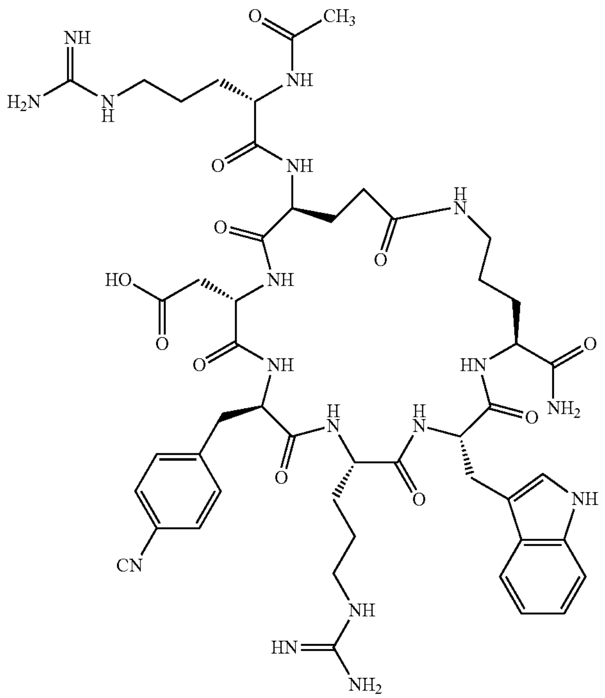 | Ac-Arg-cyclo(Glu-Asp-D-Phe(4-CN)-Arg-Trp-Orn)-NH$_2$ (SEQ ID NO: 111) | 647 | 10000 |
| 107 | 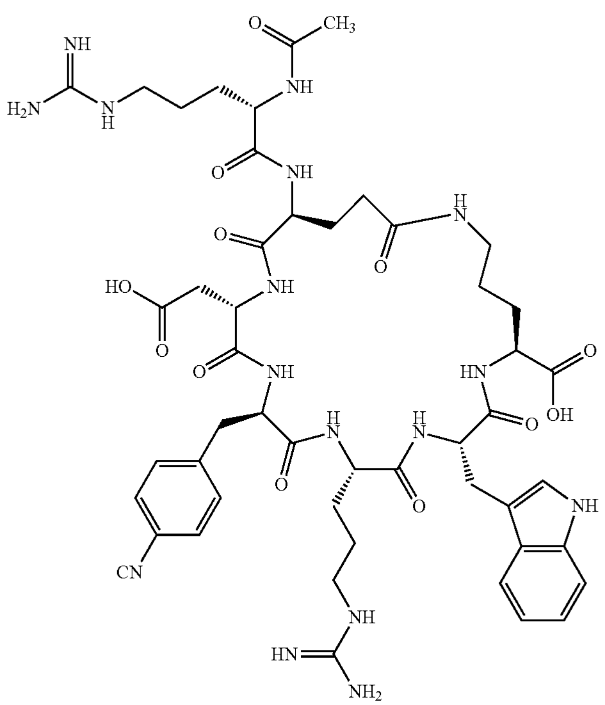 | Ac-Arg-cyclo(Glu-Asp-D-Phe(4-CN)-Arg-Trp-Orn)-OH (SEQ ID NO: 112) | 6463 | 10000 |

| No. | Structure | Amino Acid Sequence | MC4-R Ki (nM) | MC1-R Ki (nM) |
|---|---|---|---|---|
| 108 | 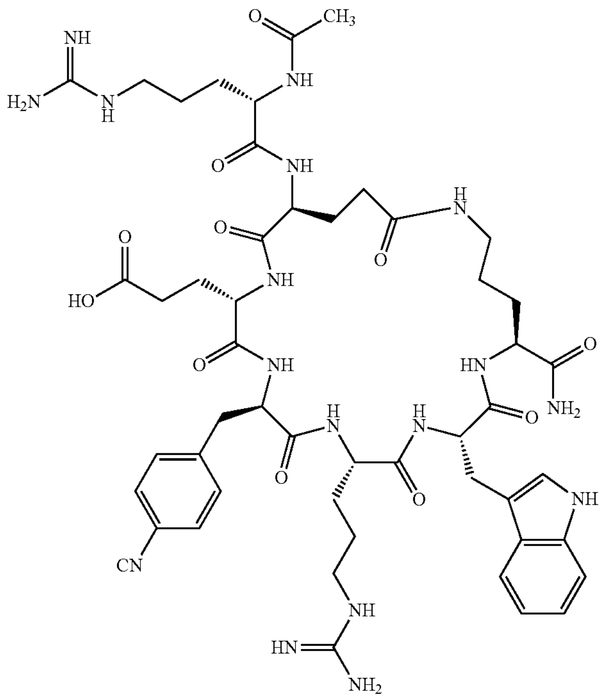 | Ac-Arg-cyclo(Glu-Glu-D-Phe(4-CN)-Arg-Trp-Orn)-NH$_2$ (SEQ ID NO: 113) | 128 | 10000 |
| 109 | 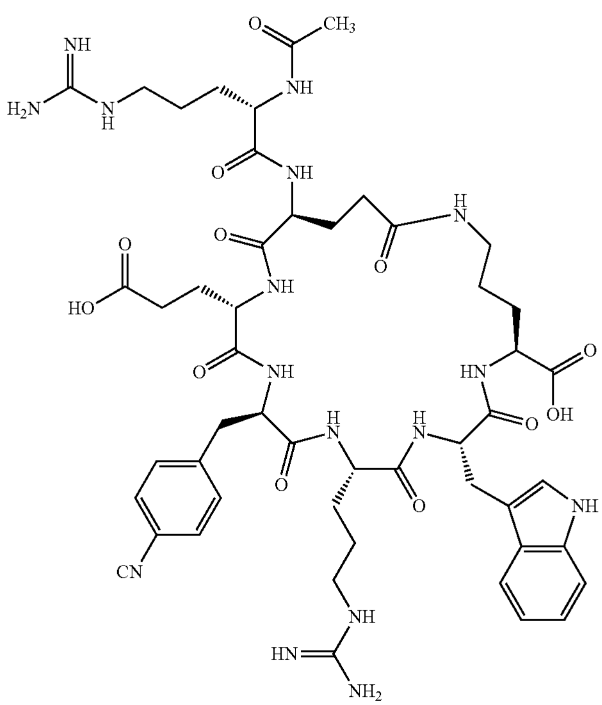 | Ac-Arg-cyclo(Glu-Glu-D-Phe(4-CN)-Arg-Trp-Orn)-OH (SEQ ID NO: 114) | 1090 | 10000 |

| No. | Structure | Amino Acid Sequence | MC4-R Ki (nM) | MC1-R Ki (nM) |
|-----|-----------|---------------------|---------------|---------------|
| 110 | 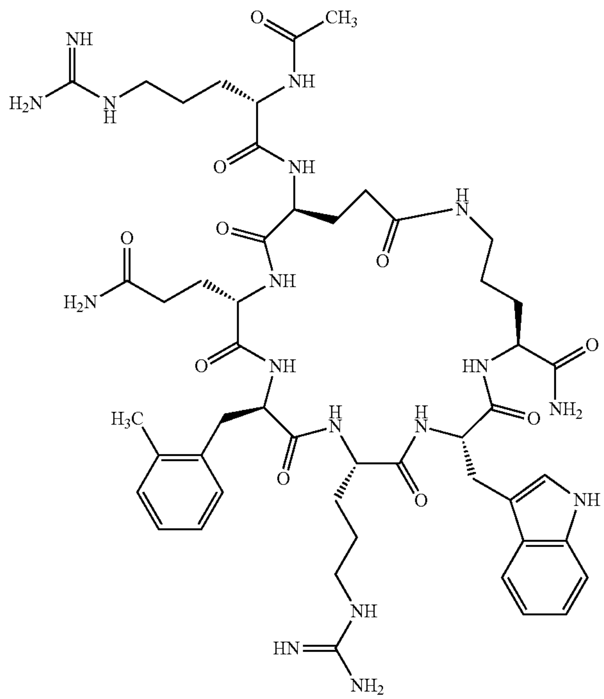 [SMILES: CC(=O)N[C@@H](CCCNC(=N)N)C(=O)N[C@H]1CCC(=O)NCCC[C@@H](C(N)=O)NC(=O)[C@H](Cc2c[nH]c3ccccc23)NC(=O)[C@H](CCCNC(=N)N)NC(=O)[C@@H](Cc2ccccc2C)NC(=O)[C@H](CCC(N)=O)NC1=O] | Ac-Arg-cyclo(Glu-Gln-D-Phe(2-Me)-Arg-Trp-Orn)-NH$_2$ (SEQ ID NO: 115) | 5 | 105 |
| 111 | 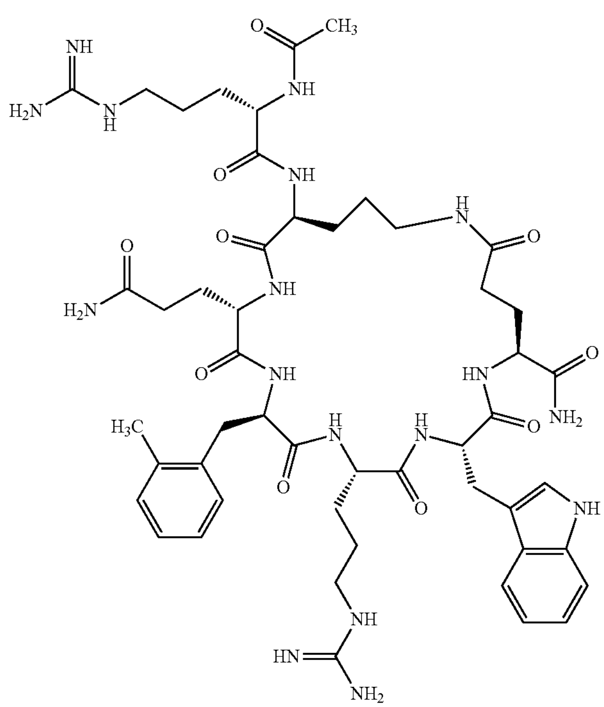 | Ac-Arg-cyclo(Orn-Gln-D-Phe(2-Me)-Arg-Trp-Glu)-NH$_2$ (SEQ ID NO: 116) | 6 | 145 |

-continued

| No. | Structure | Amino Acid Sequence | MC4-R Ki (nM) | MC1-R Ki (nM) |
|---|---|---|---|---|
| 112 | 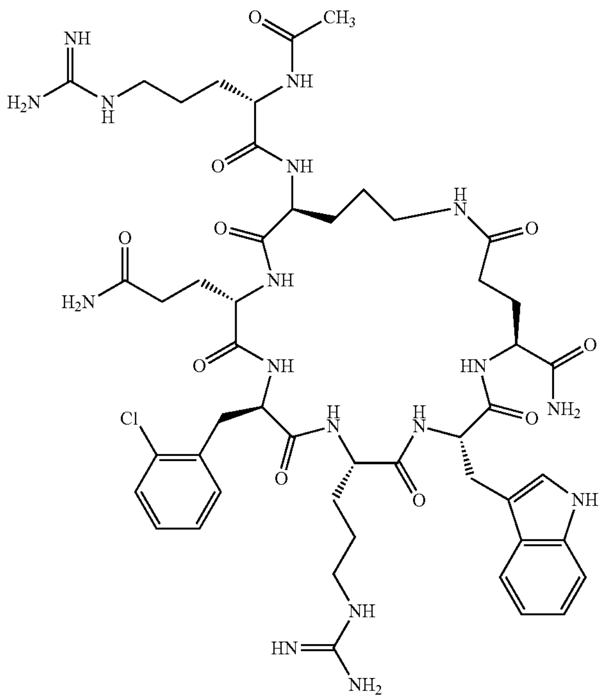 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2C)NC(=O)[C@H](CCC(N)=O)NC1=O] | Ac-Arg-cyclo(Orn-Gln-D-Phe(2-Cl)-Arg-Trp-Glu)-NH$_2$ (SEQ ID NO: 117) | 4 | 83 |
| 113 | 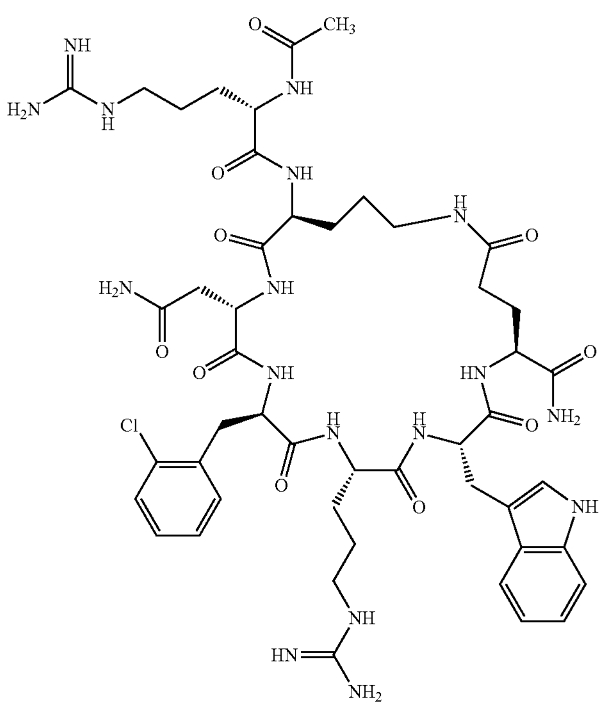 | Ac-Arg-cyclo(Orn-Asn-D-Phe(2-Cl)-Arg-Trp-Glu)-NH$_2$ (SEQ ID NO: 118) | 7 | 255 |

| No. | Structure | Amino Acid Sequence | MC4-R Ki (nM) | MC1-R Ki (nM) |
|---|---|---|---|---|
| 114 | 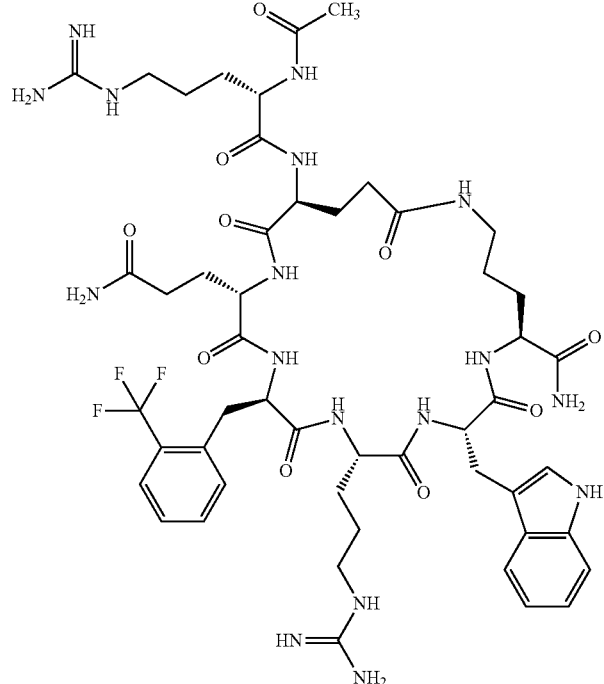 | Ac-Arg-cyclo(Glu-Gln-D-Phe(2-CF₃)-Arg-Trp-Orn)-NH₂ (SEQ ID NO: 119) | 8 | 93 |
| 115 | 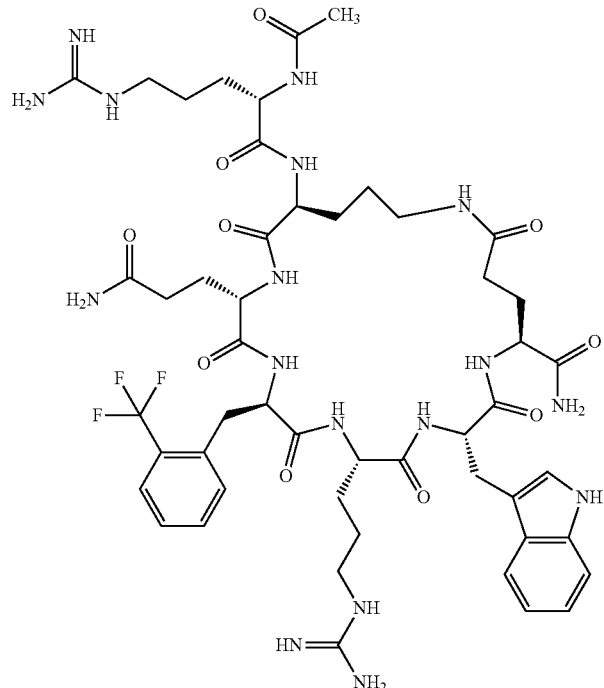 | Ac-Arg-cyclo(Orn-Gln-D-Phe(2-CF₃)-Arg-Trp-Glu)-NH₂ (SEQ ID NO: 120) | 4 | 235 |

| No. | Structure | Amino Acid Sequence | MC4-R Ki (nM) | MC1-R Ki (nM) |
|---|---|---|---|---|
| 116 | 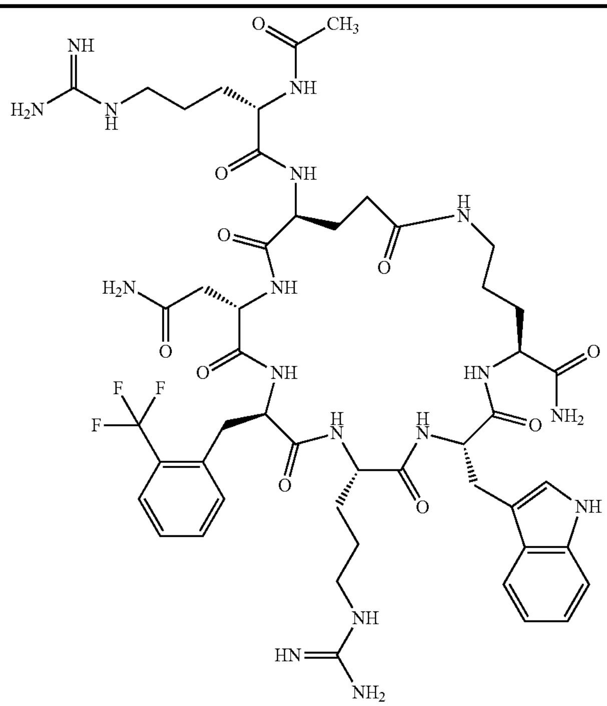 | Ac-Arg-cyclo(Glu-Asn-D-Phe(2-CF3)-Arg-Trp-Orn)-NH2 (SEQ ID NO: 121) | 7 | 380 |
| 117 | 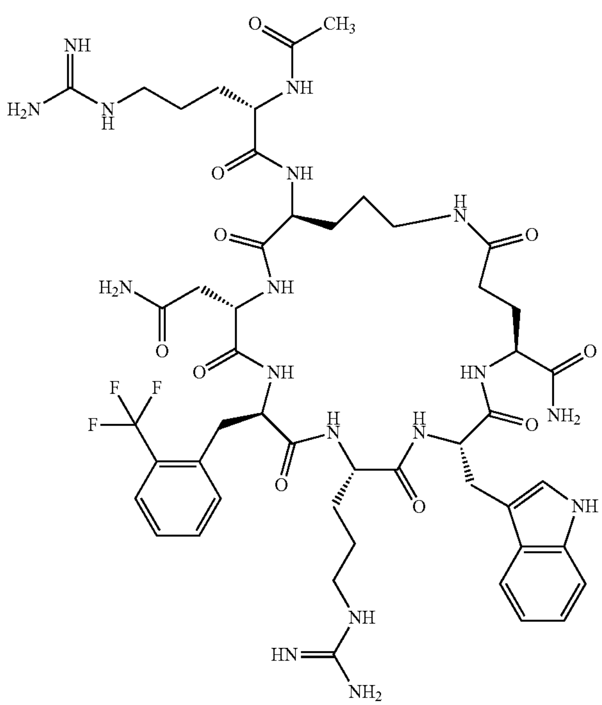 [SMILES: CC(=O)N[C@@H](CCCNC(=N)N)C(=O)N[C@H]1CCCNC(=O)CC[C@@H](C(N)=O)NC(=O)[C@H](Cc2c[nH]c3ccccc23)NC(=O)[C@H](CCCNC(=N)N)NC(=O)[C@@H](Cc2ccccc2C(F)(F)F)NC(=O)[C@H](CC(N)=O)NC1=O] | Ac-Arg-cyclo(Orn-Asn-D-Phe(2-CF3)-Arg-Trp-Glu)-NH2 (SEQ ID NO: 122) | 5 | 540 |

7.0 Tests and Assays Employed in Evaluation of the Peptides of the Present Invention The melanocortin receptor-specific peptides of this invention may be tested by a variety of assay systems and animal models to determine binding, functional status and efficacy.

7.1 Competitive Inhibition Assay using $[I^{125}]$-NDP-α-MSH.

A competitive inhibition binding assay was performed for exemplified peptides according to the invention using membrane homogenates prepared from HEK-293 cells that express recombinant hMC4-R, hMC3-R, or hMC5-R, and from B-16 mouse melanoma cells (containing endogenous MC1-R). In some instances, HEK-293 cells that express recombinant hMC1-R were employed. Assays were performed in 96 well GF/B Millipore multiscreen filtration plates (MAFB NOB10) pre-coated with 0.5% bovine serum albumin (Fraction V). Membrane homogenates were incubated with 0.2 nM (for hMC4-R) 0.4 nM (for MC3-R and MC5-R) or 0.1 nM (for mouse B16 MC1-R or hMC1-R) $[I^{125}]$-NDP-α-MSH (Perkin Elmer) and increasing concentrations of test peptides of the present invention in buffer containing 25 mM HEPES buffer (pH 7.5) with 100 mM NaCl, 2 mM $CaCl_2$, 2 mM $MgCl_2$, 0.3 mM 1,10-phenanthroline, and 0.2% bovine serum albumin. After incubation for 60 minutes at 37° C., the assay mixture was filtered and the membranes washed three times with ice-cold buffer. Filters were dried and counted in a gamma counter for bound radioactivity. Non-specific binding was measured by inhibition of binding of $[I^{125}]$-NDP-α-MSH in the presence of 1 μM NDP-α-MSH. Maximal specific binding (100%) was defined as the difference in radioactivity (cpm) bound to cell membranes in the absence and presence of 1 μM NDP-α-MSH. Radioactivity (cpm) obtained in the presence of test peptides was normalized with respect to 100% specific binding to determine the percent inhibition of $[I^{125}]$-NDP-α-MSH binding. Each assay was conducted in triplicate and the actual mean values are described, with results less than 0% reported as 0%. Ki values for test peptides of the present invention were determined using Graph-Pad Prism® curve-fitting software. Results from this assay are presented herein (see 6.1). For some peptides, a mean value of more than two values is presented.

7.2 Assay for Agonist Activity.

Accumulation of intracellular cAMP was examined as a measure of the ability of peptides of the present invention to elicit a functional response in HEK-293 cells that is express MC4-R. Confluent HEK-293 cells that express recombinant hMC4-R were detached from culture plates by incubation in enzyme-free cell dissociation buffer. Dispersed cells were suspended in Earle's Balanced Salt Solution containing 10 mM HEPES (pH 7.5), 1 mM $MgCl_2$, 1 mM glutamine, 0.5% albumin and 0.3 mM 3-isobutyl-1-methyl-xanthine (IBMX), a phosphodiesterase inhibitor. The cells were plated in 96-well plates at a density of $0.5 \times 10^5$ cells per well and pre-incubated for 10 minutes. Cells were exposed for 15 minutes at 37° C. to peptides of the present invention dissolved in DMSO (final DMSO concentration of 1%) at a concentration range of 0.05-5000 nM in a total assay volume of 200 μL. NDP-α-MSH was used as the reference agonist. cAMP levels were determined by an HTRF® cAMP cell-based assay system from Cisbio Bioassays utilizing cryptate-labeled anti-cAMP and d2-labeled cAMP, with plates read on a Perkin-Elmer Victor plate reader at 665 and 620 nM. Data analysis was performed by nonlinear regression analysis with Graph-Pad Prism® software. The maximum efficacies of test peptides of the present invention were compared to that achieved by the reference melanocortin agonist NDP-α-MSH, used as full agonist benchmark in this context.

7.3 High and Low Density hMC4-R Functional Assay.

A HEK293 cell line transfected with human MC4-R (Palatin Technologies, US, with license from the University of Michigan) was used. The human MC4-R was introduced to HEK293 by using the T-REx™ System, Invitrogen. The T-REx™ System employs a tetracycline-regulated mammalian expression system that uses regulatory elements from the E. coli Tn10-encoded tetracycline (Tet) resistance operon. By use of the T-REx™ System, expression of the gene of interest, the human MC4-R gene, is repressed in the absence of tetracycline or doxycycline and induced in the presence of tetracycline or doxycycline (see T-REx™ System Manual, published by Invitrogen).

HEK293-T-REx-MC4-R cells were cultured in DMEM (Gibco 11965), supplemented with L-Glutamine (Gibco 25030), 10% fetal bovine serum (FBS), 200 μg/mL Zeocin (Invitrogen 46-0072) and 6 μg/mL Blasticidin (Invitrogen 46-1120) in 5% $CO_2$ and 95% humidity at 37° C. T-150 flasks of cells at 75% confluence were incubated with two concentrations of doxycycline (0.1 ng/mL to provide a low density hMC4-R system and 10 ng/mL to provide a high density hMC4-R system) in 5% $CO_2$ at 37° C. for 16-18 hours to induce MC4-R expression. On the day of the assay, the cells were washed with PBS (Gibco 14190) and harvested using cell dissociation buffer (Gibco 13150-016), then centrifuged and resuspended in Hanks' Balanced Salt Solution (+Ca, +Mg) (Gibco 14025), 10 mM 4-(2-hydroxyethyl)-1-piperazineethanesulfonic acid (HEPES) (pH 7.4) (Sigma H0887), 1 mM L-Glutamine (Gibco 25030), 1 mg/mL bovine serum albumin (BSA) (Sigma A3311) and 0.3 mM 3-isobutyl-1-methyl-xanthine (IBMX). Cells were then counted and volume was adjusted to $2.5 \times 10^5$ cells per ml.

The cells were then dispensed into 96-well plates (BD 353916) in 198 μL (about $5 \times 10^4$) cells/well and incubated for 10 minutes at 37° C. The compound to be tested was diluted with DMSO to a final concentration of 1 mM. Serial dilution was prepared in polypropylene removable 12-well library tube strips (VWR cat#83009-682). 120 μL of the 1 mM compound stock was pipetted in the second column on the plate. Using the Janus liquid handler the compound was serially diluted 1:10 (25 μL compound+225 μL DMSO) to a total of 9 concentrations (representing final assay concentrations ranging from $10^{-5}$ to $10^{-13}$ M).

2 μL of the standard, [$Nle^4$, D-$Phe^7$]-alpha-Melanocyte Stimulating Hormone (NDP-α-MSH), or compound was added to the 96-well plate using the Janus robotic system. All assay samples were run in duplicate (i.e. each sample was in two low dox and two high dox plates, respectively). The plates were gently shaken and incubated for 15 minutes at 37° C. The reaction was stopped by adding 15 μL of lysis buffer per well and the plates were shakened for 30 minutes at room temperature.

Agonist stimulation of the MC4-R activates adenylate cyclase, which is an enzyme that catalyses the formation 3',5'-cyclic adenosine monophosphate (cAMP) from adenosine triphosphate (ATP). Thus, agonist stimulation of the MC4-R increases the levels of cAMP. cAMP-levels were measured with the cAMP dynamic 2 HTRF kit (CisBio cat#62AM4PEC; see manual published by CisBio). cAMP levels were normalized against plate controls (1% DMSO for 0%, 400 nM NDP-α-MSH for 100%) and a calibration curve ranging from 712 nM to 0.04 nM cAMP (essentially as described in the CisBio HTRF kit). The plates were incubated on a shaker at room temperature for 1 hour and read on the Perkin-Elmer Victor plate reader at 665 and 620 nm. Fluorescence ratios were then calculated as described in the CisBio HTRF kit, with GraphPad Prism software used to plot the change in fluorescence percent values versus cAMP concentration using the variable slope dose response curve and, based on calculated cAMP concentrations, to determine $EC_{50}$ values and percent activation. Results from this assay are presented herein (see 8.0).

7.4 Food Intake and Body Weight Change.

Change in food intake and body weight was evaluated for selected peptides administered by subcutaneous injection route. Male Sprague-Dawley rats were obtained from Hilltop Lab Animals, Inc. (Scottdale, Pa.). Animals were individually housed in conventional polystyrene hanging cages and maintained on a controlled 12 hour on/off light cycle. Water and pelleted food (ProLab RMH 2500, W.F. Fisher & Son Inc.) was provided ad libitum. The rats were dosed subcutaneously with vehicle (3.2% mannitol/50 mM Tris buffer) or selected peptides (1.0 mg/kg). The changes in food intake for the 4 and 24 hour periods after dosing and the changes in body weight for the 24 hour period after dosing were determined. The changes in body weight and food intake for the 48 hour and 72 hour periods after dosing was also measured to determine reversal of changes in body weight and food intake effects back to baseline levels (not shown).

Food intake (FI, 0-4 h and 0-24 h) and body weight (BW, 0-24 h) results from studies with 1.0 mg/kg subcutaneously of Examples 43, 46 and 67 and corresponding vehicle controls run in parallel are shown in Table 2 below, expressed as means±SEM (n=8-10).

TABLE 2

| Experiment | Treatment | Dose (mg/kg, s.c.) | n | FI 0-4 h (g) | FI 0-24 h (g) | BW change 0-24 h (g) |
|---|---|---|---|---|---|---|
| 1 | Vehicle | | 10 | 10.53 ± 0.78 | 27.75 ± 1.00 | 1.49 ± 0.18 |
| 1 | Ref Ex 2 | 1.0 | 10 | 4.41 ± 0.48 | 20.84 ± 1.01 | −0.38 ± 0.46 |
| 1 | Ex 43 | 1.0 | 10 | 6.85 ± 0.55 | 24.44 ± 0.85 | 0.45 ± 0.35 |
| 2 | Vehicle | | 8 | 7.09 ± 0.39 | 27.46 ± 1.16 | 1.96 ± 0.55 |
| 2 | Ref Ex 2 | 1.0 | 8 | 2.80 ± 0.27 | 21.81 ± 1.04 | 0.85 ± 0.45 |
| 2 | Ex 46 | 1.0 | 8 | 3.71 ± 0.68 | 20.56 ± 1.14 | −0.29 ± 0.55 |
| 3 | Vehicle | | 8 | 7.76 ± 0.53 | 25.71 ± 0.25 | 2.25 ± 0.50 |
| 3 | Ref Ex 2 | 1.0 | 8 | 3.17 ± 0.42 | 19.98 ± 0.60 | −0.27 ± 0.48 |
| 3 | Ex 67 | 1.0 | 8 | 4.20 ± 0.66 | 21.51 ± 1.27 | −0.05 ± 0.39 |

7.5 Induction of Penile Erection.

The ability of peptides of the present invention to induce penile erection (PE) in male rats was evaluated with selected peptides. Male Sprague-Dawley rats weighing 250-300 g were kept on a 12 hour on/off light cycle with food and water ad libitum. All behavioral studies were performed between 9 a.m. and 4 p.m. Groups of 6-8 rats were administered peptides at a variety of doses via the subcutaneous injection route. Immediately after treatment, rats were placed into individual polystyrene cages (27 cm long, 16 cm wide, and 25 cm high) for behavioral observation, typically by remote video monitoring (High-speed Digital Video Recording System EVS-DSX-16000DVD-H with CCD cameras, Epic Systems Inc., St. Louis, Mo., USA) followed by blinded off-line scoring of video recordings. Rats were observed for one hour, and the number of yawns, grooming bouts and PEs were recorded in 10-minute bins.

PE results from studies with 1.0-3.0 mg/kg subcutaneously of Examples 43, 46 and 67, along with Ref Ex 2, are shown in Table 3 below, expressed as total number of PE/rat, mean±SEM (n=7-11) and number of rats/group showing at least one erection over the study period (% responders). Corresponding vehicle controls (3.2% mannitol/50 mM Tris buffer) were run in parallel.

TABLE 3

| Treatment | Dose (mg/kg, s.c.) | n | Total number of PE/rat 0-1 h | % Responders |
|---|---|---|---|---|
| Vehicle | | 11 | 1.0 ± 0.27 | 64 |
| Ref Ex 2 | 3.0 | 7 | 6.0 ± 0.44 | 100 |
| Ex 43 | 1.0 | 7 | 1.7 ± 0.36 | 29 |
| | 3.0 | 7 | 6.0 ± 0.76 | 100 |
| Ex 46 | 1.0 | 7 | 4.9 ± 1.1 | 100 |
| | 3.0 | 7 | 4.4 ± 1.1 | 86 |

TABLE 3-continued

| Treatment | Dose (mg/kg, s.c.) | n | Total number of PE/rat 0-1 h | % Responders |
|---|---|---|---|---|
| Ex 67 | 1.0 | 7 | 2.3 ± 0.42 | 86 |
| | 3.0 | 7 | 3.3 ± 1.0 | 100 |

8.0 High and Low Density hMC4-R Functional Assay Results

Exemplified peptides were tested using the high and low density hMC4-R functional assay as described in Section 7.3 above, with the results as shown in Table 4 below. Table 4 includes both single point values and mean values.

TABLE 4

| | 0.1 ng/mL Doxycycline | | 10 ng/mL Doxycycline | |
|---|---|---|---|---|
| Compound | $EC_{50}$ (nM) | Intrinsic Activity (%) | $EC_{50}$ (nM) | Intrinsic Activity (%) |
| Example 1 | 0.34 | 91 | 0.045 | 96 |
| Example 2 | 0.56 | 36 | 0.095 | 99 |
| Example 3 | 0.07 | 28 | 0.16 | 100 |
| Example 4 | — | 11 | 0.245 | 100 |
| Example 5 | — | 5 | 0.38 | 92 |
| Example 6 | 37 | 29 | 2 | 100 |
| Example 7 | 0.3 | 48 | 0.135 | 100 |
| Example 8 | 48 | 71 | 0.55 | 87 |
| Example 9 | 0.09 | 91 | 0.035 | 89 |
| Example 10 | 0.45 | 77 | 0.17 | 94 |
| Example 11 | 0.065 | 83 | 0.06 | 90 |
| Example 12 | 34 | 64 | 0.5 | 97 |
| Example 13 | 0.125 | 85 | 0.06 | 96 |
| Example 14 | 8 | 16 | 0.4 | 93 |
| Example 15 | 0.165 | 16 | 0.2 | 90 |
| Example 16 | 0.15 | 28 | 0.16 | 97 |
| Example 17 | 0.95 | 64 | 0.12 | 95 |
| Example 18 | 0.14 | 83 | 0.085 | 97 |
| Example 19 | 0.42 | 35 | 0.22 | 97 |
| Example 20 | — | 0.5 | 0.75 | 53 |
| Example 21 | — | 8 | 0.5 | 97 |
| Example 22 | 3 | 78 | 0.2 | 93 |
| Example 23 | 2 | 17 | 0.55 | 95 |
| Example 24 | 0.7 | 15 | 0.45 | 99 |
| Example 25 | 75 | 23 | 2 | 94 |
| Example 26 | 0.125 | 74 | 0.12 | 90 |
| Example 27 | 0.7 | 37 | 0.33 | 97 |
| Example 28 | 29 | 35 | 0.6 | 94 |
| Example 29 | 3 | 14 | 0.8 | 100 |
| Example 30 | — | 2 | 25 | 9 |
| Example 31 | 7 | 33 | 0.313 | 98 |
| Example 32 | 18 | 34 | 0.543 | 96 |
| Example 33 | 1 | 41 | 0.153 | 98 |
| Example 34 | 1 | 79 | 0.137 | 97 |
| Example 35 | — | 6 | 1 | 84 |
| Example 36 | — | 8 | 1 | 89 |

TABLE 4-continued

|  | 0.1 ng/mL Doxycycline | | 10 ng/mL Doxycycline | |
| --- | --- | --- | --- | --- |
| Compound | $EC_{50}$ (nM) | Intrinsic Activity (%) | $EC_{50}$ (nM) | Intrinsic Activity (%) |
| Example 37 | — | 6 | 0.55 | 90 |
| Example 38 | 2 | 31 | 0.258 | 97 |
| Example 39 | — | 4 | 1 | 79 |
| Example 40 | — | 8 | 0.5 | 93 |
| Example 41 | — | 5 | 0.8 | 84 |
| Example 42 | — | 9 | 0.5 | 84 |
| Example 43 | 1 | 43 | 0.177 | 100 |
| Example 44 | 11 | 22 | 0.617 | 99 |
| Example 45 | — | 12 | 0.45 | 87 |
| Example 46 | 0.666 | 40 | 0.173 | 97 |
| Example 47 | 0.31 | 36 | 0.373 | 100 |
| Example 48 | — | 6 | 4 | 93 |
| Example 49 | 2 | 74 | 0.235 | 93 |
| Example 50 | 0.21 | 94 | 0.085 | 94 |
| Example 51 | 0.64 | 22 | 0.4 | 95 |
| Example 52 | 0.325 | 31 | 0.2 | 99 |
| Example 53 | 0.13 | 86 | 0.13 | 90 |
| Example 54 | 0.075 | 56 | 0.075 | 92 |
| Example 55 | 10 | 28 | 0.8 | 98 |
| Example 56 | 5 | 41 | 0.3 | 98 |
| Example 57 | 0.25 | 89 | 0.095 | 100 |
| Example 58 | 5 | 67 | 0.25 | 100 |
| Example 59 | 0.6 | 90 | 0.1 | 98 |
| Example 60 | 0.45 | 62 | 0.14 | 95 |
| Example 61 | — | 6 | 0.95 | 89 |
| Example 62 | 16 | 23 | 0.47 | 84 |
| Example 63 | 0.37 | 30 | 0.157 | 93 |
| Example 64 | 1 | 57 | 0.08 | 90 |
| Example 65 | 1 | 58 | 0.085 | 93 |
| Example 66 | 5 | 32 | 0.265 | 88 |
| Example 67 | 1 | 38 | 0.14 | 99 |
| Example 68 | 0.85 | 55 | 0.075 | 91 |
| Example 69 | 0.25 | 76 | 0.095 | 92 |
| Example 70 | 0.4 | 64 | 0.1 | 91 |
| Example 71 | 1 | 86 | 0.085 | 91 |
| Example 72 | 3 | 11 | 0.35 | 84 |
| Example 73 | 0.587 | 86 | 0.068 | 102 |
| Example 74 | 0.943 | 68 | 0.11 | 100 |
| Example 75 | 0.65 | 43 | 0.125 | 87 |
| Example 76 | 3 | 53 | 0.135 | 85 |
| Example 77 | 3 | 34 | 0.155 | 80 |
| Example 78 | 2 | 48 | 0.2 | 89 |
| Example 79 | 4 | 48 | 0.2 | 85 |
| Example 80 | 6 | 13 | 0.65 | 86 |
| Example 81 | 4 | 23 | 0.45 | 85 |
| Example 82 | 2 | 79 | 0.095 | 95 |
| Example 83 | 0.75 | 78 | 0.075 | 94 |
| Example 84 | 0.633 | 78 | 0.09 | 97 |
| Example 85 | 15 | 36 | 0.707 | 94 |
| Example 86 | 9 | 36 | 0.483 | 96 |
| Example 87 | 1 | 64 | 0.065 | 100 |
| Example 88 | 3 | 15 | 0.35 | 89 |
| Example 89 |  | 6 | 17 | 87 |
| Example 90 | 4 | 31 | 0.283 | 96 |
| Example 91 | 1 | 18 | 0.265 | 96 |
| Example 92 | 0.1 | 81 | 0.04 | 89 |
| Example 93 | 0.3 | 44 | 0.17 | 97 |
| Example 94 | 0.24 | 32 | 0.09 | 92 |
| Example 95 | 1 | 42 | 0.125 | 100 |
| Example 96 | 2 | 24 | 0.235 | 100 |
| Example 97 | 0.8 | 49 | 0.1 | 100 |
| Example 98 | 0.45 | 47 | 0.14 | 100 |
| Example 99 | 0.7 | 32 | 0.14 | 94 |
| Example 100 | 6 | 27 | 0.27 | 93 |
| Example 101 | 0.95 | 36 | 0.14 | 93 |
| Example 102 | 18 | 30 | 0.725 | 97 |
| Example 103 | 1 | 32 | 0.13 | 100 |
| Example 104 | 191 | 16 | 10 | 100 |
| Example 105 | 3 | 35 | 0.15 | 94 |
| Example 106 |  | 3 | 113 | 77 |
| Example 107 |  | 4 |  | 64 |
| Example 108 |  | 3 | 9 | 59 |
| Example 109 |  | 2 | 269 | 69 |
| Example 110 | 0.6 | 84 | 0.06 | 105 |
| Example 111 | 0.575 | 81 | 0.053 | 104 |
| Example 112 | 0.39 | 83 | 0.07 | 101 |
| Example 113 | 0.72 | 80 | 0.065 | 100 |
| Example 114 | 1 | 73 | 0.185 | 117 |
| Example 115 | 0.8 | 54 | 0.17 | 108 |
| Example 116 | 0.68 | 77 | 0.095 | 104 |
| Example 117 | 1 | 50 | 0.18 | 112 |

It is believed that peptides of the invention exhibiting an intrinsic activity of equal to or greater than about 0.1 (10%), such as greater than 0.2 (20%) or greater than about 0.3 (30%) or greater than about 0.4 (40%) or greater than about 0.5 (50%) or greater than about 0.6 (60%) % or greater than about 0.7 (70%), or greater than about 0.8 (80%), or greater than about 0.9 (90%), or equal to or greater than about 1.0 (100%), in the above described high density hMC4-R system (i.e. HEK293TRexMC4R cells treated with 10 ng/ml doxycycline), based on maximal stimulation of adenylyl cyclase achievable by the compound in the same high density hMC4-R system where the maximal stimulation achieved by α-MSH or NDP-α-MSH is designated as an intrinsic activity of 1.0 (100%), provide agonist (full or partial) activity on the MC4 receptor.

A majority of the peptides of the Examples which were tested in the above described high density hMC4-R system (i.e. HEK293TRexMC4R cells treated with 10 ng/ml doxycycline) gave in said assay $EC_{50}$ values for cAMP production of less than 0.05 μM, such as less than 0.01 μM, and in particular less than 0.001 μM.

As seen from Table 4, peptides of the invention may lack intrinsic activity in the low density hMC4-R system and be full agonists in the high density hMC4-R system.

As further seen from Table 4, peptides of the invention may be partial agonists in the above described low density hMC4-R system and full agonists in the above described high density hMC4-R system.

As further seen from Table 4, peptides of the invention may be full agonists in both the low density hMC4-R system and in the high density hMC4-R system.

Without being bound by any theory, it is believed that peptides that either lack intrinsic activity or are partial agonists in the above described low density hMC4-R system (i.e. peptides having intrinsic activity of from 0 to 70% in the low density hMC4-R system) and are partial or full agonists in the above described high density hMC4-R system (i.e. peptides having intrinsic activity of equal to or above 10%, or above 70%, in the high density hMC4-R system) will provide no or a reduced level of sexual effects resulting from MC4 receptor activation, e.g. penile erection, compared to peptides being full agonists in both the low and the high density hMC4-R systems. As explained above, these sexual effects are considered unwanted side-effects upon treatment of energy homeostasis and metabolism related, food intake related and/or energy balance and body weight related diseases, disorders and/or conditions.

It is thus believed that peptides according to the invention possess promising MC4 receptor affinity, efficacy and potency to be useful for treatment of diseases, disorders and/or conditions responsive to activation of the MC4 receptor, in particular energy homeostasis and metabolism related (e.g. diabetes), food intake related and/or energy balance and body weight related diseases, disorders and/or conditions, including obesity, overweight and diseases, disorders and/or conditions associated with obesity and/or overweight, such as type 2 diabetes and metabolic syndrome.

Although the invention has been described in detail with particular reference to these preferred embodiments, other embodiments can achieve the same results. Variations and modifications of the present invention will be obvious to those skilled in the art and it is intended to cover all such modifications and equivalents.

The invention claimed is:

1. A cyclic peptide of Formula (I):

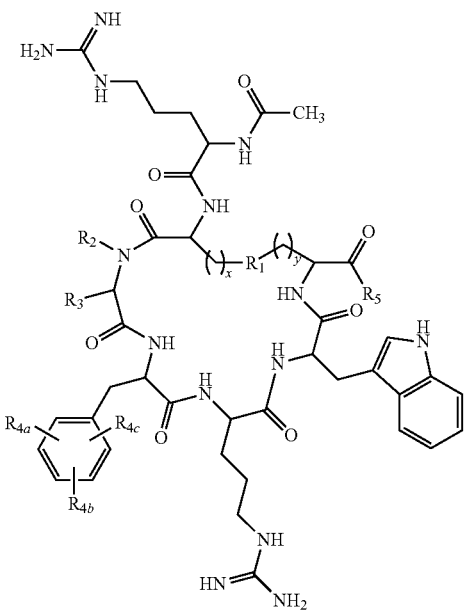

(I)

or a pharmaceutically acceptable salt thereof,
wherein:
$R_1$ is —NH—C(=O)— or —C(=O)—NH—;
$R_2$ is —H or —CH$_2$—, wherein if $R_2$ is —CH$_2$—, then $R_2$ forms with $R_3$ a pyrrolidine ring, wherein the pyrrolidine ring is optionally substituted with —OH;
$R_3$ is —(CH$_2$)$_2$— if $R_2$ is —CH$_2$—, and otherwise $R_3$ is selected from the group consisting of: —(CH$_2$)$_{1-4}$NH$_2$, CH$_3$, —CH(CH$_3$)$_2$, —C(CH$_3$)$_3$, —CH$_2$OH, —CH(OH)CH$_3$, —(CH$_2$)$_{1-2}$CONH$_2$, —CH$_2$(imidazole), —(CH$_2$)$_{1-2}$CO$_2$H, —CH$_2$OBz, —CH(CH$_3$)OBz, —CH$_2$Ph(CONH$_2$), —(CH$_2$)$_2$NHCOCH$_3$, —(CH$_2$)$_3$NHC(=NH)NH$_2$ and —(CH$_2$)$_2$SO$_2$CH$_3$;
$R_{4a}$, $R_{4b}$ and $R_{4c}$ are each independently selected from the group consisting of: —H, —Cl, —F, —CN, —OH, —CF$_3$, —CH$_3$, —OCH$_3$, —NO$_2$, -Ph and —NH$_2$, with the provisos that at least one of $R_{4a}$, $R_{4b}$ and $R_{4c}$ is not hydrogen and that $R_{4a}$, $R_{4b}$ and $R_{4c}$ cannot all be —Cl, —CH$_3$ or —OCH$_3$
$R_5$ is —OH or —N($R_{6a}$)($R_{6b}$);
$R_{6a}$ and $R_{6b}$ are each H;
x is 1 to 4; and
y is 1 to 4.

2. The cyclic peptide of claim 1 which is of Formula (II):

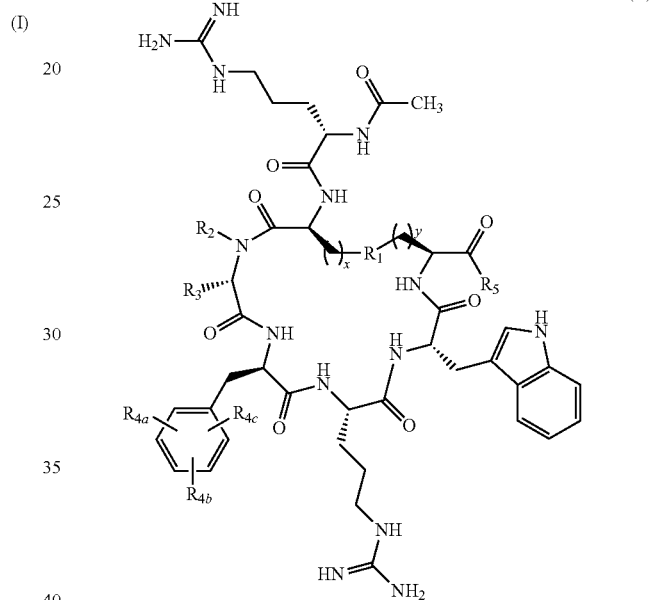

(II)

or a pharmaceutically acceptable salt thereof.

3. The cyclic peptide of claim 1,
wherein:
$R_1$ is —C(=O)—NH—;
x is 2; and
y is 3.

4. The cyclic peptide of claim 1,
wherein:
$R_1$ is —NH—C(=O)—;
x is 3; and
y is 2.

5. The cyclic peptide of claim 1,
wherein:
$R_2$ is H or —CH$_2$—, wherein if $R_2$ is —CH$_2$—, then $R_2$ forms with $R_3$ a pyrrolidine ring, wherein the pyrrolidine ring is optionally substituted with —OH; and
$R_3$ is —(CH$_2$)$_2$— if $R_2$ is —CH$_2$—, and otherwise $R_3$ is selected from the group consisting of: —(CH$_2$)$_{1-4}$NH$_2$, —CH$_3$, —CH$_2$OH, —CH(OH)CH$_3$, —(CH$_2$)$_{1-2}$CONH$_2$, —(CH$_2$)$_2$NHCOCH$_3$, —(CH$_2$)$_3$NHC(=NH)NH$_2$ and —(CH$_2$)$_2$SO$_2$CH$_3$.

6. The cyclic peptide of claim 1,
wherein:
$R_2$ is H; and $R_3$ is selected from the group consisting of:

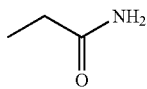 and 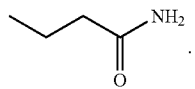.

7. The cyclic peptide of claim 1, wherein $R_2$ and $R_3$ together form an unsubstituted pyrrolidine ring.

8. The cyclic peptide of claim 1 wherein $R_{4a}$ is in the 4-position and is —C≡N and wherein $R_{4b}$ and $R_{4c}$ are each —H.

9. The cyclic peptide of claim 1, wherein $R_{4a}$ is in the 4-position and is —F and wherein $R_{4b}$ and $R_{4c}$ are each —H.

10. A cyclic peptide selected from the group consisting of:
Ac-Arg-cyclo(Glu-Asn-D-Phe(4-CN)-Arg-Trp-Orn)-NH$_2$ (SEQ ID NO:48);
Ac-Arg-cyclo(Glu-Gln-D-Phe(4-CN)-Arg-Trp-Orn)-NH$_2$ (SEQ ID NO:51);
Ac-Arg-cyclo(Glu-Asn-D-Phe(4-F)-Arg-Trp-Orn)-NH$_2$ (SEQ ID NO:74);
Ac-Arg-cyclo(Glu-Asn-D-Phe(4-CN)-Arg-Trp-Orn)-OH (SEQ ID NO:90);
Ac-Arg-cyclo(Glu-Gln-D-Phe(4-CN)-Arg-Trp-Orn)-OH (SEQ ID NO:91);
Ac-Arg-cyclo(Glu-Gln-D-Phe(4-F)-Arg-Trp-Orn)-NH$_2$ (SEQ ID NO:97);
Ac-Arg-cyclo(Glu-Pro-D-Phe(4-CN)-Arg-Trp-Orn)-NH$_2$ (SEQ ID NO:44);
Ac-Arg-cyclo(Glu-Pro-D-Phe(4-F)-Arg-Trp-Orn)-NH$_2$ (SEQ ID NO:72); and
Ac-Arg-cyclo(Glu-Pro-D-Phe(4-F)-Arg-Trp-Orn)-OH (SEQ ID NO:107);
or a pharmaceutically acceptable salt of any of the foregoing.

11. A pharmaceutical composition comprising a cyclic peptide or a pharmaceutically acceptable salt thereof of claim 1 and a pharmaceutically acceptable carrier.

* * * * *